United States Patent [19]
Seegobin

[11] Patent Number: 5,954,664
[45] Date of Patent: Sep. 21, 1999

[54] NONINVASIVE SYSTEM AND METHOD FOR IDENTIFYING CORONARY DISFUNCTION UTILIZING ELECTROCARDIOGRAPHY DERIVED DATA

[76] Inventor: Ronald D. Seegobin, 3179 Bur Creek Rd., Westbrook Ontario, Canada, K0H 2X0

[21] Appl. No.: 08/908,543

[22] Filed: Aug. 7, 1997

Related U.S. Application Data

[63] Continuation-in-part of application No. 08/418,175, Apr. 6, 1995, Pat. No. 5,655,540.

[51] Int. Cl.$^6$ .................................................... A61B 5/046
[52] U.S. Cl. ............................................................ 600/515
[58] Field of Search ..................................... 600/515–518

[56] References Cited

U.S. PATENT DOCUMENTS

| | | | |
|---|---|---|---|
| 4,667,682 | 5/1987 | Ihlenfeld, III | 128/11 |
| 4,680,708 | 7/1987 | Ambor et al. | 364/417 |
| 5,020,540 | 6/1991 | Chamoun | 128/696 |
| 5,025,794 | 6/1991 | Albert et al. | 128/696 |
| 5,027,824 | 7/1991 | Dougherty et al. | 128/702 |
| 5,077,667 | 12/1991 | Brown et al. | 364/413.05 |
| 5,092,341 | 3/1992 | Helen | 128/702 |
| 5,215,099 | 6/1993 | Heberl et al. | 128/702 |
| 5,257,621 | 11/1993 | Bardy et al. | 607/5 |
| 5,509,425 | 4/1996 | Feng | 128/702 |

OTHER PUBLICATIONS

Perioperative Cardiac Morbidity; Concepts and Cortroverrier, Mangana.
High Frequency QRS Electrocardiography in the Detection—Clin. Cardio 17, 175, 182 (1994) Aversano et al.
Phare and Group–Delay Characteristics of Signal–Averaged—Arthur et al., IEEE Transactions on Biomed Eng. vol. 42, No. 1, (1995).
Prognosis and Management After a First Mycardial Infarction, Moss et al., New England J. Medicine, vol. 322, No. 11, Mar. 15, 1990.
The Meaning and Use of the Area Under a Receiver Operating—Hanely et al., Diagnostic Radiology, vol. 143, No. 1, (Apr. 1982).
Predictive Valve of a Single Diagnostic Test in Unselected Populations, Uecchio et al., vol. 274, No. 21, New England J. Med. May 1996.
Analysis of Abnormal Signals Within the QRS Complex of the High—Gomis et al., Transaction on Biomedical Engineering, vol. 44, No. 8, Aug. 1997.

*Primary Examiner*—William E. Kamm
*Attorney, Agent, or Firm*—James D. Welch

[57] ABSTRACT

A system and method for analyzing experimentally obtained electrocardiograph ECG data, which allows accurate catagorization of subjects into various abnormal and normal classifications, and which allows acurate tracking of subject cardiac status change, is disclosed. The method applies an algorithm which compares representative parameter, (eg. root-mean-square RMS mean), values derived from analysis of a representative composite of selected portions of a number of ECG PQRST waveforms obtained from ECG investigation of a subject, to similarly derived representative parameter, (eg. RMS mean and RMS standard deviation), values present in a compiled data bank derived from ECG investigation of numerous normals, (or initial subject data), in each of a plurality of frequency range bands. A highly diagnostic numerical "Score" is calculated by addition of "Score" components found to be acceptable under certain mathematical criteria, and provided by the algorithm. Visually interpretable power spectral density plots supplement the method. In addition, comparison of the calculated "Score" to subject cardiac ejection fraction provides indication of risk for sudden death. The present invention is directly adapted to tracking subject cardiac status change by substituting a baseline subject data set for the normal population data set.

26 Claims, 22 Drawing Sheets

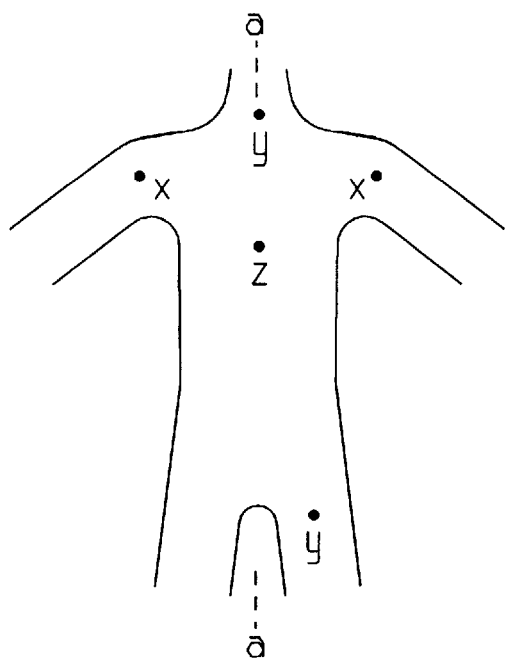
FIG. 1a
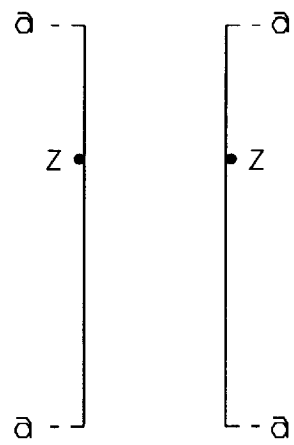
FIG. 1b
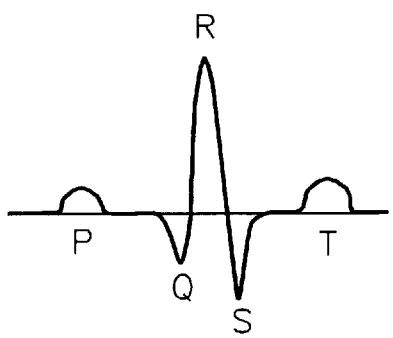
FIG. 2
| FREQUENCIES PRESENT | FRANK (ECG) LEAD | | |
|---|---|---|---|
| | X | Y | Z |
| ALL | | | |
| 0-10 Hz | | | |
| 10-60 Hz | | | |
| 60-150 Hz | | | |
| 150-250 Hz | | | |
FIG. 3

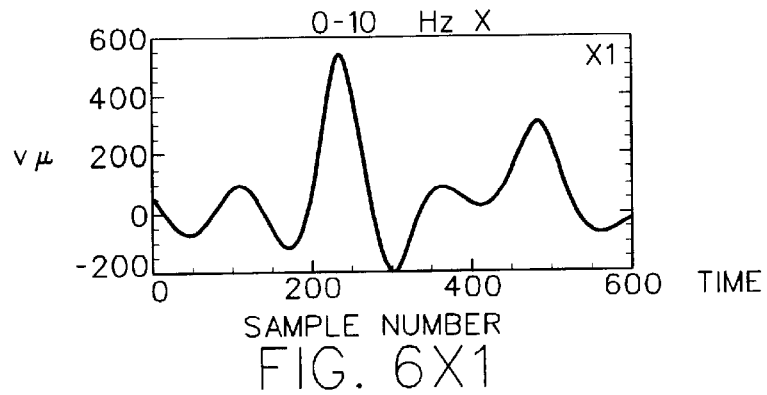
FIG. 6X1
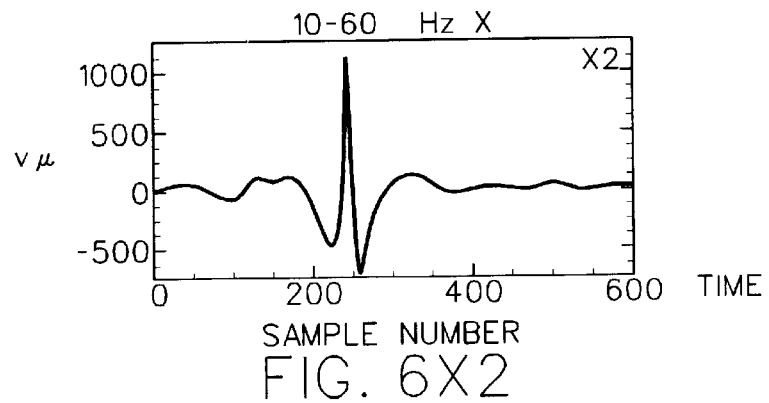
FIG. 6X2
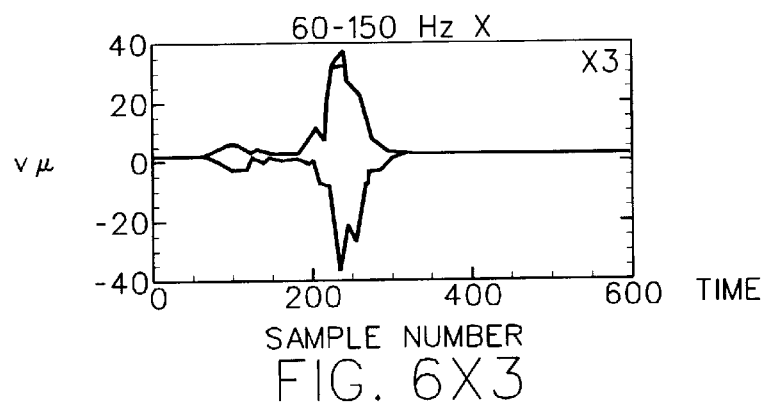
FIG. 6X3
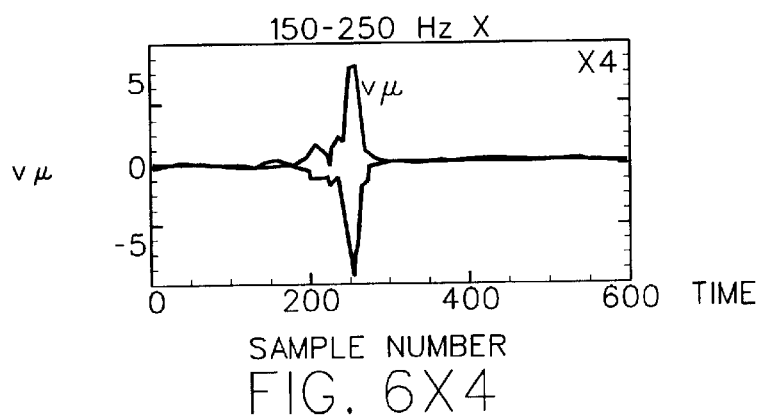
FIG. 6X4

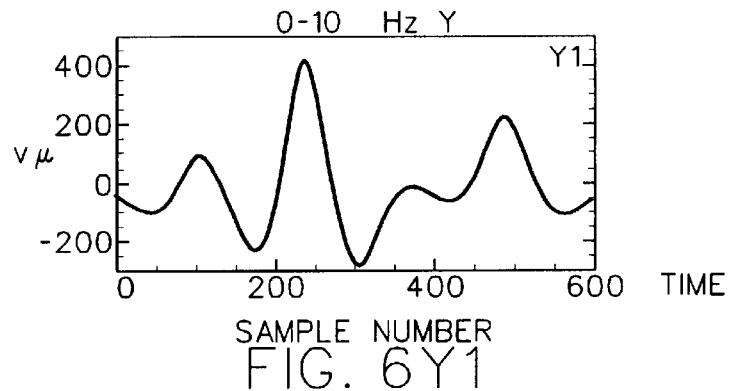
FIG. 6Y1
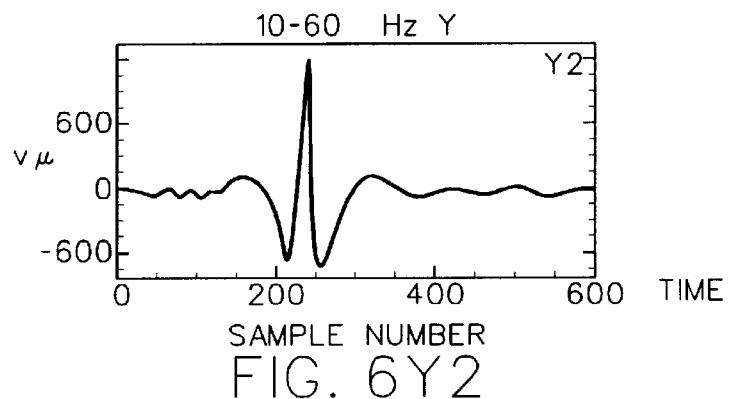
FIG. 6Y2
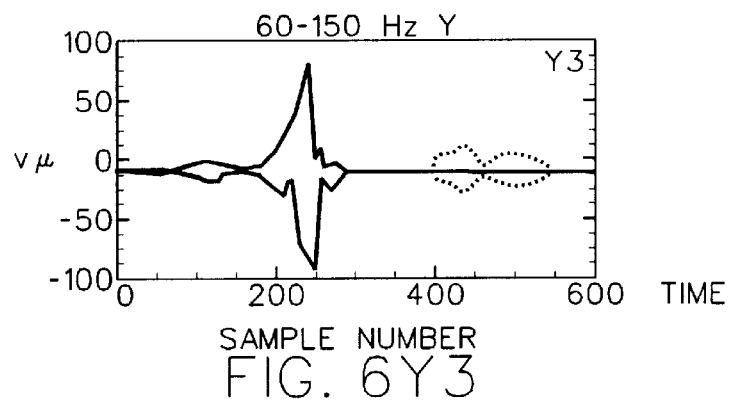
FIG. 6Y3
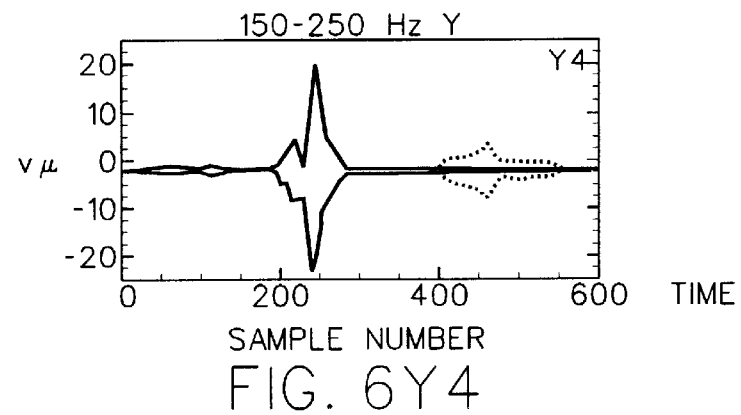
FIG. 6Y4

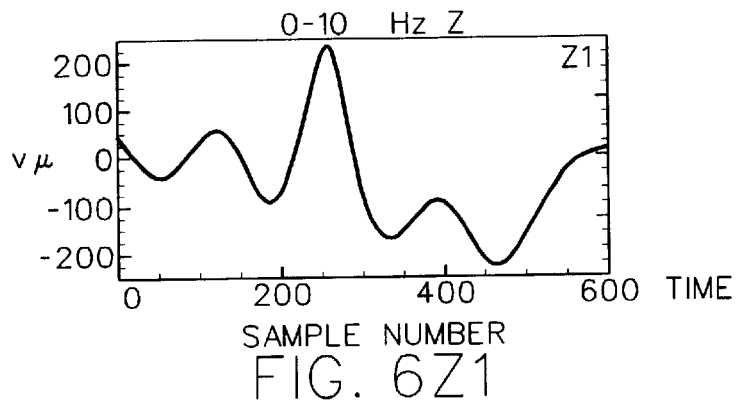
FIG. 6 Z1
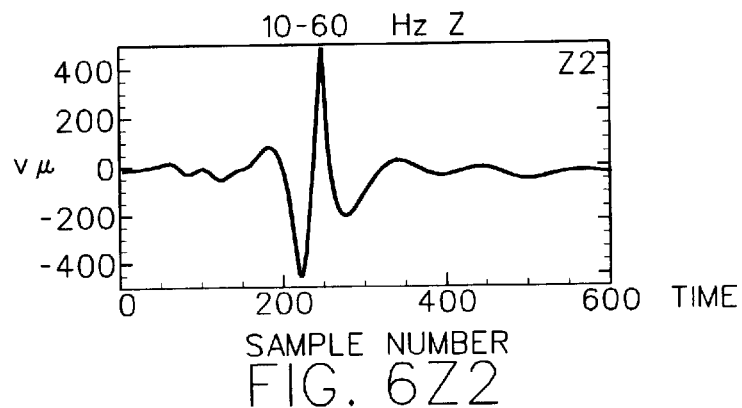
FIG. 6 Z2
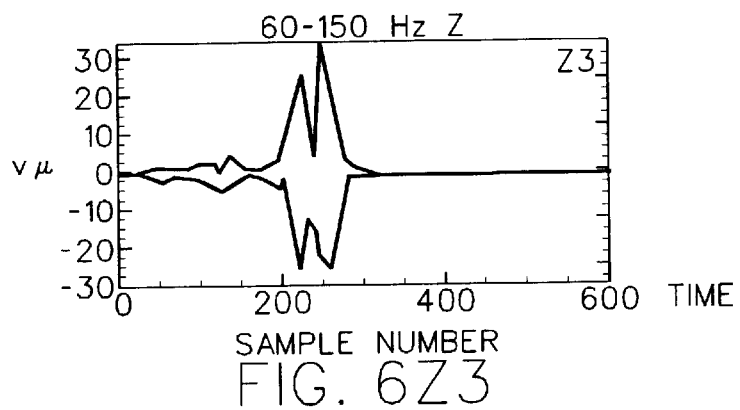
FIG. 6 Z3
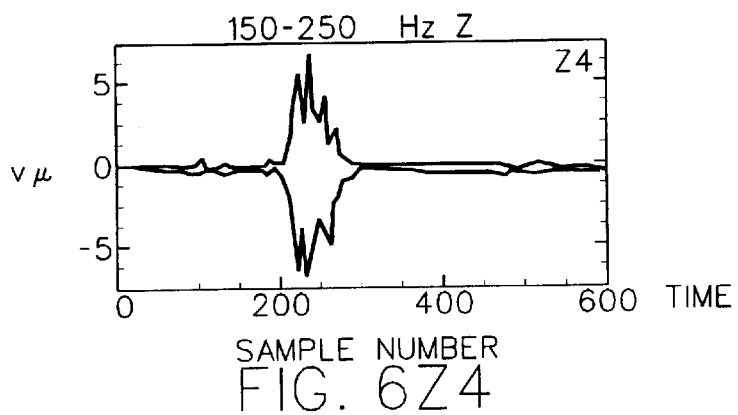
FIG. 6 Z4

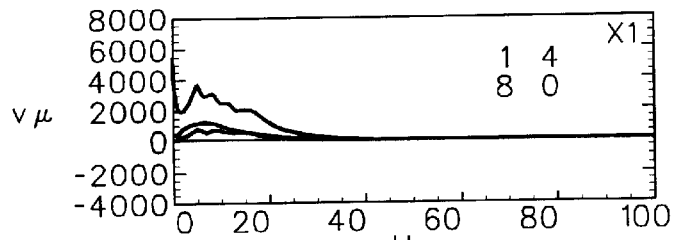
FIG. 7aX1
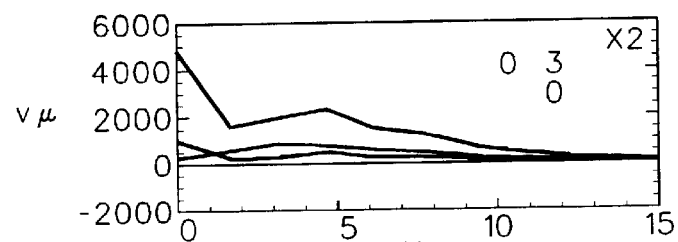
FIG. 7aX2
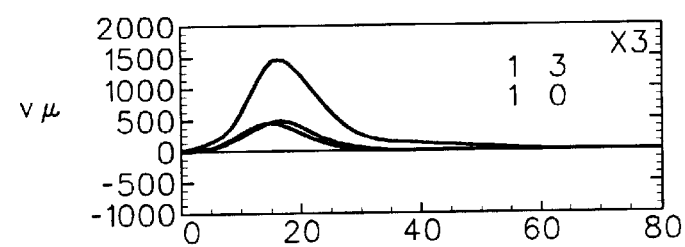
FIG. 7aX3
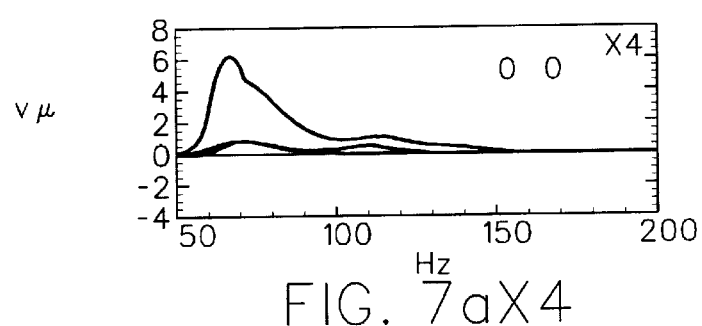
FIG. 7aX4
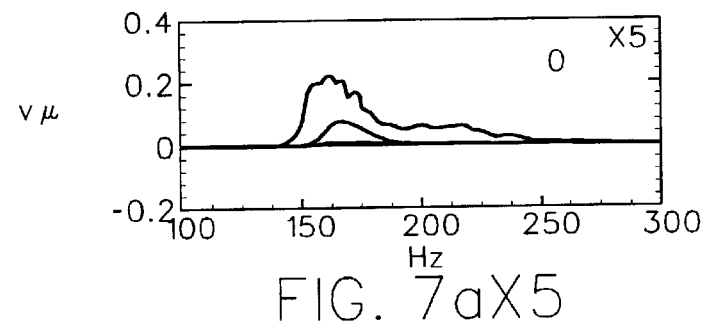
FIG. 7aX5

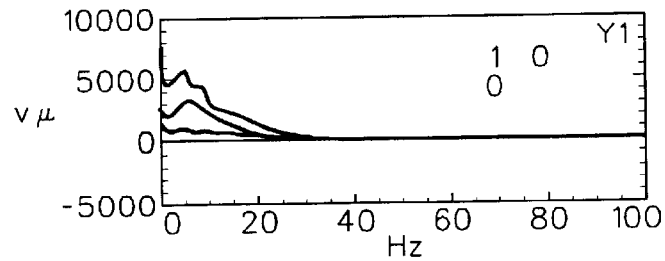
FIG. 7aY1
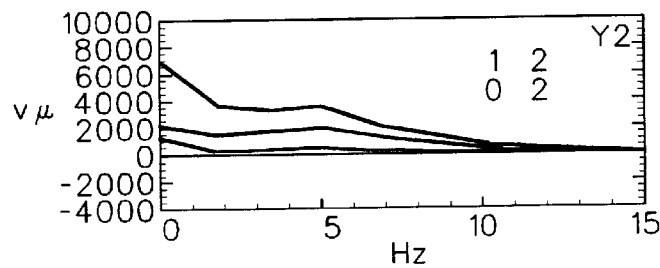
FIG. 7aY2
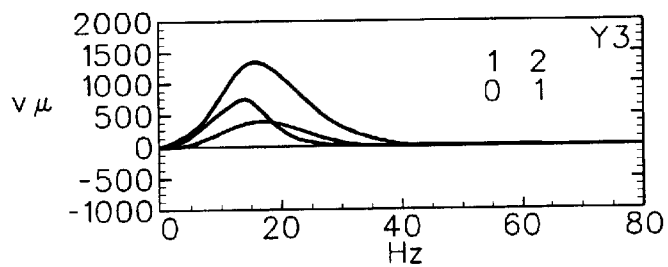
FIG. 7aY3
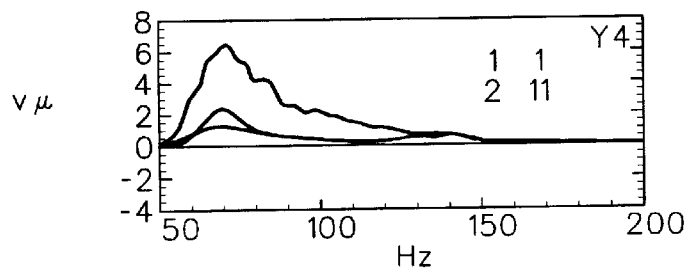
FIG. 7aY4
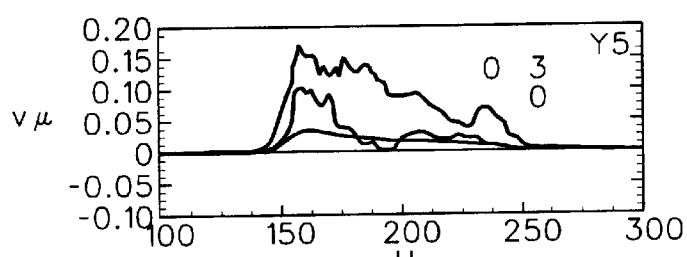
FIG. 7aY5

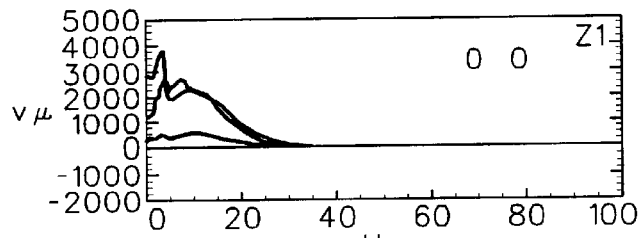
FIG. 7aZ1
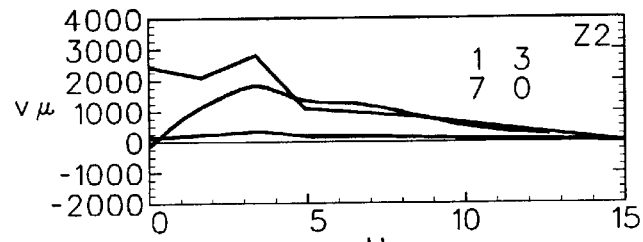
FIG. 7aZ2
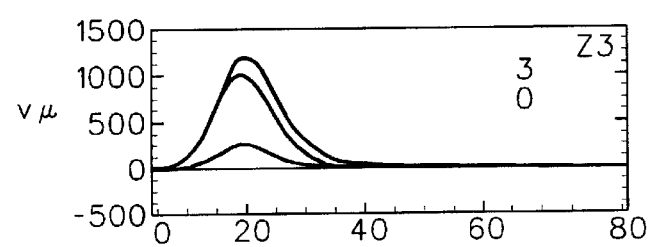
FIG. 7aZ3
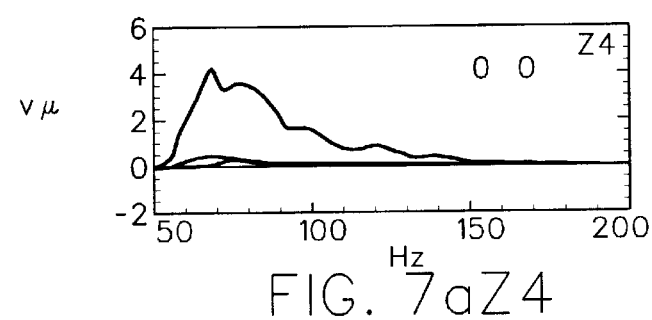
FIG. 7aZ4
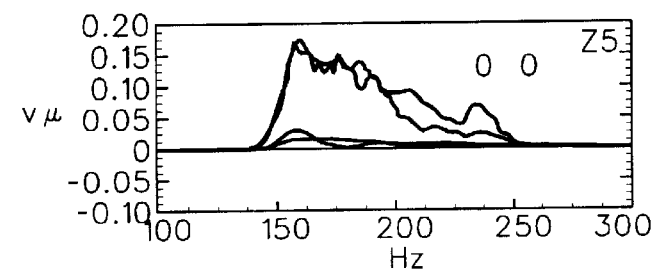
FIG. 7aZ5

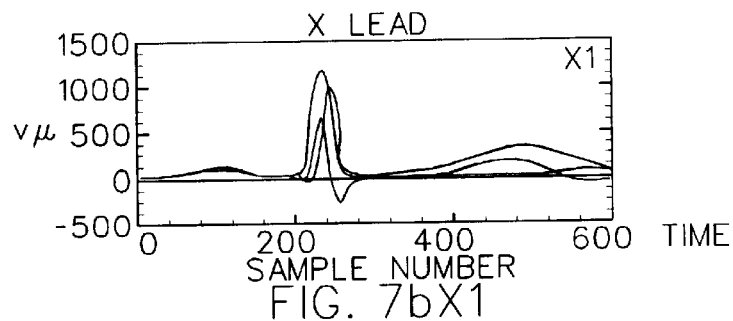
FIG. 7bX1
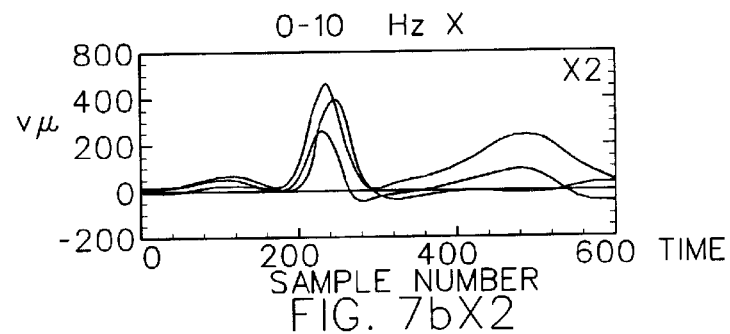
FIG. 7bX2
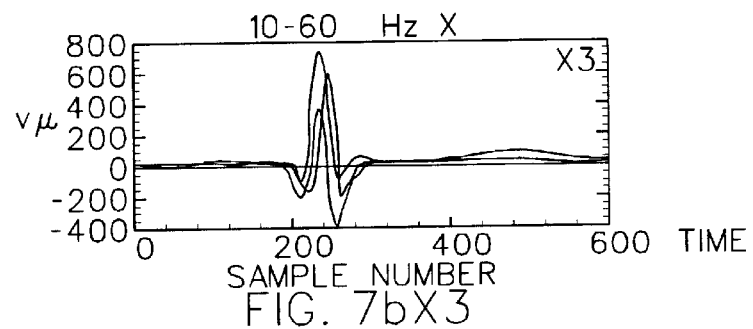
FIG. 7bX3
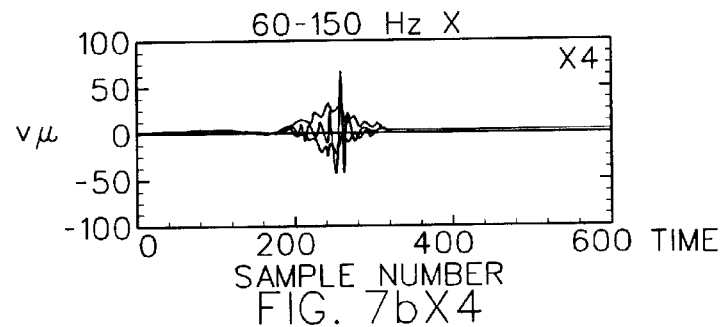
FIG. 7bX4
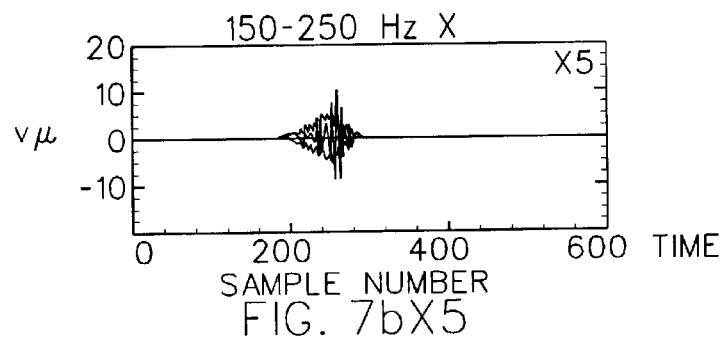
FIG. 7bX5

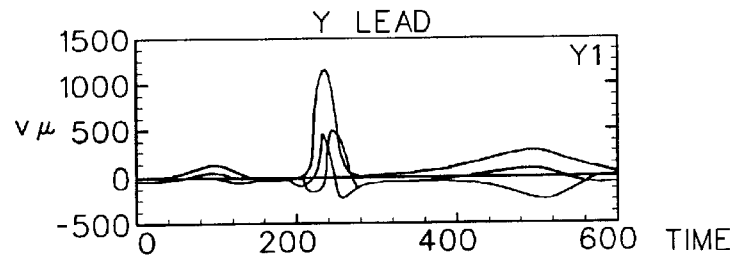
FIG. 7bY1
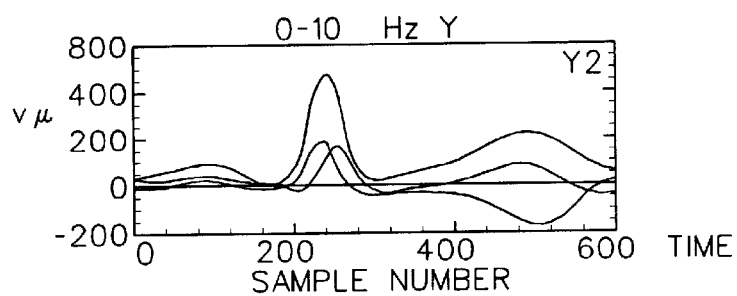
FIG. 7bY2
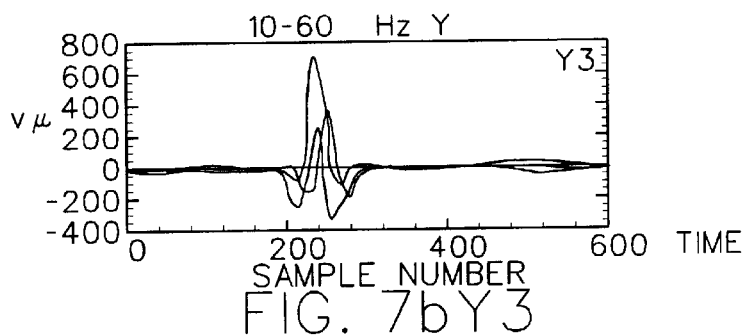
FIG. 7bY3
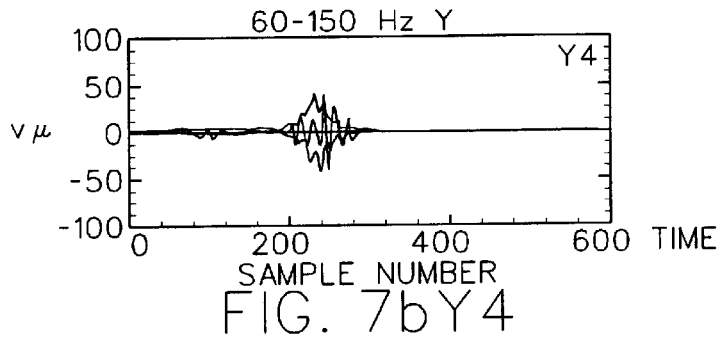
FIG. 7bY4
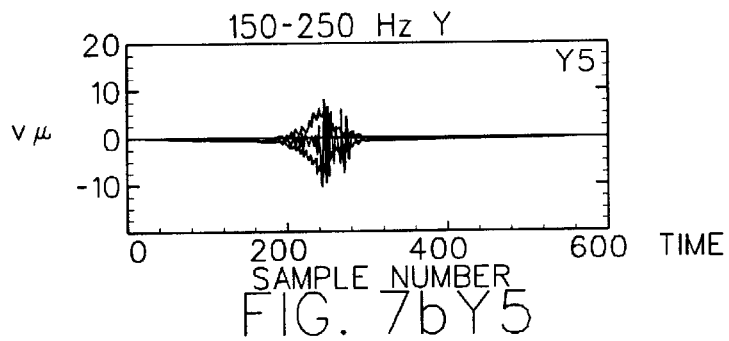
FIG. 7bY5

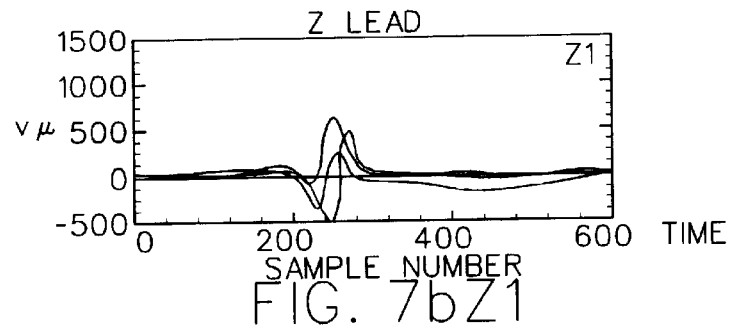
FIG. 7bZ1
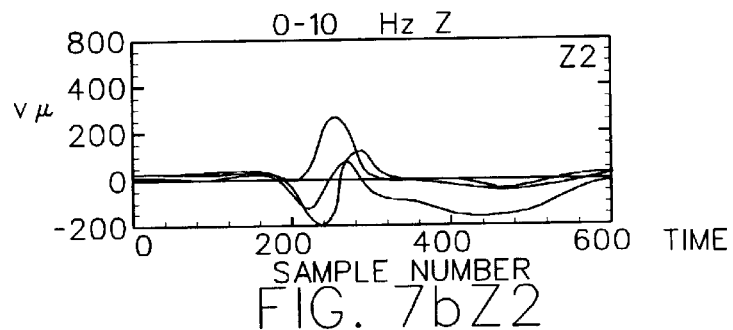
FIG. 7bZ2
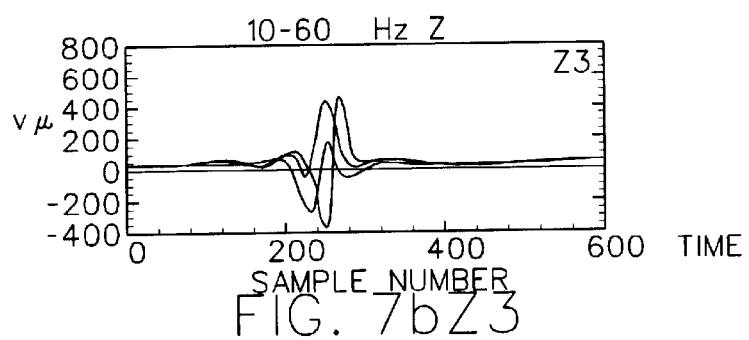
FIG. 7bZ3
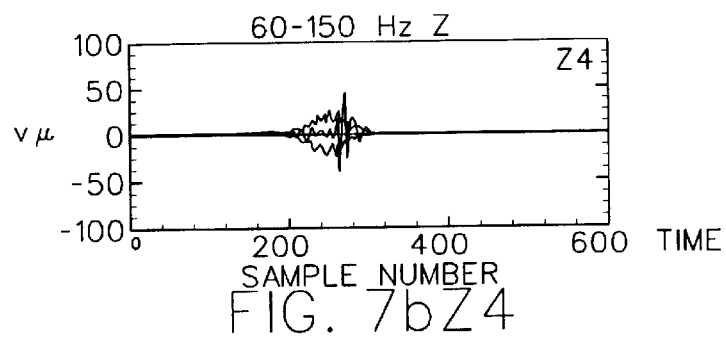
FIG. 7bZ4
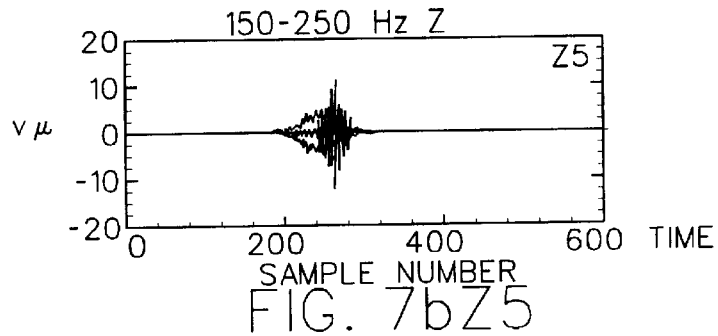
FIG. 7bZ5

A
DETERMINE MEAN AND STANDARD DEVIATION ACCEPTANCE PARAMETERS FOR EACH INITIAL SUBJECT, OR NORMAL SUBJECT POPULATION, REPRESENTATIVE PARAMETER(S) AND/OR INITIAL SUBJECT, OR NORMAL SUBJECT POPULATION RATIOS OF REPRESENTATIVE PARAMETER(S), BASED UPON INITIAL SUBJECT, OR NORMAL SUBJECT POPULATION, ECG DATA IN EACH ECG LEAD AND FREQUENCY BAND, FROM WHICH ECG DATA COMPOSITE ECG CYCLES ARE DETERMINED

B
DETERMINE AN ACCEPTANCE PARAMETER FOR EACH SPECIFIC CORRESPONDING SUBJECT FOLLOW-ON, OR CORRESPONDING SUBJECT, REPRESENTATIVE PARAMETER AND/OR SUBJECT FOLLOW-ON, OR SUBJECT, RATIO OF CORRESPONDING SUBJECT FOLLOW-ON, OR CORRESPONDING SUBJECT, REPRESENTATIVE PARAMETER(S) IN EACH ECG LEAD AND FREQUENCY BAND, FROM WHICH ECG DATA COMPOSITE ECG CYCLES FOR SUBJECT FOLLOW-ON, OR CORRESPONDING SUBJECT ARE DETERMINED

C
ACCEPTING THE RESULTS OF COMPARING A SPECIFIC SUBJECT FOLLOW-ON, OR SUBJECT, REPRESENTATIVE PARAMETER FOR USE IN ARRIVING AT A "SCORE" ONLY IF THE ACCEPTANCE PARAMETER FOR SAID SUBJECT FOLLOW-ON, OR SUBJECT, IS SET-OFF BY AT LEAST ONE INITIAL SUBJECT STANDARD DEVIATION FROM SAID INITIAL SUBJECT, OR NORMAL SUBJECT POPULATION SUBJECT MEAN AND/OR ACCEPTING THE RESULTS OF COMPARING A RATIO OF SPECIFIC SUBJECT FOLLOW-ON, OR SUBJECT, REPRESENTATIVE PARAMETERS FOR USE IN ARRIVING AT A "SCORE" ONLY IF THE ACCEPTANCE PARAMETER FOR SAID RATION OF SUBJECT FOLLOW-ON, OR SUBJECT, REPRESENTATIVE PARAMETERS IS SET-OFF BY AT LEAST ONE INITIAL SUBJECT STANDARD DEVIATION FROM SAID INITIAL SUBJECT, OR NORMAL SUBJECT POPULATION SUBJECT MEAN

FIG. 10c

NONINVASIVE SYSTEM AND METHOD FOR IDENTIFYING CORONARY DISFUNCTION UTILIZING ELECTROCARDIOGRAPHY DERIVED DATA

This is a Continuation-In-Part application based upon a Copending U.S. application Ser. No. 08/418,175 filed Apr. 6, 1995, now U.S. Pat. No. 5,655,540.

TECHNICAL FIELD

The present invention relates to safe noninvasive systems and methods of use thereof for application in identifying coronary disfunction, which methods and systems are suitable for application in investigation of human subjects. More particularly the present invention is primarily a method of processing data derived from application of an electrocardiograph (ECG) system which involves mathematical and statistical techniques, data filtering and windowing, and application of a unique algorithm to the end that highly predictive, easily interpreted numerically precise SEECADtm "Scores" and data patterns are determined.

BACKGROUND

It is generally accepted that approximately one-quarter of North Americans have some degree of Coronary Artery Disease (CAD). It is also generally accepted that approximately half thereof are not reliably detectable by conventionally applied diagnostic techniques, such as noting contour changes in the S-T segments of electrocardiograms (ECG's). The problematic nature the situation poses is perhaps most critically apparent when one considers that perioperative complications can be much more prevalent and serious in a patient with (CAD) than in a normal patient who does not have (CAD). That is, knowledge that a patient has (CAD), or any coronary dysfunction, can be critical in fostering morbidity and mortality reduction procedure planning and scheduling on the part of medical professionals. As well, detection of (CAD) is, of course, important in everyday matters such as the planning and execution of a simple exercise routine.

It is noted that conventional (ECG) analysis provides time domain graphical results based primarily upon the low frequency (eg. 0 to 40 Hz), content of a subject's cardiac signals monitored by an (ECG) system. This is the case whether a Frank orthogonal X-Y-Z; a standard 12 Lead or a multi-Lead monitoring etc. (ECG) system is utilized. For instance, a Patent to Brown et al., U.S. Pat. No. 5,077,667 describes a method for measuring a clinically useful characteristic of a fibrillating heart related to the elapsed time since the onset of ventricular fibrillation. Their significant variable is the power in the frequency range of 7 to 8 Hz. The Brown et al. Patent describes the use of a transformation of sampled analog time domain signals into the frequency domain and subsequent analysis thereof as a step intermediate to applying corrective treatment to a fibrillating heart.

A Patent, U.S. Pat. No. 4,680,708 to Ambos et al., describes the use of a Fast Fourier Transform (FFT) applied to a portion of an (ECG) cycle. Mathematical analysis of the last forty (40) milliseconds of a waveform derived from the time domain (QRS) complex allows for calculation of a Figure Of Merit, (FOM), based upon the frequency content thereof. Said (FOM) is correlated to the likelihood of a patient experiencing ventricular tachycardia. While the Ambos et al. Patent mentions the presence of high frequency components in a signal derived from the (ECG), said Patent primarily focuses upon the analysis of frequencies between 20 and 50 Hertz in arriving at the (FOM). The Ambos et al. Patent further states that "Recent studies . . . have used a variety of low (25 to 100 Hz) and high (250 to 300 Hz) band pass filters. A major limitation . . . is a lack of a-priori knowledge of the frequency distribution of signals of interest and the inherent risk that filtering will exclude signals of particular interest."

Other recent investigation has focused upon the diagnostic capability inherent in the presence of particular high frequency components present in an (ECG) signal. For instance, a very recent paper by Aversano et al., titled "High Frequency QRS Electrocardiography In The Detection Of Reperfusion Following Thrombolytic Therapy", (see Clinical Cardiology, (17, 175–182, April 1994)), states that the amplitude of the high frequency components, (eg. 150–250 Hz), of the (QRS) complexes decreases during cardiac ischemia, and returns to normal with resolution thereof. It is also stated that high frequency electrocardiography is a rapid and reliable bedside technique for discriminating between successful and failed reperfusion in patients treated with thrombolytic agents for myocardial infarction. The Aversano et al. paper also states that "Studies involving high-frequency QRS electrocardiography are few and modest."

A paper by Moss and Benhorin titled "Prognosis and Management After a First Myocardial Infarction", New England J. Medicine, Vol. 322, No. 11, 1990 points out the importance of being able to identify and distinguish patients with various types of (CAD) so that appropriate treatment can be prescribed. This paper, in conclusion acknowledges that noninvasive techniques currently available for detecting jeopardized ischemic myocardium are imperfect.

The above sampling of relevant prior reference materials shows that techniques such as direct morphologic analysis of conventional time domain signals, application of (FFT) to (ECG) time domain derived signals to provide frequency domain spectra for analysis, analysis of high frequency components of (ECG) signals and the focusing on specific portions of a QRS complex etc. are known. There remains, however, need for additional and more probative noninvasive methods of analyzing (ECG) derived data which allow incipient (CAD) in patients to be identified with improved certainty. In particular, there is a need for a method of accurately identifying subjects with (CAD), the validity of which has been shown to provide utility by actual clinical testing.

The present invention provides an improved method of analyzing (ECG) derived data which have as shown by actual test, (in view of an extensive data bank accumulated by the inventor containing both normal and abnormal (ECG) data), to enable greatly improved ability to accurately and noninvasively separate abnormal from normal cardiac subjects. The method of the present invention, for instance, routinely allows identification of subjects with truely silent (CAD), and subjects who do not present with the tell-tale classic QRST and T wave changes. The method of the present invention also routinely allows identification of subjects with nonspecific S-T and T wave changes, and allows identification and separate classification of subjects with prior myocardial infarction, abnormal patients who present with normal (ECG), and simultaneously distinguishes the population of abnormal subjects who present with normal (ECG). The present invention also allows identification of subjects who are at risk for sudden death.

DISCLOSURE OF THE INVENTION

The present invention, in its presently preferred embodiment, utilizes a Frank orthogonal X-Y-Z Lead electocardiograph (ECG) system, but is primarily a method of analyzing and categorizing individual subject electrocardiogram (ECG) data. Said method has been shown to be capable of identifying and classifying subjects into cardiac categories such as:

1. Normal, and
2. Abnormal:
   a. Presents with prior myocardial infarction,
   b. Presents with nonspecific S-T and T wave changes,
   c. Presents with normal (ECG) but known otherwise to be abnormal.

(Note, continued efforts are serving to greatly increase the specific classification capabilities of the present invention, and are even extending it to identification of specific anatomic abnornormality locations), (eg. myocardium, cardiac artery etc), which cause said specific abnormality).

As a starting point the present invention requires a substantial data base from which (ECG) data attributable to a "normal" population can be derived and used to form a "template" against which unknown subject (ECG's) can be compared. The present invention provides that by application of a discriminant Algorithm, (see supra), these unknown subjects may be appropriately classified. In the presently preferred embodiment of the present invention such a data base was developed by selection and testing of fit and healthy, relatively young subjects from families with a low prevalence of, and low risk factors for, coronary artery disease (CAD). Suitable subjects were required to fill out a questionnaire, analysis of which aided in determination of subject suitability as a "normal". A total of two-hundred-fifty (250) normal subjects were identified and (ECG) data obtained from each thereof. A random sampling of data from one-hundred-forty (146) subjects from said group of two-hundred-fifty (250) normals was assembled and analyzed to provide relevant, (see supra), composite root-mean-square, (RMS), mean and standard deviation values.

To arrive at said relevant normal RMS mean and RMS standard deviation values, (ECG) signals for each normal were derived by acquiring a number of, (typically one-hundred (100)), full (ECG) cycles, (ie. full PQRST (ECG) cycles), for each normal subject, sampling each full cycle to provide six-hundred (600) data points over the extent thereof, and then selecting out the corresponding data points in each QRS complex in each of said full PQRST cardiac cycles. A single averaged (ECG) cardiac cycle was mathematically constructed from said number of QRS complexes and RMS mean and RMS standard deviation values calculated therefore.

In addition, similar RMS means and RMS standard deviation values were obtained from the same data, but which data had been subjected to digital filtering employing a Blackman-Harris window. The results are identified in the following table for each of the three Frank orthogonal (ECG) X-Y-Z system lead signals:

| FREQUENCY RANGE | DATA PROVIDED | |
|---|---|---|
| FOR FRANK (ECG) SYSTEM LEAD X, (HORIZONTAL AXIS): | | |
| (FULL-ALL FREQUENCIES) | RMS MEAN | RMS SD |
| ((0) TO (10) HZ) | RMS MEAN | RMS SD |
| ((10) TO (60) HZ) | RMS MEAN | RMS SD |
| ((60) TO (150) HZ) | RMS MEAN | RMS SD |
| ((150) TO (250) HZ) | RMS MEAN | RMS SD |
| FOR FRANK (ECG) SYSTEM LEAD Y, (VERTICAL AXIS): | | |

-continued

| FREQUENCY RANGE | DATA PROVIDED | |
|---|---|---|
| (FULL-ALL FREQUENCIES) | RMS MEAN | RMS SD |
| ((0) TO (10) HZ) | RMS MEAN | RMS SD |
| ((10) TO (60) HZ) | RMS MEAN | RMS SD |
| ((60) TO (150) HZ) | RMS MEAN | RMS SD |
| ((150) TO (250) HZ) | RMS MEAN | RMS SD |
| FOR FRANK (ECG) SYSTEM LEAD Z, FRONT TO BACK AXIS): | | |
| (FULL-ALL FREQUENCIES) | RMS MEAN | RMS SD |
| ((0) TO (10) HZ) | RMS MEAN | RMS SD |
| ((10) TO (60) HZ) | RMS MEAN | RMS SD |
| ((60) TO (150) HZ) | RMS MEAN | RMS SD |
| ((150) TO (250) HZ) | RMS MEAN | RMS SD | where SD stands for Standard Deviation.

TABLE D-1

EACH TABULAR CATEGORY IS PROVIDED AN RMS MEAN AND STANDARD DEVIATION

| FREQUENCY (HZ) | LEAD X | LEAD Y | LEAD Z |
|---|---|---|---|
| TOTAL SIGNAL | | | |
| 0–INFINITE Hz | | | |
| 0–10 Hz | | | |
| 10–60 Hz | | | |
| 60–150 Hz | | | |
| 150–250 Hz | | | |

Said resulting normal RMS mean and RMS standard deviation values for each of the frequency ranges and utilized Frank (ECG) system X-Y-Z lead serve to define assumed Gaussian "templates" for normals, against which similarly derived RMS means, acquired from individual subjects, are compared under the guidelines of the Algorithmic Method of the present invention, (see supra).

To date data from more than one-thousand (1000) abnormal subjects has been assembled by the inventor, and subject RMS mean values derived therefrom. It is noted that abnormal subjects tested provide representatives from each the three abnormal groups identified infra.

Continuing, to apply the Algorithm Method of the present invention many, (typically one-hundred (100)), of human subject derived full PQRST (ECG) cardiac cycles are obtained. Said full (ECG) cardiac cycles are each then sampled to provide six-hundred data points over the extent thereof and the sampled data points corresponding to the QRS complex in each full cycle are mathematically averaged to provide a composite QRS complex. As well, the digital filtering and application of the Blackman-Harris Window to allow calculation of the RMS means which correspond to each frequency range and Frank (ECG) system X-Y-Z lead utilized, are performed. The end result can be expressed as a table of data, (not shown), similar to the table presented above for the normal data but which contains only composite RMS mean values.

The Algorithm employed in the method of the present invention embodiment then provides for a maximum of thirty (30) calculations to be performed as follows:

a. Up to Fifteen of said calculations involve calculating the difference between the subject composite RMS mean and the corresponding normal composite RMS mean, and dividing the result by the corresponding normal RMS standard deviation, for each Frank X-Y-Z (ECG) lead and each frequency range band, (ie. the fifteen calculations break down as five (5) frequency range bands per each of the Frank X-Y-Z (ECG) leads.)

b. Twelve of said calculations involve finding the RMS ratio for each frequency range band, (eg. 0–10 Hz, 10–60 Hz, 60–150 Hz and 150–250 Hz) to the total sum of all said frequency band RMS contributions for each appropriate said Frank (ECG) X-Y-Z lead, for a subject, and subtracting therefrom equivalent RMS ratio mean results derived based upon the same calculations as applied to normal data, and dividing the result by the RMS standard deviation for the corresponding frequency range, of said normal data.

c. Three of said calculations involve calculating the difference between ratios of the subject composite RMS means of Frank lead X/Y, Y/Z and X/Z ratios and the corresponding RMS means of normal X/Y, Y/Z and X/Z ratios and dividing by the RMS value of the normal RMS standard deviations of said ratios.

Each of the above identified thirty (30) calculations will result in a number (Pi). A "Score" component number (Si) is then derived based upon where a (Pi) number lies in an assumed Gaussian Distribution. This is calculated based upon normal data RMS Means and RMS Standard Deviations (X) as follows:

If $-1\times<Pi<1\times$ then $Si=0$,

If $-2\times<Pi<-1\times$ or $1\times<Pi<2\times$ then $Si=1$,

If $-3\times<Pi<-2\times$ or $2\times<Pi<3\times$ then $Si=2$,

If $-4\times<Pi<-3\times$ or $3\times<Pi<4\times$ then $Si=3$ etc.

Each of the resulting subject RMS mean values associated with a calculated Si value is then analyzed to determine if it is greater than or equal to ninety-five (95%) percent of the data points from which the normal RMS mean was calculated. If this is the case the associated Si is accepted. Otherwise it is rejected. That is, a ninety-five (95%) confidence interval, based upon normal data spread, is imposed, in determining whether to accept a calculated (SI) value.

Accepted values are then selected and added together to provide a final numerical "Score". (Note, two Scores in the catagory a. above are commonly not selected as being redundant to other Scores. Said commonly unselected Scores are better identified in the Detailed Description Section).

(Note that the truncation involved in obtaining an Si value can be eliminated and the Pi Score utilized in determining said final numerical "Score").

In either approach to "Score" calculation it has been found that if said final numerical "Score" is "low"(eq. approximately 0 to 7) then the subject is more likely to be normal. If the final numerical "Score" is high (eg. greater than about 8), then the subject is more likely to be abnormal. For instance, a "Score" of 7 provides a ninety (90%) percent confidence of normality, and a "Score" of 8.4 provides a ninety-five (95%) confidence of normality, (See FIG. 9).

As will be better presented in the Detailed Description Section of this Disclosure, the results of the application of the method of the present invention as described above can be presented in numerous ways. A particularly relevant approach is to present the results on a graph of ("Sensitivity"vs. "100-Specificity"). (The present invention provides that the "Score" value be plotted against the abscissa (100-Specificity) and that percentage of a group having said "Score" be plotted on the (Sensitivity) ordinate). Said approach to presentation is generally known as an ROC curve, (ROC stands for Receiver Operation Characteristic as the technique was originally derived for use in testing radio receiver quality). Said approach to presentation serves to visually demonstrate the success of the present invention method of analyzing (ECG) derived data. In particular, abnormal subjects which can not be identified by conventional (ECG) analysis techniques, are seen to be easily identified by application of the present invention algorithm.

In addition, the present invention provides that time domain data obtained from Frank X-Y-Z (ECG) leads should be subjected to a Fourier Transform and manipulated to provide Power Spectral Density (PDS) vs. Frequency plots. As will also be better presented in the Detailed Description Section of this Disclosure, said (PDS) plots are typically easier than associated (ECG) data vs. time plots to visually interpret. Said plots complement the above described "Scoring" system approach to identifying coronary disfunction.

It should also be appreciated that if an initial patient specific data base is accumulated, it can serve as a baseline data base and be utilized as a replacement for the normal subject population data base. At later times, additional patient specific data can then be obtained, and compared to the patient baseline data base, in a tracking scenario.

It has further been found that, if dividing a "Score" for a patient as provided by practice of the present invention, by the ejection fraction of the patient, (as obtained by radionuclide imaging or other accurate technique), provides a result greater than one (1.0) then the subject patient involved is at high risk of sudden death. In addition, it has been found that if the S-T segment following a QRS complex has "Rhomboids" present therein, (eg. electrical signal activity on the order of three (3) standard deviations from a baseline signal, particulary in Time Domain plots in 60–150 and/or 150–250 Hz band(s)), then the patient involved is at high risk of sudden death. The present invention methodology can include as steps inclusion of said criteria.

A system for practicing the present invention method comprises (ECG) signal monitoring electrode means, (perhaps preferably such as described in an Allowed U.S. Patent to Stratbucker, Ser. No. 434,658 which claims a Bioelectric Interface with all necessary (ECG) Chest Mounted Electrodes present in a common electrode separation maintaining support material), and any necessary interface such that data monitored by said (ECG) electrodes is fed to a memory device, and possibly means for determining ejection fraction. In addition, computational means for performing necessary calculations and displaying results, and necessary interconnection and interfacing means are required. It should be appreciated that a system for practicing the present invention method can be fashioned from essentially any computer system with sufficient memory means and computational capability means, and it is the configuration thereof to carry out the method of the present invention which distinguishes said system over computer systems in general, rather than any specific system elements.

BRIEF DESCRIPTION OF THE DRAWINGS

FIG. 1a shows a representation of a human torso with Frank X and Y (ECG) system leads attached thereto.

FIG. 1b shows a cross section taken at a—a in FIG. 1a, with Frank Z (ECG) system leads attached thereto.

FIG. 2 shows a demonstrative "PQRST" (ECG) waveform.

FIG. 3 demonstrates a table for recording data necessary for practice of the present invention.

FIGS. 6X1, 6X2, 6X3, 6X4, 6Y1, 6Y2, 6Y3, 6Y4, 6Z1, 6Z2, 6Z3, 6Z4), show twelve related plots of subject time domain sample data recorded from Frank X-Y and Z (ECG) system leads for a plurality of frequency range bands. Higher frequency frequency bands are presented as one progresses from FIG. 6X1 to 6X4, and from 6Y1 to 6Y4 and from 6Z1 to 6Z4.

FIGS. 7aX1, 7aX2, 7aX3, 7aX4, 7aX5, 7aY1, 7aY2, 7aY3, 7aY4, 7aY5, 7aZ1, 7aZ2, 7aZ3, 7aZ4, 7aZ5, show fifteen related plots of subject frequency domain power spectral density. Shown in (7aX1, 7aY1 and 7aZ1 are transforms of full frequency band requisite data. Transforms of data from progressively higher frequency frequency bands are presented as one progresses from FIG. 7aX1 to 7aX5, from 7aY1 to 7aY5 and from 7aZ1 to 7aZ5.

FIGS. 7bX1, 7bX2, 7bX3, 7bX4, 7bX5, 7bY1, 7bY2, 7bY3, 7bY4, 7bY5, 7bZ1, 7bZ2, 7bZ3, 7bZ4, 7bZ5, show fifteen plots of related subject time domain data. Shown in (7bX1, 7bY1 and 7bZ1) are full frequency band requisite data. Data from higher frequency frequency bands are presented as one progresses progresses from FIG. 7BX1 to 7aY5, from 7aY1 to 7aY5 and from 7aZ1 to 7aZ5.

FIGS. 10a, 10b, 10c, and 10d are flow charts showing aspects and modifications of present invention method.

DETAILED DESCRIPTION

Figure 4:
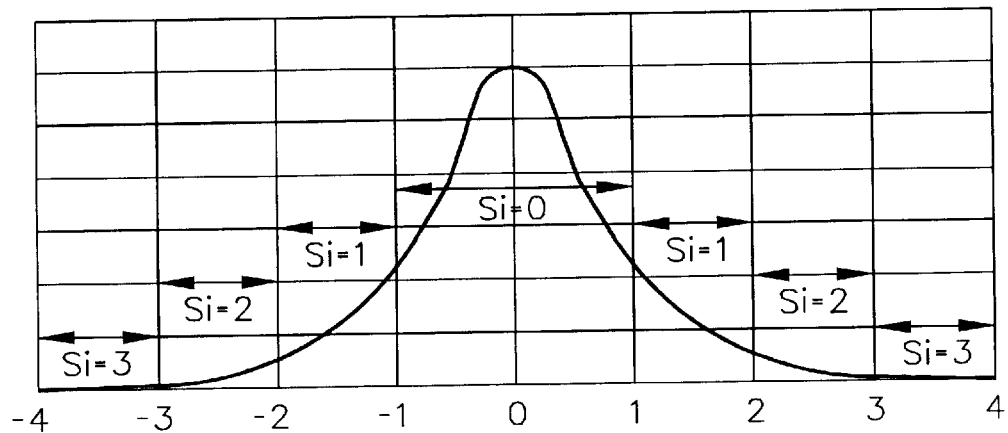
FIG. 4 shows an assumed gaussian distribution for use in assigning "Score" component numbers during practice of the present algorithm.

In the following a specific embodiment of the present invention is presented. Said specific embodiment assumes the use of an (ECG) system which utilizes Frank (ECG) orthogonal X-Y-Z leads. It is to be understood, however, that the present invention is not limited to such and can be practiced with (ECG) systems in which any number of leads, (eg. standard twelve (12), sixteen (16), or mapping arrays of twenty-four (24) or more etc.), are present, and in which only some of the present leads are utilized.

The following specific embodiment is presented as it is well documented and is presently the preferred embodiment.

Turning now to the drawings, there is shown in FIG. 1(a) a frontal view of a torso of a human, with (ECG) Frank X and Y leads properly affixed thereto. FIG. 1(b) shows a cross section taken at a—a in FIG. 1(a) with (ECG) Frank Z leads properly attached thereto. In use said (ECG) Frank X-Y-Z leads are attached to an (ECG) system and serve to effect orthogonal monitoring of (ECG) full cardiac cycle PQRST signals which are essentially shaped as shown in FIG. 2.

The present invention requires as a starting point that a significant data base be available, which significant data base contains representative composite (ECG) data for all, or some portion of full (ECG) PQRST cycles for each (ECG) lead, for a normal population. (Note, a normal population is defined as one in which the subjects have no detectable coronary artery disease (CAD) by history and multiple conventional diagnostic tests, and are not at risk therefore based upon age, family history etc.) Such a significant data base for normals was acquired by obtaining a number of full (ECG) PQRST cycles from each of the Frank X-Y-Z (ECG) leads present in the presently discussed embodiment of the invention, from each of two-hundred-fifty (250) normals. (It is noted that the present invention is not limited to cases in which all leads present in an (ECG) system are monitored but that a preferred embodiment does utilize all available information). Next, a random sample of one-hundred-forty-six (146) of said two-hundred-fifty (250) normals was selected and a representative number of the full (ECG) PQRST cycles from each, (typically one-hundred (100)), for each Frank X-Y-Z (ECG) lead, were then selected and each subjected to a sampling procedure which provided some number of data points for each, (six-hundred (600) was chosen in the presently discussed embodiment). Next, the sampled data points corresponding to the QRS depolarization complexes in each selected full (ECG) PQRST cycle were selected and a representative composite QRS complex for each Frank (ECG) X-Y and Z leads formed therefrom by mathematical averaging thereof. Said representative composite was then subjected to filtering and windowing techniques to provide a number of data sets for each of the Frank (ECG) X-Y-Z leads. Said data sets in the presently preferred embodiment of the present invention provide information present in said representative composite in the frequency bands:

a. All frequencies;
b. Between zero (0) and ten (10) Hz;
C. Between ten (10) and sixty (60) Hz;
d. Between sixty (60) and
e. Between one-hundred-fifty (150) and two-hundred-fifty (250) Hz.

For each of the Frank (ECG) X-Y-Z leads then, five (5) sets of data were derived as described, and from each of said sets of data a Root-Mean-Square (RMS) mean and (RMS) standard deviation were calculated. This, it will be appreciated, resulted in fifteen (15) RMS representative composite means and standard deviations being available, (five for each Frank (ECG) X-Y-Z lead).

In view of the described RMS mean and RMS standard deviations (SD's) available clinical application of the present invention can be practiced.

To practice the present invention, data are obtained from a subject in a manner essentially the same as described infra for normals. That is, a number of full (ECG) PQRST full cardiac cycles from each Frank (ECG) X-Y-Z lead are obtained and a representative number thereof are selected and subjected to a sampling procedure. Some portion of each full PQRST waveform is selected, (eg. the QRS depolarization complex is utilized in the presently preferred embodiment of the present invention), and a representative composite thereof formed therefrom for each Frank (ECG) system X-Y-Z lead. For each representative composite a RMS mean is then calculated so that a table equivalent to that shown in FIG. 3, but containing subject RMS mean data, is formed.

With the described normal RMS mean and RMS standard deviation data, and subject RMS mean data then available, the algorithm of the method of the present invention can be applied to arrive at a diagnostic mathematical "Score".

The algorithm of the present invention involves mathematical comparison of:

a. Normal and subject RMS means in view of normal RMS standard deviation;
b. Ratios of normal and subject RNS frequency range and means to the summation of RMS means for all Frequency range bands for each Frank (ECG) X-Y-Z lead in view of normal standard deviation for the numerator frequency band.
c. Ratios of normal and subject Frank (ECG) X-Y-Z lead RMS means in view of normal standard deviations of said ratios.

Briefly, application of each of the identified steps provides a numerical result (Pi), which in general is typically not a whole integer. The next step is to process said numerical result (Pi) by comparison to an assumed Gaussian Distribution derived from the normal population data to arrive at a whole number integer which represents how many RMS standard deviations the subject RMS mean is away from the normal RMS mean, and assign a whole integer "Score" component number (Si) based thereupon. The algorithm then requires that a ninety-five (95%) confidence interval, based upon normal RMS standard deviation data be applied to determine if a "Score" component should be accepted and included in calculation of a final "Score", said final "Score" being arrived at by an addition of accepted "Score" components. Said algorithm will now be described in detail.

The first step in applying the algorithm of the presently described presently preferred embodiment of the present invention is perform up to fifteen (15) calculations comprising subtracting the Subject RMS mean from a corresponding Normal RMS mean and dividing the result by a corresponding normal RMS standard deviation for each Frank (ECG) X-Y-Z lead in each frequency range identified infra, to provide numbers (Pi).

(Note, the accompany computer printout page labeled "avgasc" provides the various RMS Means and Standard Deviations referred to in the following, corresponding to the P1–P30 number.)

For the Frank (ECG) X lead, (IE. HORIZONTAL AXIS)
For all frequencies:

$$\frac{(\text{Subject RMS mean} - \text{Normal RMS mean})}{\text{Normal RMS Standard Deviation}} = PX1 = P1$$

For the frequency range band zero (0) to ten (10 Hz):

$$\frac{(\text{Subject RMS mean} - \text{Normal RMS mean})}{\text{Normal RMS Standard Deviation}} = PX2 = P2$$

For the frequency range band ten (10) to sixty (60 Hz):

$$\frac{(\text{Subject RMS mean} - \text{Normal RMS mean})}{\text{Normal RMS Standard Deviation}} = PX3 = P3$$

For the frequency range band sixty (60) to ne-hundred-fifty (150 Hz):

$$\frac{(\text{Subject RMS mean} - \text{Normal RMS mean})}{\text{Normal RMS Standard Deviation}} = PX4 = P4$$

For the frequency range band one-hundred-fifty (150 Hz) to two-hundred-fifty (250 Hz):

$$\frac{(\text{Subject RMS mean} - \text{Normal RMS mean})}{\text{Normal RMS Standard Deviation}} = PX5 = P5$$

For the Frank (ECG) Y lead, (IE. VERTICAL AXIS)
For all frequencies:

$$\frac{(\text{Subject RMS mean} - \text{Normal RMS mean})}{\text{Normal RMS Standard Deviation}} = PY1 = P6$$

For the frequency range band zero (0) to ten (10 Hz):

$$\frac{(\text{Subject RMS mean} - \text{Normal RMS mean})}{\text{Normal RMS Standard Deviation}} = PY2 = P7$$

For the frequency range band ten (10) to sixty (60 Hz):

$$\frac{(\text{Subject RMS mean} - \text{Normal RMS mean})}{\text{Normal RMS Standard Deviation}} = PY3 = P8$$

For the frequency range band sixty (60) to one-hundred-fifty (150 Hz):

$$\frac{(\text{Subject RMS mean} - \text{Normal RMS mean})}{\text{Normal RMS Standard Deviation}} = PY4 = P9$$

For the frequency range band one-hundred-fifty (150 Hz) to two-hundred-fifty (250 Hz):

$$\frac{(\text{Subject RMS mean} - \text{Normal RMS mean})}{\text{Normal RMS Standard Deviation}} = PY5 = P10$$

For the Frank (ECG) Z lead. (IE. FRONT TO BACK AXIS)
For all frequencies:

$$\frac{(\text{Subject RMS mean} - \text{Normal RMS mean})}{\text{Normal RMS Standard Deviation}} = PZ1 = P11$$

For the frequency range band zero (0) to ten (10 Hz):

$$\frac{(\text{Subject RMS mean} - \text{Normal RMS mean})}{\text{Normal RMS Standard Deviation}} = PZ2 = P12$$

For the frequency range band ten (10) to sixty (60 Hz):

$$\frac{(\text{Subject RMS mean} - \text{Normal RMS mean})}{\text{Normal RMS Standard Deviation}} = PZ3 = P13$$

For the frequency range band sixty (60) to one-hundred-fifty (150 Hz):

$$\frac{(\text{Subject RMS mean} - \text{Normal RMS mean})}{\text{Normal RMS Standard Deviation}} = PZ4 = P14$$

For the frequency range band one-hundred-fifty (150 Hz) to two-hundred-fifty (250 Hz):

$$\frac{(\text{Subject RMS mean} - \text{Normal RMS mean})}{\text{Normal RMS Standard Deviation}} = PZ5 = P15$$

Twelve (12) additional groups of calculations are then performed in which the relative RMS mean content of each frequency range band identified infra is determined as a percentage of the RMS means of the sum of the filter derived frequency range bands for each Frank (ECG) system X-Y-Z system lead, for both Subject and Normal data, the differences therebetween being divided by the corresponding normal RMS Standard Deviation to provide additional numbers (Pi):

For Frank (ECG) X lead. (IE. HORIZONTAL AXIS

Define:

$$\frac{(100 \times \text{Subject RMS } (0\text{--}10 \text{ Hz}) \text{ mean})}{(\text{Subject RMS mean } (0\text{--}10 \text{ Hz}) + (10\text{--}60 \text{ Hz}) + (60\text{--}150 \text{ Hz}) + (150\text{--}250 \text{ Hz}))} = SX0$$

$$\frac{(100 \times \text{Normal RMS } (0\text{--}10 \text{ Hz}) \text{ mean})}{(\text{Normal RMS mean } (0\text{--}10 \text{ Hz}) + (10\text{--}60 \text{ Hz}) + (60\text{--}150 \text{ Hz}) + (150\text{--}250 \text{ Hz}))} = NX0$$

Normal RMS Standard Deviation (0–10 Hz) = NXSD0

Then:

$$\frac{SX0 - NX0}{NXSD0} = PX6 = P16$$

Define:

$$\frac{(100 \times \text{Subject RMS } (10\text{--}60 \text{ Hz}) \text{ mean})}{(\text{Subject RMS mean } (0\text{--}10\text{Hz}) + (10\text{--}60 \text{ Hz}) + (60\text{--}150 \text{ Hz}) + (150\text{--}250 \text{ Hz}))} = SX1$$

$$\frac{(100 \times \text{Normal RMS } (10\text{--}60 \text{ Hz}) \text{ mean})}{(\text{Normal RMS mean } (0\text{--}10 \text{ Hz}) + (10\text{--}60 \text{ Hz}) + (60\text{--}150 \text{ Hz}) + (150\text{--}250 \text{ Hz}))} = NX1$$

Normal RMS Standard Deviation (10–60 Hz) = NXSD1

Then:

$$\frac{SX1 - NX1}{NXSD1} = PX7 = P17$$

Define:

$$\frac{(100 \times \text{Subject RMS } (60\text{--}150 \text{ Hz}) \text{ mean})}{(\text{Subject RMS mean } (0\text{--}10 \text{ Hz}) + (10\text{--}60 \text{ Hz}) + (60\text{--}150 \text{ Hz}) + (150\text{--}250 \text{ Hz}))} = SX2$$

$$\frac{(100 \times \text{Normal RMS } (60\text{--}150 \text{ Hz}) \text{ mean})}{(\text{Normal RMS mean } (0\text{--}10 \text{ Hz}) + (10\text{--}60 \text{ Hz}) + (60\text{--}150 \text{ Hz}) + (150\text{--}250 \text{ Hz}))} = NX2$$

Normal RMS Standard Deviation (60–150 Hz) = NXSD2

Then:

$$\frac{SX2 - NX2}{NXSD2} = PX8 = P18$$

Define:

$$\frac{(100 \times \text{Subject RMS } (150\text{--}250 \text{ Hz}) \text{ mean})}{(\text{Subject RMS mean } (0\text{--}10 \text{ Hz}) + (10\text{--}60 \text{ Hz}) + (60\text{--}150 \text{ Hz}) + (150\text{--}250 \text{ Hz}))} = SX3$$

$$\frac{(100 \times \text{Normal RMS } (150\text{--}250 \text{ Hz}) \text{ mean})}{(\text{Normal RMS mean } (0\text{--}10 \text{ Hz}) + (10\text{--}60 \text{ Hz}) + (60\text{--}150 \text{ Hz}) + (150\text{--}250 \text{ Hz}))} = NX3$$

Normal RMS Standard Deviation (150–250 Hz) = NXSD3

Then:

$$\frac{SX3 - NX3}{NXSD3} = PX9 = P19$$

For Frank (ECG) Y lead, (IE. VERTICAL AXIS)
Define:

$$\frac{(100 \times \text{Subject RMS } (0\text{--}10 \text{ Hz}) \text{ mean})}{\left( \begin{array}{l} (\text{Subject RMS mean } (0\text{--}10 \text{ Hz}) + (10\text{--}60 \text{ Hz}) + \\ (60\text{--}150 \text{ Hz}) + (150\text{--}250 \text{ Hz})) = SY0 \end{array} \right)} = SY0$$

$$\frac{(100 \times \text{Normal RMS } (0\text{--}10 \text{ Hz}) \text{ mean})}{(\text{Normal RMS mean } (0\text{--}10 \text{ Hz}) + (10\text{--}60 \text{ Hz}) + (60\text{--}150 \text{ Hz}) + (150\text{--}250 \text{ Hz}))} = NY0$$

Normal RMS Standard Deviation (0–10 Hz) = NYSD0

Then:

$$\frac{SY0 - NY0}{NYSD0} = PY6 = P20$$

Define:

$$\frac{(100 \times \text{Subject RMS } (10\text{--}60 \text{ Hz}) \text{ mean})}{(\text{Subject RMS mean } (0\text{--}10 \text{ Hz}) + (10\text{--}60 \text{ Hz}) + (60\text{--}150 \text{ Hz}) + (150\text{--}250 \text{ Hz}))} = SY1$$

-continued $$\frac{(100 \times \text{Normal RMS } (10\text{–}60 \text{ Hz}) \text{ mean})}{(\text{Normal RMS mean } (0\text{–}10 \text{ Hz}) + (10\text{–}60 \text{ Hz}) + (60\text{–}150 \text{ Hz}) + (150\text{–}250 \text{ Hz}))} = NY1$$

Normal RMS Standard Deviation (10–60 Hz) = NYSD1

Then:

$$\frac{SY1 - NY1}{NYSD1} = PY7 = P21$$

Define:

$$\frac{(100 \times \text{Subject RMS } (60\text{–}150 \text{ Hz}) \text{ mean})}{(\text{Subject RMS mean } (0\text{–}10 \text{ Hz}) + (10\text{–}60 \text{ Hz}) + (60\text{–}150 \text{ Hz}) + (150\text{–}250 \text{ Hz}))} = SY2$$

$$\frac{(100 \times \text{Normal RMS } (60\text{–}150 \text{ Hz}) \text{ mean})}{(\text{Normal RMS mean } (0\text{–}10 \text{ Hz}) + (10\text{–}60 \text{ Hz}) + (60\text{–}150 \text{ Hz}) + (150\text{–}250 \text{ Hz}))} = NY2$$

Normal RMS Standard Deviation (60–150 Hz) = NYSD2

Then:

$$\frac{SY2 - NY2}{NYSD2} = PY8 = P22$$

Define:

$$\frac{(100 \times \text{Subject RMS } (150\text{–}250 \text{ Hz}) \text{ mean})}{(\text{Subject RMS mean } (0\text{–}10 \text{ Hz}) + (10\text{–}60 \text{ Hz}) + (60\text{–}150 \text{ Hz}) + (150\text{–}250 \text{ Hz}))} = SY3$$

$$\frac{(100 \times \text{Normal RMS } (150\text{–}250 \text{ Hz}) \text{ mean})}{(\text{Normal RMS mean } (0\text{–}10 \text{ Hz}) + (10\text{–}60 \text{ Hz}) + (60\text{–}150 \text{ Hz}) + (150\text{–}250 \text{ Hz}))} = NY3$$

Normal RMS Standard Deviation (150–250 Hz) = NYSD3

Then:

$$\frac{SY3 - NY3}{NYSD3} = PY9 = P23$$

For Frank (ECG) Z lead, (IE. FRONT TO BACK AXIS)
Define:

$$\frac{(100 \times \text{Subject RMS } (0\text{–}10 \text{ Hz}) \text{ mean})}{(\text{Subject RMS mean } (0\text{–}10 \text{ Hz}) + (10\text{–}60 \text{ Hz}) + (60\text{–}150 \text{ Hz}) + (150\text{–}250 \text{ Hz}))} = SZ0$$

$$\frac{(100 \times \text{Normal RMS } (0\text{–}10 \text{ Hz}) \text{ mean})}{(\text{Normal RMS mean } (0\text{–}10 \text{ Hz}) + (10\text{–}60 \text{ Hz}) + (60\text{–}150 \text{ Hz}) + (150\text{–}250 \text{ Hz}))} = NZ0$$

Normal RMS Standard Deviation (0–10 Hz) = NZSD0

Then:

$$\frac{SZ0 - NZ0}{NZSD0} = PZ6 = P24$$

Define:

$$\frac{(100 \times \text{Subject RMS } (10\text{–}60 \text{ Hz}) \text{ mean})}{(\text{Subject RMS mean } (0\text{–}10 \text{ Hz}) + (10\text{–}60 \text{ Hz}) + (60\text{–}150 \text{ Hz}) + (150\text{–}250 \text{ Hz}))} = SZ1$$

$$\frac{(100 \times \text{Normal RMS } (10\text{–}60 \text{ Hz}) \text{ mean})}{(\text{Normal RMS mean } (0\text{–}10 \text{ Hz}) + (10\text{–}60 \text{ Hz}) + (60\text{–}150 \text{ Hz}) + (150\text{–}250 \text{ Hz}))} = NZ1$$

Normal RMS Standard Deviation (10–60 Hz) = NZSD1

Then:

$$\frac{SZ1 - NZ1}{NZSD1} = PZ7 = P25$$

Define:

$$\frac{(100 \times \text{Subject RMS } (60\text{–}150 \text{ Hz}) \text{ mean})}{(\text{Subject RMS mean } (0\text{–}10 \text{ Hz}) + (10\text{–}60 \text{ Hz}) + (60\text{–}150 \text{ Hz}) + (150\text{–}250 \text{ Hz}))} = SZ2$$

$$\frac{(100 \times \text{Normal RMS } (60\text{–}150 \text{ Hz}) \text{ mean})}{(\text{Normal RMS mean } (0\text{–}10 \text{ Hz}) + (10\text{–}60 \text{ Hz}) + (60\text{–}150 \text{ Hz}) + (150\text{–}250 \text{ Hz}))} = NZ2$$

Normal RMS Standard Deviation (60–150 Hz) = NZSD2

Then:

$$\frac{SZ2 - NZ2}{NZSD2} = PZ8 = P26$$

Define:

$$\frac{(100 \times \text{Subject RMS } (150\text{–}250 \text{ Hz}) \text{ mean})}{(\text{Subject RMS mean } (0\text{–}10 \text{ Hz}) + (10\text{–}60 \text{ Hz}) + (60\text{–}150 \text{ Hz}) + (150\text{–}250 \text{ Hz}))} = SZ3$$

-continued $$\frac{(100 \times \text{Normal RMS } (150\text{–}250 \text{ Hz}) \text{ mean})}{(\text{Normal RMS mean } (0\text{–}10 \text{ Hz}) + } = NZ3$$
$$(10\text{–}60 \text{ Hz}) + (60\text{–}150 \text{ Hz}) + (150\text{–}250 \text{ Hz}))$$

Normal RMS Standard Deviation (150–250 Hz) = NZSD3

Then:

$$\frac{SZ3 - NZ3}{NZSD3} = PZ9 = P27$$

Three (3) additional calculations are then performed in which Subject RMS means of ratios of RMS means obtained from the Frank (ECG) X-Y-Z leads, are subtracted from corresponding RMS means of ratios obtained similarly from normals, the results of which subtraction are then divided by RMS Standard Deviations of normal corresponding RMS ratios to provide additional numbers (Pi):
For the Frank (ECG) X-Y-Z leads $$\frac{\text{Subject RMS } (X/Y) \text{ mean} - \text{Normal RMS } (X/Y) \text{ mean}}{\text{Normal Standard Deviation } (X/Y)} = P(X/Y)$$
$$= P28$$

$$\frac{\text{Subject RMS } (Y/Z) \text{ mean} - \text{Normal RMS } (Z/Y) \text{ mean}}{\text{Normal Standard Deviation } (Y/Z)} = P(Y/Z)$$
$$= P29$$

$$\frac{\text{Subject RMS } (X/Z) \text{ mean} - \text{Normal RMS } (X/Z) \text{ mean}}{\text{Normal Standard Deviation } (X/Z)} = P(X/Z)$$
$$= P30$$

Continuing, each of the above up to thirty (30) calculated numbers:
(PX1-P1, PX2-P2, PX3-P3, PX4-P4, PX5-P5, PX6-P6 PX7-P7, PX8-P8, PX9-P9), (PY1-P10, PY2-P11, PY3-P12, PY4-P14, PY6-P15, PY7-P16, PY8-P17, PY9-P18), (PZ11-P19, PZ2-P20, PZ3-P21, PZ4-P22, PZ5-P23, PZ6-P24, PZ7-P25, PZ8-P26, PZ9-P27), P(X/Y-P28), P(Y/Z)-P29 and P(X/Z)-P30), (generally identified as (Pi)),
can optionally be compared to a corresponding assumed distribution of normal data to arrive at a "Score" component number. If a number (Pi) is within some ± "X" RMS Standard Deviation range of the RMS mean as shown below, a "Score" component number (Si) is taken to be:
If $-1\times<(Pi)<1\times$ then Si=0;
If $-2\times<(Pi)<-1\times$ or
If $1\times<(Pi)<2\times$ then Si=1;
If $-3\times<(Pi)<-2\times$ or
If $2\times<(Pi)<3\times$ then Si=2;
If $-4\times<(Pi)<-3\times$ or
If $3\times<(Pi)<4\times$ then Si=3 etc.
FIG. 4 demonstrates this graphically.

Continuing, each resulting "Score" component (PI) or (Si) calculated as just described is then subjected to a final test to determine if it should be accepted or rejected. Said final test involves comparing the Subject RMS mean to the data from which the Normal RMS mean was calculated. If less than or equal to ninety-five (95%) percent of the data points from which the Normal RMS mean was calculated are more than the subject's RMS mean the associated "Score" component is accepted, otherwise it is rejected. Accepted "Score" component numbers are then added to provide a final numerical "Score".

It has been found that if said final numerical "Score" is "low", (eg. approximately 0 to 7), then the Subject involved is more likely to be normal. If the final numerical "Score" is "high", (eg. greater than about 8), then the Subject is more likely to be abnormal.

Figure 5:
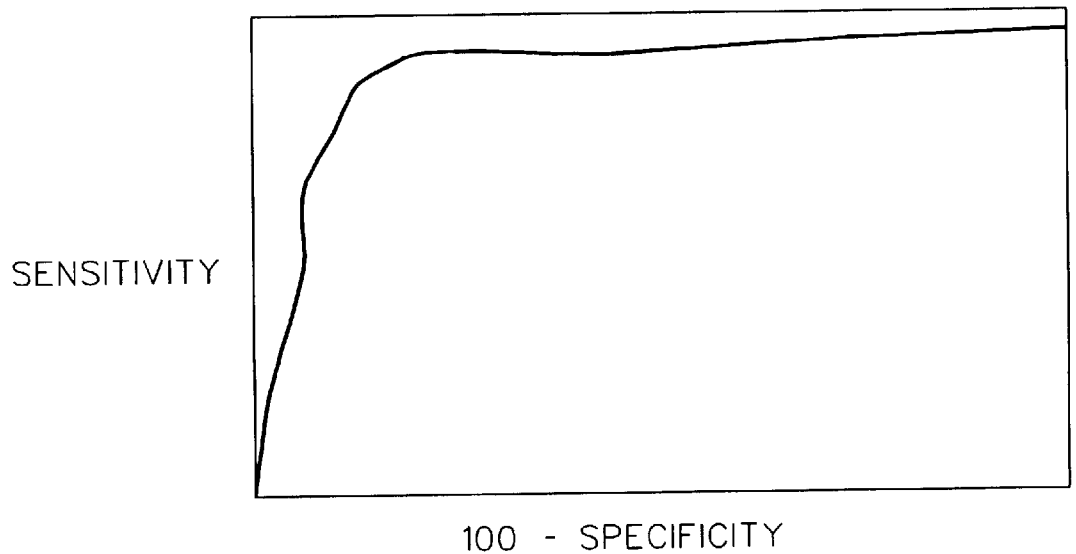
FIG. 5 shows sample results as provided by practice of the present invention plotted on an ROC curve in which a (100-Specificity), and Sensitivity, appear on the abscissa and ordinate respectively.

A particularly relevant approach to presenting the results of applying the disclosed method of the present invention is demonstrated by FIG. 5. FIG. 5 shows a plot in which the abscissa is (100-specificity) and the ordinate is (sensitivity). These terms are well known and mean:

$$\text{Specificity} = \frac{\text{Normals with Negative Test}}{\text{All Normals Tested}}$$

$$\text{Sensitivity} = \frac{\text{Abnormal with Positive Test}}{\text{All Abnormals Tested}}.$$

Figure 8:
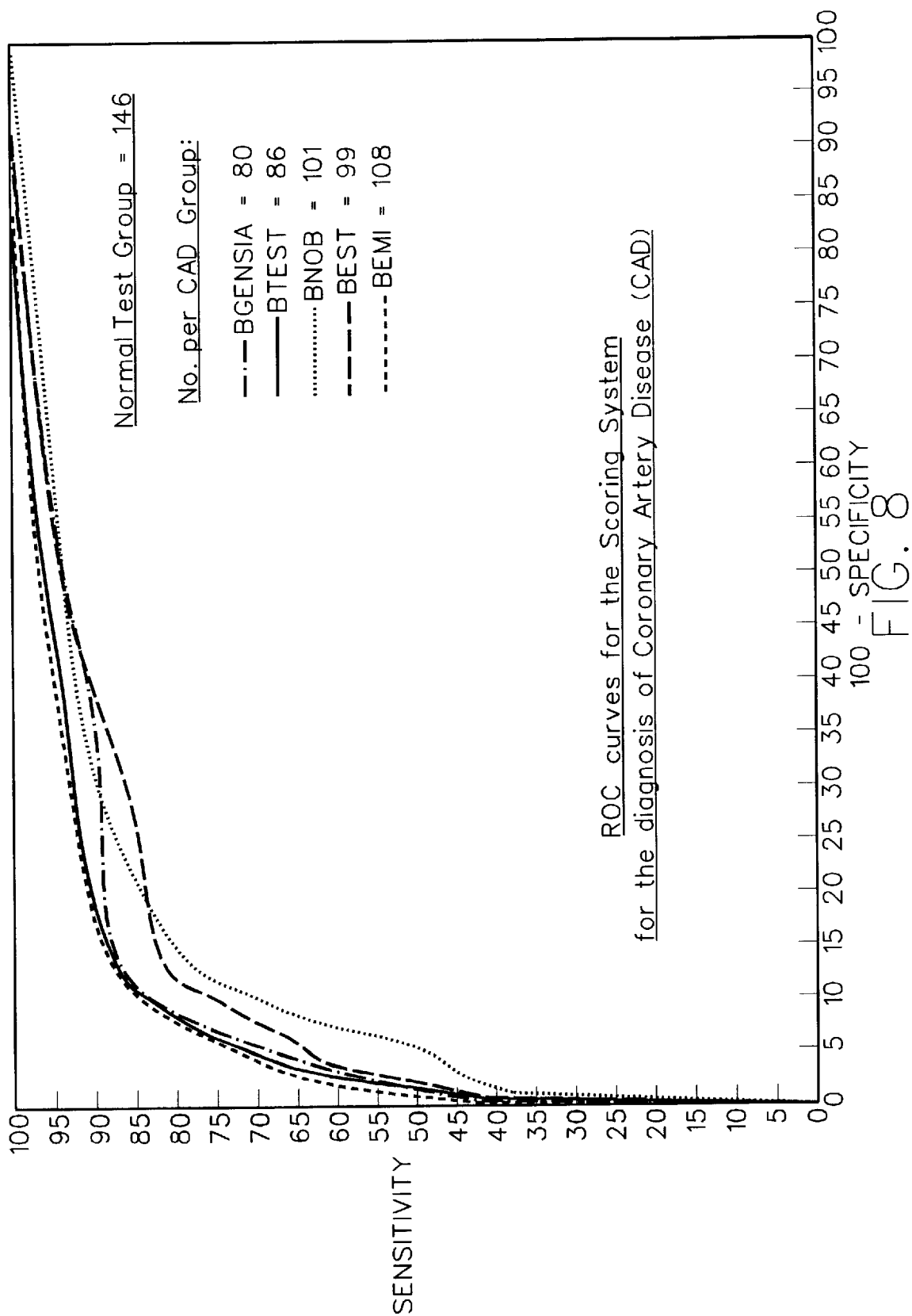
FIG. 8 shows actual data obtained from various subject groups by practice of the present invention, on a ROC curve
Figure 9:
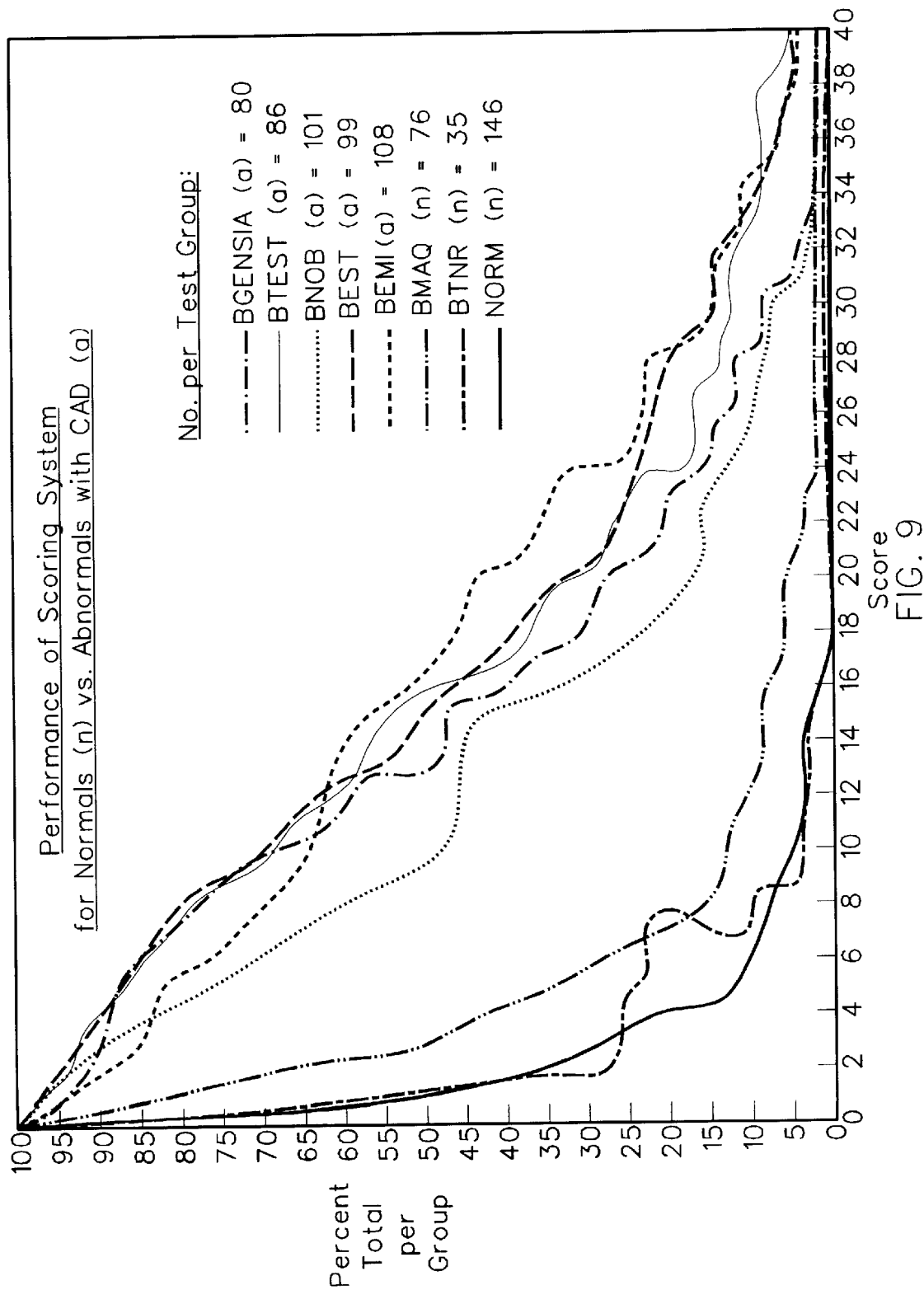
FIG. 9 shows actual data obtained from various subject groups by practice of the present invention, on a graph in which the abcsissa is scaled linearly with the present invention "Score".

The curve in FIG. 5 is demonstrative of those which populations of subjects provide in an (ROC) format. The present invention method provides that (ROC) curves be prepared by associating a "Score" value with the abscissa, in a nonlinear manner, and the percentage of a group having said "Score" value with the ordinate of such a plot. The success of the present invention in identifying and distinguishing abnormal subjects has been demonstrated to be quite striking. FIGS. 8 and 9, discussed supra, better serve to demonstrate this with actual empirically derived data.

FIGS. 6X1 through 6Z4 show twelve (12) diagrams, 6X1, 6X2, 6X3, 6X4, 6Y1, 6Y2, 6Y3, 6Y4, 6Z1, 6Z2, 6Z3 and 6Z4, of subject time domain sample date recorded from Frank X, Y and Z leads. Higher frequency band data are presented as one progresses from FIG. 6X1 to 6X4, and from FIG. 6Y1 to 6Y4, and from FIG. 6Z1 to 6Z4.

More particularly, FIGS. 6X1, 6Y1 and 6Z1 show filtered composite subject (ECG) data set time domain waveforms obtained from X, Y and Z leads, respectively, of a Frank ECG system in frequency band range of 0.0–10 HZ. FIGS. 6X2, 6Y2 and 6Z2 show filtered composite subject (ECG) data set time domain waveforms obtained from X, Y and Z leads, respectively, of a Frank ECG system for the frequency band of 10–60 HZ. FIGS. 6X3, 6Y3 and 6Z3 show filtered composite subject (ECG) data set time domain waveforms obtained from X, Y and Z lead&, respectively, of a Frank ECG system for the frequency band of 60–150 HZ. FIGS. 6X4, 6Y4 and 6Z4 show filtered composite subject (ECG) data set time domain waveforms obtained from X, Y and Z leads, respectively, of a Frank ECG system for the frequency band of 150–250 HZ. It is noted that the plots for the 60–150 and 150–250 HZ bands present as "envelopes" as signals go positive to negative and vice versa in very short time periods, (i.e. over a few "Sample Numbers"). All plots in FIGS. 6X1–6Z4 have the ordinate marked in micro-volts, and the abscissa is marked in digital filter data points 0 to 600, taken at progressive times during an (ECG) cycle.

It is noted that FIGS. 6Y3 and 6Y4 show "Rhomboids" present in the segement past the QRS complex region, (ie. in channels 375–600). The Rhomboids are shown as dashed-line to indicate that they were added to the actual patient data graph. This was done in preference to cluttering the Disclosure with an additional page of Drawings, however, the point to be made is that the presence of said "Rhomboids" in at least one time domain, frequency band plot, and especially said presence in more than one such frequency band plot, is very indicative of a patient in danger of Sudden Death.

FIGS. 7aX1–7aZ5 show fifteen (15) diagrams of typical subject data in frequency domain Power Spectral Density form, (with Magnitude on ordinate), plotted as a function of Frequency, (on abscissa). FIGS. 7bX1–7bZ5 show fifteen (15) diagrams of typical subject data in Time Domain form, (Magnitude on ordinate), plotted as a function of Time, (on abscissa). All said identified plots provide Magnitude, on the ordinate, in microvolts.

More particularly, it is noted that FIGS. 7aX1, 7aY1 and 7aZ1 show subject composite (ECG) data set frequency domain power spectral density plots derived from X, Y and Z leads, respectively, of a Frank ECG system, over a frequency band of 0.0 to 100 HZ. FIGS. 7aX2, 7aY2 and 7aZ2 show subject composite (ECG) data set frequency domain power spectral density plots derived from X, Y and Z leads, respectively, of a Frank ECG system, over a frequency band of 0.0 to 15 HZ. FIGS. 7aX3, 7aY3 and 7aZ3 show subject composite (ECG) data set frequency domain power spectral density plots derived from X, Y and Z leads, respectively, of a Frank ECG system, over a frequency band of 0.0 to 80 HZ. FIGS. 7aX4, 7aY4 and 7aZ4 show subject composite (ECG) data set frequency domain power spectral density plots derived from X, Y and Z leads, respectively, of a Frank ECG system, over a frequency band of 50 to 200 HZ. FIGS. 7aX5, 7aY5 and 7aZ5 show subject composite (ECG) data set frequency domain power spectral density plots derived from X, Y and Z leads, respectively, of a Frank ECG system, over a frequency band of 100 to 300 HZ. All plots in FIGS. 7aX1–7aZ4 have the ordinate marked in micro-volts, and the abscissa is marked in HZ, (i.e. cycles per second).

As well, FIGS. 7bX1, 7bY1 and 7bZ1 show subject composite (ECG) data set time domain waveforms obtained from X, Y and Z leads, respectively, of a Frank ECG system in an unfiltered full requisite frequency band. FIGS. 7bX2, 7bY2 and 7bZ2 show subject composite (ECG) data set time domain waveforms obtained from X, Y and Z leads, respectively, of a Frank ECG system in a filtered frequency band range of 0.0–10 HZ. FIGS. 7bX3, 7bY3 and 7bZ3 show subject composite (ECG) data set time domain waveforms obtained from X, Y and Z leads, respectively, of a Frank ECG system in a filtered frequency band range of 10–60 HZ. FIGS. 7bX4, 7bY4 and 7bZ4 show subject composite (ECG) data set time domain waveforms obtained from X, Y and Z leads, respectively, of a Frank ECG system in a filtered frequency band range of 60–150 HZ. FIGS. 7bX5, 7bY5 and 7bZ5 show subject composite (ECG) data set time domain waveforms obtained from X, Y and Z leads, respectively, of a Frank ECG system in a filtered frequency band range of 150–250 HZ. It is noted that the plots for the 60–150 and 150–250 HZ bands present as "envelopes" as signals go positive to negative aid vice versa in very short time periods, (ie. over a few "Sample Numbers"). All plots in FIGS. 7bX1–7bZ5 have the ordinate marked in micro-volts, and the. abscissa is marked in digital filter Sample Number data points, taken at progressive times during a (ECG) cycle. The present invention then makes use of such visual aids as an added feature. The three curves in each plot represent normal mean and plus/minus one standard deviations, and subject data. It is also to be understood that the above described approach to diagnosis can be applied to tracking patients over time and can be applied before and after various stress tests which attempt to provoke otherwise indolent or silent coronary artery abnormalities. Stress tests can, for example, involve treadmill exertion or a cold pressor test in which a subject simply places an arm into cold water for a few minutes. Changes in "Score" results combined with changes in the appearance of Power Spectral Density (PSD) and Amplitude Plots over time or before and after stress tests can provide insight as to a subject's coronary health not made available by less vigerous testing. Multiple mean curves can be simultaneously presented on a single plot to allow easy visual comparison of changes in Power Spectral Density as a function of time or stress. Observation of changes in (PSD) plots in the various frequency bands is a correlated part of the method of the present invention. Of particular interest, the inventor has noted that plots of (PSD) in the frequency ranges of sixty (60) to one-hundred-fifty (150) HZ and one-hundred-fifty (150) HZ to two-hundred-fifty (250) HZ show the greatest change in visually observable shape when a cold pressor test is administered. This is considered a significant observation.

Note also that as shown in FIG. 7aX1, it is common to include numerical representation in frequency as well as the time domain plots. Four numbers can be present. Using the Power Spectral Density plot as an example, when present said numbers are representations of:

Upper left—the number of Standard Deviations a Subject Power Spectral Density Value is away from a corresponding Normal Power Spectral Density Value for the Frequency Band in the Plot.

Lower Left—the Percentage of Normals which are below the Subject Power Spectral Density Value for the Frequency Band in the Plot.

Upper Right—the number of Normalized, (ie. Subject Power Spectral Density Value in the Frequency Band of the Plot divided by the Sum of Power Spectral Density Values for all Frequency Bands), Standard Deviations a Subject Power Spectral Value is away from a corresponding Normalized Subject Power Spectral Density Value for Normals for the Frequency Band in the Plot.

Lower Right—the Percentage of Normals which are below the Normalized Subject Power Spectral Density Value for the Frequency band in the Plot.
(Note that (RMS) values can be substituted for Power Spectral Density). Said numbers and visual Plots aid in interpretation of a Subject's "Score".

FIGS. 8 and 9 show (ROC) plots for actual data arrived at using the present invention method. Again, (ROC) curves typically plot Sensitivity vs. (100-Specificity) on ordinate and abscissa respectively, presented as percentages. Said Plots in FIGS. 8 and 9 were generated by associating the present invention "Score" with the abscissa (100-Specificity), but with the zero (0) thereof being at the right side so that the "Score" increases to the left. As the "Score" increases the percentage of each group of subjects associated therewith is plotted on the ordinate. By observation of FIGS. 8 and 9 it will be appreciated that as the "Score" increases the percentage of normals in a group of known normals having said "Score" value drops off rapidly, but the percentage of known abnormals in a group of known abnormals drops off much more slowly. For instance, at a "Score" of zero (0) all members of all groups are present. At a "Score" of five (5) approximately eighty (80%) percent of all members of an abnormal group will be present, but only approximately eleven (11%) percent of normals are present.

It is noted that a "Score" scale along the abscissa will be nonlinear, when compared to the (100-Specificity) scale.

FIG. 8 shows data presented in (ROC) format for Abnormals in various categories:

For subjects known to have had a myocardial infarction (MI) shown by twelve (12) lead (ECG), identified as (BEMI);

For subjects with non-specific ST-T wave abnormality on twelve (12) lead (ECG), identified as (BEST);

For a subjects with normal resting twelve (12) lead (ECG) but awaiting surgery, identified as (BNOB).

For a test set of patients who have (CAD), identified as (BTEST) and (BGENSIA).

FIG. 9 shows data plotted in FIG. 8 plotted in a different format in which the abcissa is scaled in terms of the "Score" developed by the present invention method.

Present is also a curve for Normals data, identified as (NORM).

Also included are curves for two groups additional groups of volunteer subjects which contain patients who have known risk factors for (CAD) identified as (BMAQ) and (BTNR). These constitute a "real-world" population of what are considered normals, in that both normals and abnormals are present. As would be expected, the data for the (BMAQ) and (BTNR) groups is generally positioned between the data for the known abnormal (BTEST) and normal groups.

The important thing to note is that the method of the present invention very definitely separates the various groups whether presented in the format of FIG. 8 or FIG. 9.

FIG. 102 provides a Flow Chart representation of the primary focus of the preferred embodiment of the Method of the present invention, said method comprising a noninvasive approach to investigating cardiac status of a subject, and enabling classification of a subject into normal and abnormal cardiac categories utilizing electrocardiography (ECG) data obtained therefrom.

The first steps (A) and (A') respectively, are shown to involve:

a. in step (A) obtaining data corresponding to (ECG) cycle(s) from at least one monitored lead(s) of an (ECG) system for a multiplicity of members of a population of subjects who have been documented as normal subjects, in that they do not show risk factors for, or demonstrate detectable cardiac abnormality; and b. in step (A') obtaining data corresponding to (ECG) cycle(s) from at least one monitored lead(s) of an (ECG) system for a subject, said monitored (ECG) system lead(s) utilized being the same as the monitored (ECG) system lead(s) utilized to obtain (ECG) cycle(s) for a multiplicity of normal subjects.

Next, in steps (B) and (B') respectively, a portion of an (ECG) cycle is selected, (eg. while the QRS complex is preferred, any portion, or the entire (ECG) cycle can be selected), for each of the normal subject population (B) and subject (B'). The same (ECG) cycle portion is typically selected for both the normal subject population and the subject.

Next, in steps (C) and (C'), in conjunction with application of filtering techniques, a plurality of data sets are arrived at for each monitored (ECG) system lead for both the normal subject population, (step (C)), and for the subject, (step (C')). Each of said data sets corresponds to a composite of said selected (ECG) cycle portion for said population of normal subjects in a selected frequency band range. It is disclosed that the preferred filtering technique is digital and has been utilized to provide data sets for:

a. data contained in all frequencies;

b. data contained in the frequency band of (0.0) to (10) HZ;

c. data contained in the frequency band of (10) to (60) HZ;

d. data contained in the frequency band of (60) to (150) HZ;

e. data contained in the frequency band of (150) to (250) HZ.

It is specifically disclosed, however, that data in only one frequency band range, (eg. all frequencies), can be provided in this step. It is also noted that other frequency bands can be selected, and that the recited bands are exemplary and nonlimiting.

(It is noted that steps (A), (B), (C) and (E) might be carried out only once for many runs of steps (A'), (B'), (C') and (E'). This is because steps (A), (B), (C) and (E) are applied to a normal subject population, which does not change, except perhaps when additional normal subject data are added to a normal subject populating data bank. Steps (A'), (B'), (C') and (E') must be run anew for each subject tested, however. Steps (D) and (F) will therefore access relatively standard values for the normal subject population, while accessing new values for each subject tested. However, steps (A), (B), (C) and (E) are inherently performed in the context of any testing of a subject.)

In step (D), normal subject population and subject (ECG) data set(s), (formed by user determined filtering techniques, (steps (C) and (C')), are plotted and displayed as a function of at least one parameter selected from the group consisting of time and frequency. It is noted that where data is plotted as a function of frequency a time to frequency domain conversion calculation must be performed to provide the frequency domain data. The results of this step are to provide as desired, visually interpretable plots of (ECG) magnitude and power spectral density. (It is noted that variations of the present invention procedure provide that, this step can omitted, or be performed after steps which directly follow, (eg. steps (E) and (E') or step (F)). Step (D) is presented at this point in the flow chart only because the data to be plotted and displayed is available at this point. It is further noted that step (D) can be performed utilizing a different selected (ECG) cycle portion, in steps (B) and (B'), than is selected and utilized in following steps (E), (E') and (F)), (eg. a full (ECG) cycle can be chosen for plotting and a QRS complex (ECG) cycle portion chosen for use in steps (E), (E') and (F)).

The next steps, (E) and (E') respectively, involve calculating corresponding representative parameter(s), and desired ratios thereof, from resulting data sets in said selected frequency band ranges for each monitored (ECG) system lead, for both the normal subject population (step (E)) and said subject, (step (E')). These steps are indicated as performed parallel to step (D) as data to allow both performance of step (D) and steps (E) and (E') is available at this point. (As noted above, the selected (ECG) cycle portion chosen in steps (B) and (B') and utilized in steps (E), (E') and (F) can be different than that utilized in step (D). It is also to be understood that in one version of the present invention procedure, steps (E), (E') and (F) can be omitted and only step (D) performed).

In step (F) corresponding subject and normal subject population representative parameter(s) and/or corresponding ratios of subject and ratios of normal subject population representative parameters are then compared and results of said comparison are combined to arrive at a "score", the magnitude of which "score" provides an indication of the cardiac status of said subject, and enables classification of a subject into normal and abnormal cardiac categories. A confidence level "acceptance test" can be optionally applied to qualify results of said comparisons for inclusion in arriving at said "score".

It is also noted that the step of calculating representative parameter(s) for normal subject population and subject data sets for monitored (ECG) system leads typically involves calculating at least one parameter selected from the group consisting of a root-mean-square mean and a root-mean-square standard deviation from said data set(s) from which composite(s) of a selected (ECG) cycle portion are calculated.

It is further noted that obtaining mean and standard deviation parameters, (typically, but not necessarily, based upon root-mean-square calculated parameters), enables practice of an "acceptance test" wherein a result of comparing subject to corresponding normal subject population parameters or ratios of a subject to corresponding ratios of the normal subject population parameters is accepted only if a subject acceptance parameter is offset by greater than, for instance, at least one normal subject population standard deviation from a mean of said normal subject population.

This step includes displaying of the "score" and when desired, components obtained from various composite data sets combined to arrive thereat.

Figure 10A:
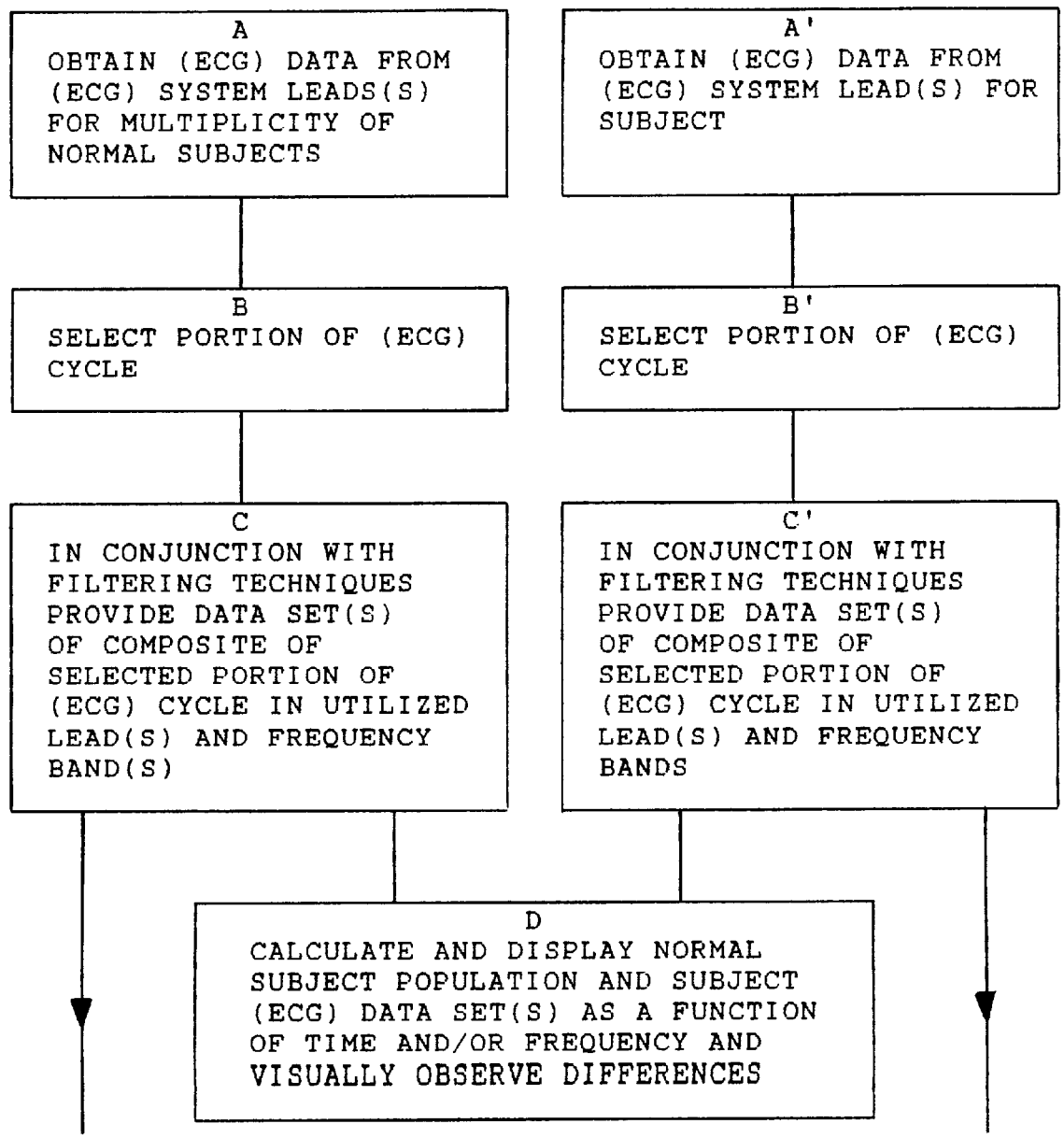
Figure 10A:
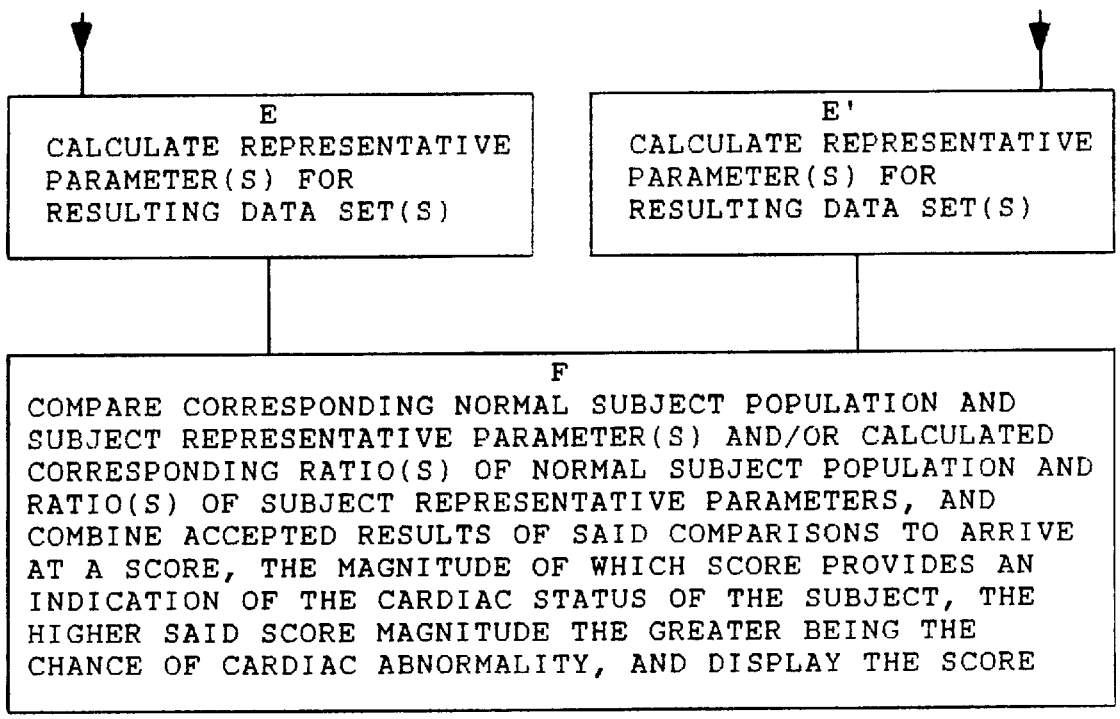
Figure 10B:
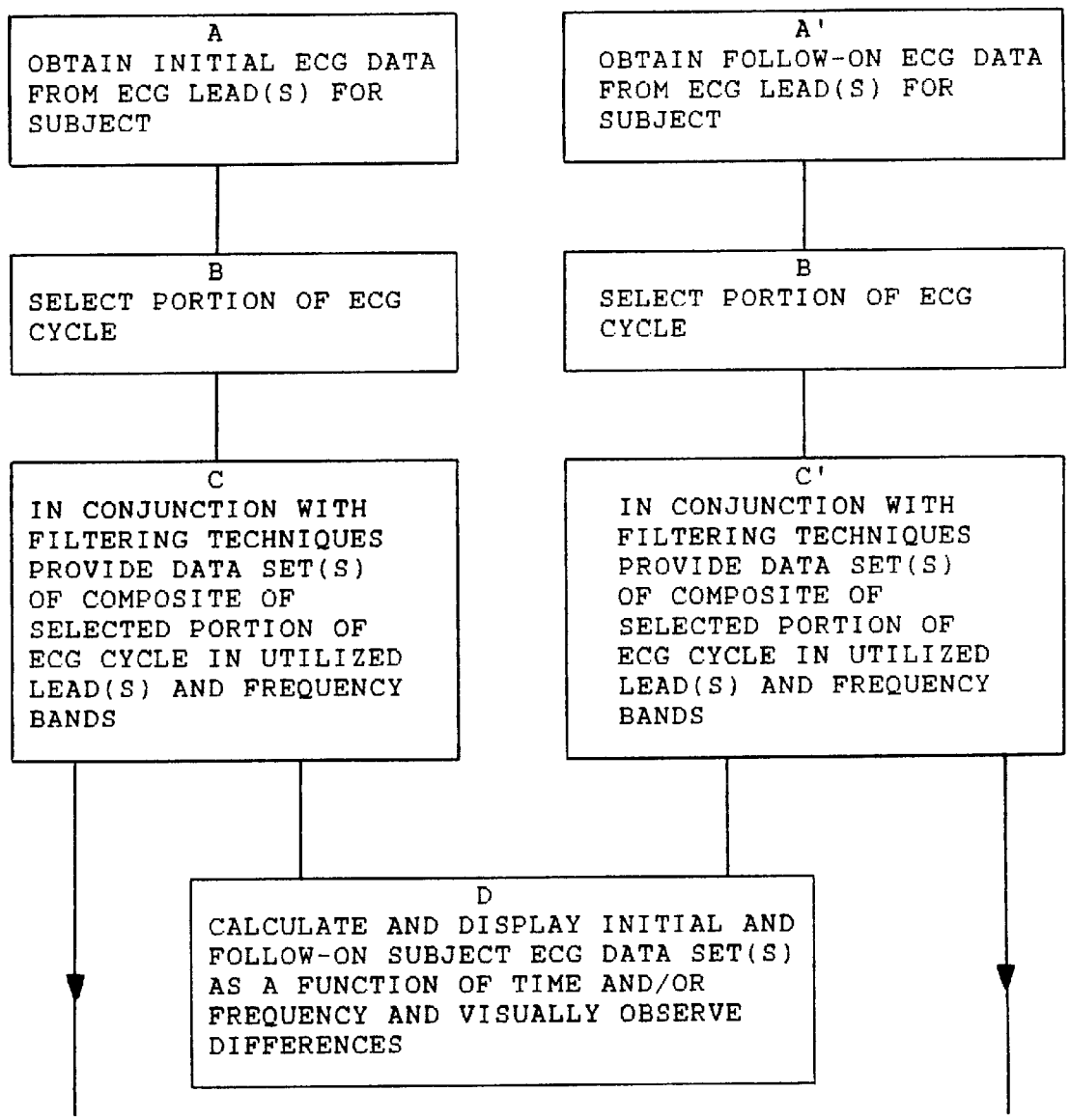
Figure 10B:
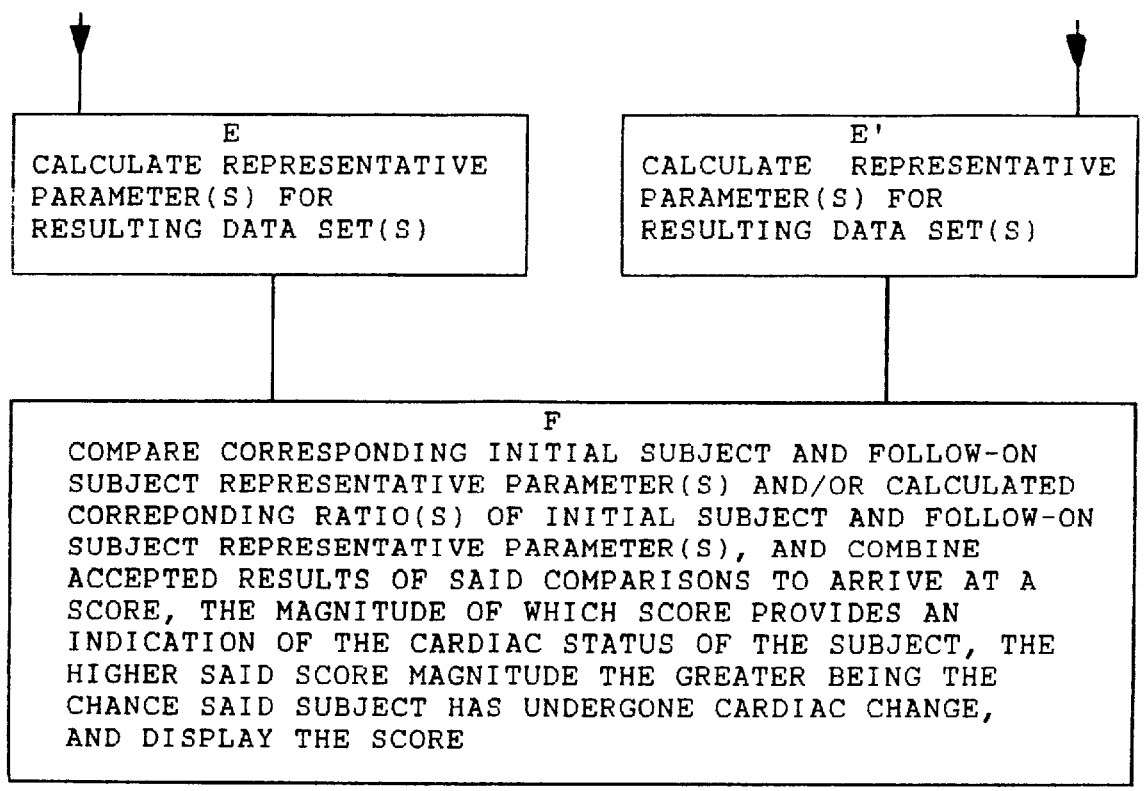
Figure 10D:
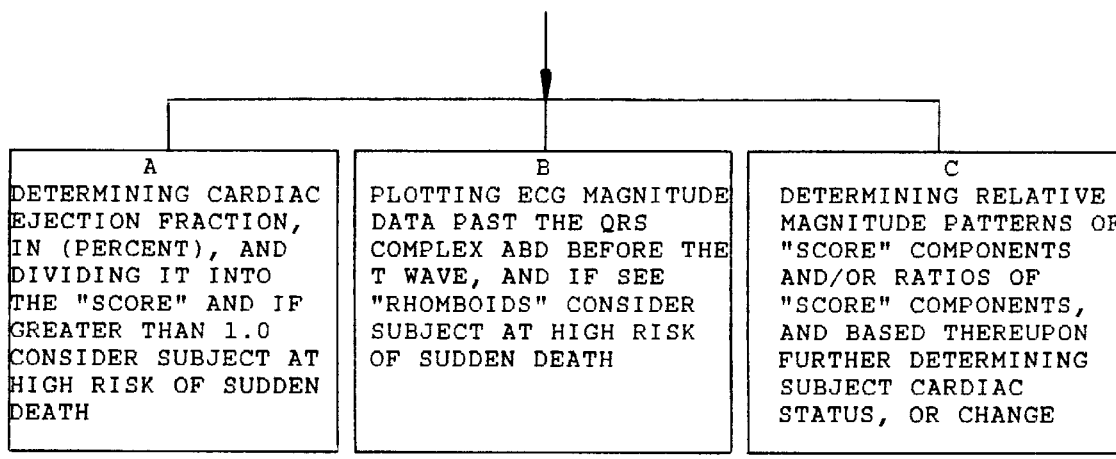

FIGS. 10b, 10c, and 10d are additional flow charts which show modifications of the method shown in FIG. 10a. The FIG. 10b Flow Chart shows application of the present invention method to Subject Cardiac Tracking. FIG. 10b is similar to FIG. 10a but the Normal Subject Population of FIG. 10a is replaced with Initial Subject ECG Data, and the Subject Data of FIG. 10a is replaced with Follow-On Subject Data. FIG. 10c shows application the present invention method of applying Confidence Bands in Accepting or Rejecting a "Score Component" Representative Parameter in calculating a "Score". FIG. 10d is to be interpreted to shows that after practicing the present invention methods shown in the Flow Charts of FIGS. 10a and 10b, additional steps can be applied which involve:

A. providing subject cardiac ejection fraction and dividing the "Score" thereby, and if the resulting value is over 1.0, considering said subject as at high risk for sudden death.

Figure 12:
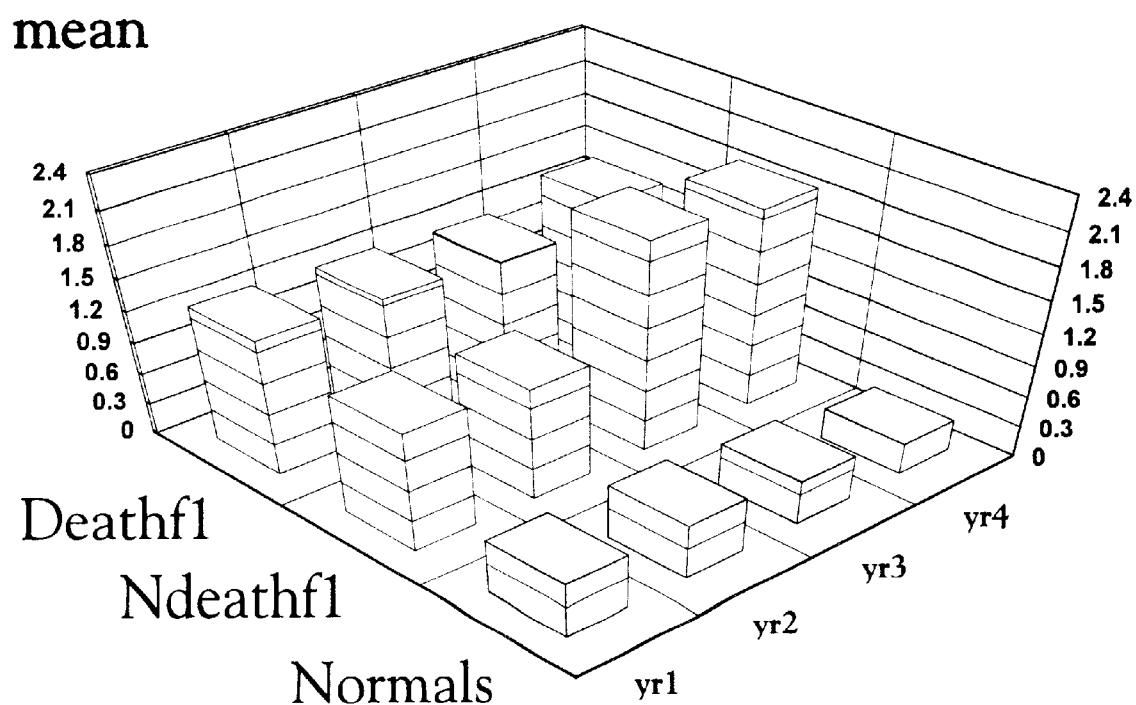
FIG. 12 shows a presentation of data developed by present invention methodology and indicates that patterns of subject abnormality can be observed in such a presentation.

B. identification of Rhomboids in a portion of an ECG cycle which which includes at least a portion of the S-T segement following the QRS complex, and if present, considering said subject as at high risk for sudden death; and C. comparing "Score" Components values as shown in FIG. 12 to identify Patterns therein, to further determine subject cardiac status, or change therein.

It has further been found by investigation of CAMI/11 data base data for Subjects known to be at risk for Sudden Death, that if dividing a present invention "Score" for a patient, (as provided by the described practice of the present invention), by the ejection fraction, (in Percent), of the patient, provides a result greater than one (1.0), then the patient involved is at high risk of Sudden Death.

Figure 11A:
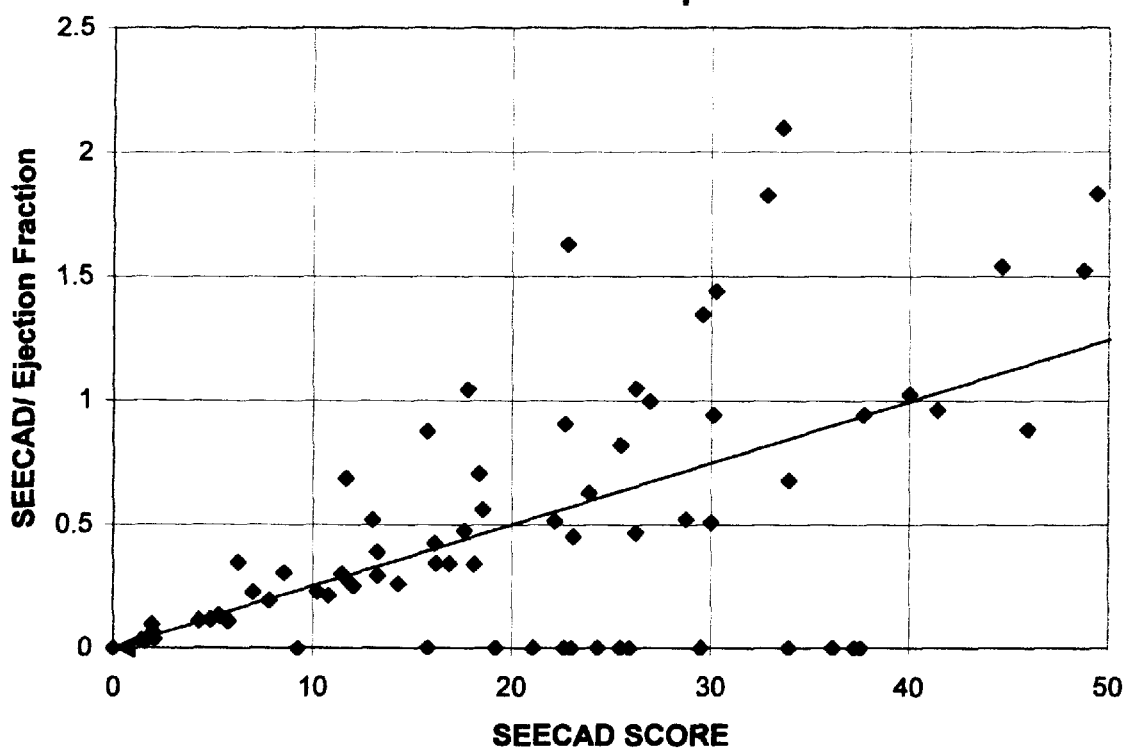
FIGS. 11a and 11b show reseptively, presentation of data for subjects at risk of sudden death and subjects not at risk of sudden death produced by present invention methodology.
Figure 11B:
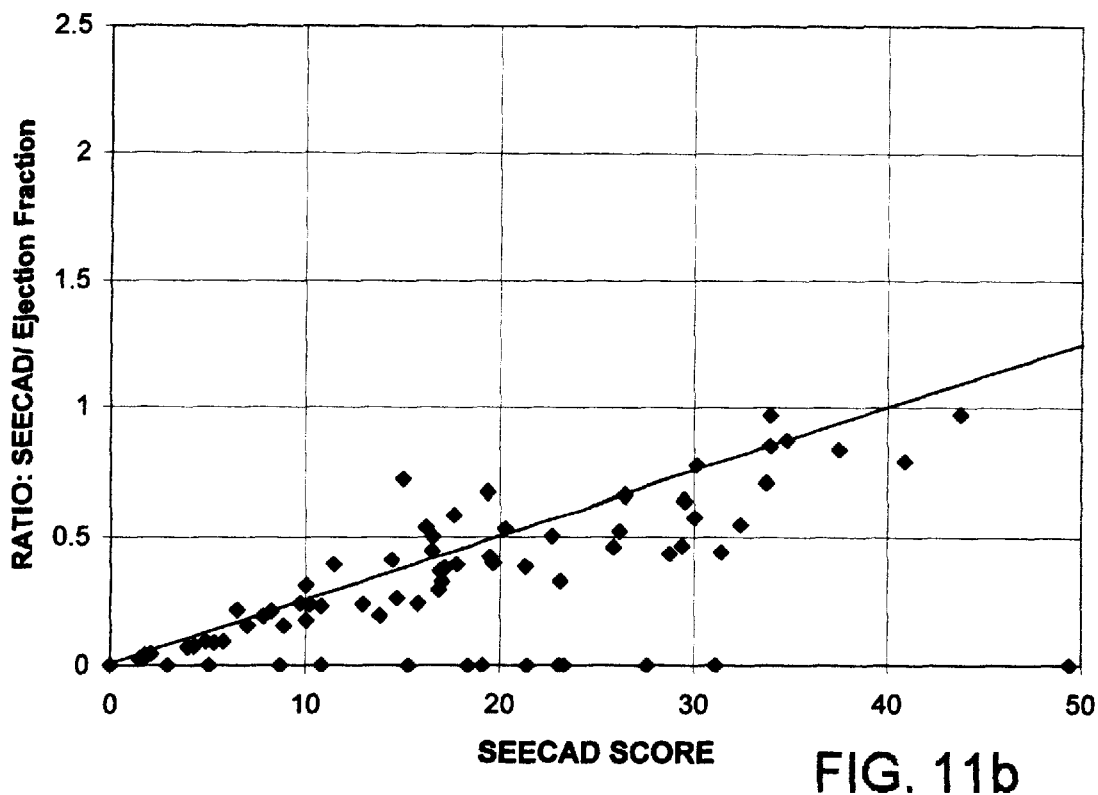

A visual presentation of the just described phenomona is quite striking, as is shown by in FIGS. 11a and 11b which show scatter-graphs demonstrating the relationship between said present invention:

("Score"/Ejection Fraction)

plotted against the present invention "Score", (termed "SEECAD"™ Score. ("SEECAD" is a Trademark owned by R & S Incorporated, a Canadian Corporation). Note, as shown in FIG. 11b, that a Population of Subjects not at risk for Sudden Death present with results wherein Subject data "scatter" is closely confined about the line which begins at (0.0, 0.0) and ends at (50, 1.5); whereas a population which demonstrated Sudden Death presents with data which demonstrate a much larger range of scatter. In addition, and most importantly on an individual patient basis, note that no Subject data in FIG. 11b exceed the value of 1.0 on the Abscissa, whereas a large number of Subjects shown in FIG. 11a provide data points above 1.0. The bottom line conclusion to be appreciated is that should a Subject present with a:

("Score"/Ejection Fraction)

value greater than 1.0, said Subject should be considered to definitely be a risk for Sudden Death. If said ratio is coupled with the presence of previously described "Rhomboids" present following a QRS complex in Time Domain Plots, (see for instance demonstration in FIGS. 6Y3 and 6Y4), then the patient involved should be considered to be at very high risk for sudden death. This combination of present invention "SEECAD" Score with other typically obtained Cardiac Data provides insight to the potential scope of application of the present invention. The definition of and availability of the described "SEECAD" Score provided by practice of the present invention, has opened a whole new and very promising avenue in the area of Subject evaluation.

FIG. 12 shows a three-dimensional presentation of Data Components utilized in computing a "SEECAD"™ Score. FIG. 12 is included to show that such a presentation indicates that Patterns of:

Data components Standard Deviation from Normality, which data components were derived utilizing present invention methodology, can identify specific Subject Abnormality Data Patterns. It is emphasized that known efforts of previous researchers have had as a focus the diagnosis of Subject abnormality by the comparison of:

Subject Data to Abnormal Subject Population Data, and looking for a match.

The present invention then has a new focus, emphasis added. Again, the present invention focus is on comparing Subject Data to Normal Subject Population Data, and Patterns of Data Components which naturally arise thereform are found to be indicative of Specific Catagories of Abnormality. The fact that the present invention approach, based in comparing Subject Data to Normal Subject Population Data, results in Data Patterns which serve to indicate a Specific Subject Abnormality is a distinguishing factor of the present invention, and provides an extremely exciting area of continued development. It is projected that further work utilizing present invention non-invasively obtained "SEECAD" Score data and methodology will provide the ability to not only separate Abnormal from Normal Subjects, (already possible), but to further identify the most likely anatomical location of the source of identified Abnormality, (eg. specific myocardium, specific coronary-arteries etc).

Figure 13:
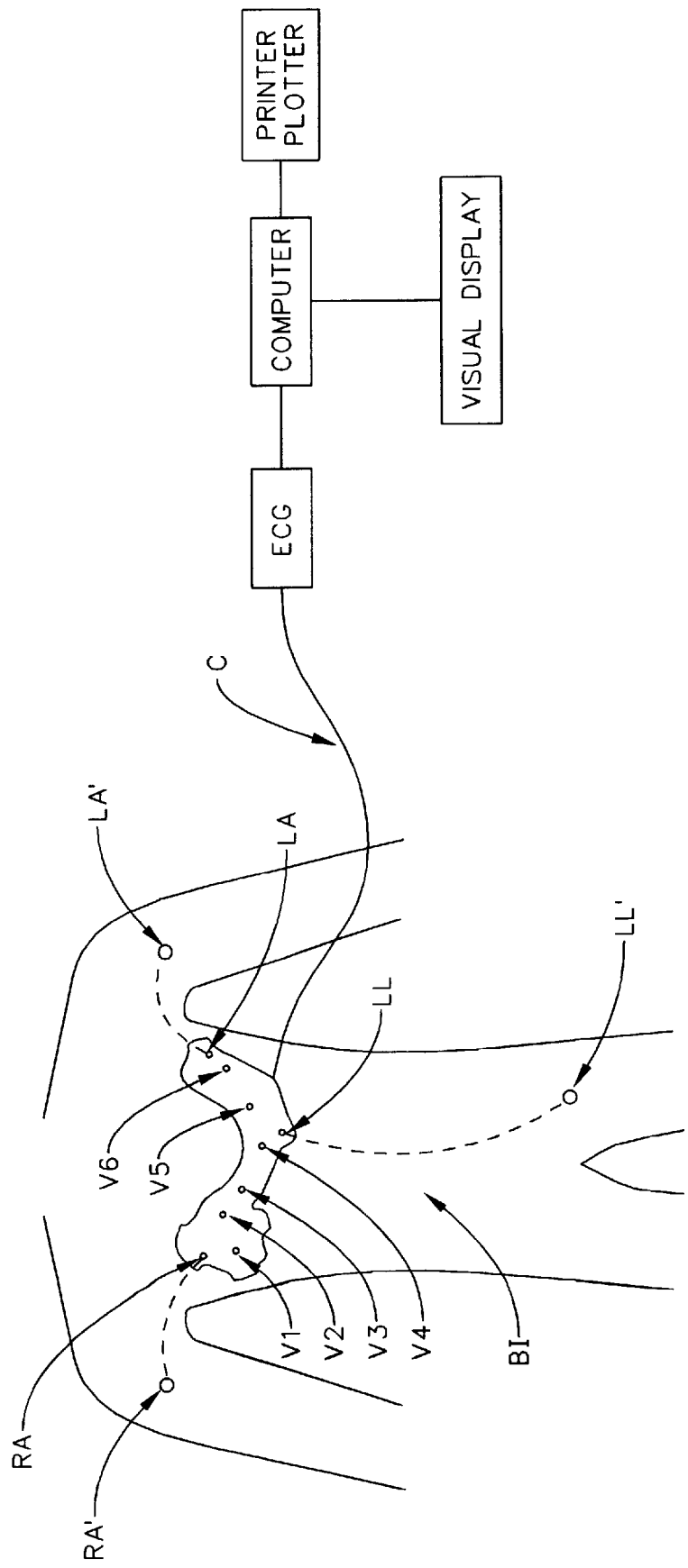
FIG. 13 shows a system for practicing the present invention method.

FIG. 13 shows a Diagram of the basic components of a system which can be utilized to practice the present invention method. A partial human torso is shown with a Chest mounted Bioelectric Interface (BI) thereon. (Note that equivalent limb electrodes (RA), (LA) (LL) are present therein). Conventional individual Limb, (e.g. RA', LA' and LL') and Precordial (ie. (v1), (v2), (v3), (v4), (v5) and (v6)) leads can, of course, be utilized as well, and shown precordial leads (V1), (V2), (V3), (V4), (V5) and (V6) are to be interpreted sufficiently broadly to indicate individual electrodes are accessed on the shown subject upper torso. It has been found, however, that use of a chest mountable Bioelectric Interface (BI), as shown, provides better (ECG) signals by maintaining relatively better electrode contact to a subject and relatively constant electrode spacing, in use. A Cable (C) provides electrical signals from said electrodes (RA), (LA), (LL,) (v1), (v2), (v3), (v4), (v5) and (v6) to an (ECG) monitor (ECG), which feeds to a Computational Means (COMPUTER), which in turn provides SEECAD™ data to a (VISUAL DISPLAY) and to a (PRINTER/PLOTTER). Of course FIG. 13 is only demonstrative and the present invention system is not limited to the configuration shown.

It is to be understood that throughout this Disclosure the RMS Mean values are cited. It is possible to utilize other calculated values, such as Averages, in the method of the present invention. The term "Mean" should be interpreted broadly to include such alternatives.

The terms "Assumed Gaussian" have also been used throughtout this Disclosure when refering to Data Distribution RMS Means and RMS Standard Deviations. It is noted that in fact, analysis of empirically obtained data has proven the assumption to be valid.

It is also to be understood that the Term "Rhomboid" is used herein only to generally identify the presence of (ECG) activity beyond the QRS complex as shown by dashed lines in FIGS. 6Y3 and 6Y4, and does not impose any plot locus shape limitations.

To provide full disclosure a print-out of major portions of the computer program utilized in the practice of the present invention is included herewith directly. Also included following the computer print-out is a table of data which documents the above discussed results.

49

| Dec 20 1994 19:31:35 | ecgzx.pro | Page 1 |

```
;***********************************************************
; INITIALIZE ARRAYS
;***********************************************************
INFILE_PATH='/usr2/multinorm/1_2/'
OUTFILE_PATH='/usr2/outplots/'
COMMON SP1,  K3, K4, X3, X4, K3D, K4D
COMMON SP2,  PXDATA, PYDATA, PZDATA, PXDATA1, PXDATA2, PXDATA3,PYDATA1
COMMON SP3,  PYDATA2, PZDATA2, PZDATA1, PYDATA3, PZDATA3, XDATA, YDATA, ZDA
COMMON SP4,  pidd0
COMMON SP5,  XDATA1, YDATA1, ZDATA1, XDATA2, YDATA2, ZDATA2,XDATA3,YDATA3,Z
COMMON SP6,  VMDATA2,pid,pidd1,pidd2,pidd3,pidd4,pidd5,pidd6,pidd7,pidd8,pi
COMMON SP7,  VMDATA
COMMON SP8,  XR
COMMON SP9,  OXDATA, OYDATA, OZDATA, OXDATA1, OXDATA2,OXDATA3, OXDATAN,OVMD
COMMON SP10, OVMDATA, OYDATA1,OYDATA2,OYDATA3,OZDATA1,OZDATA2,OZDATA3,OYDA
COMMON SP11, OZDATAN, OPXDATA1,OPXDATA2,OPXDATA3,OPXDATA, OPYDATA,OPYDATA1
COMMON SP12, OPYDATA2,OPYDATA3, OPZDATA,OPZDATA1,OPZDATA2,OPZDATA3
COMMON SP13, PIDDA
COMMON SP14, YYDATA, XXDATA, ZZDATA
COMMON SP15, OX,OY,OZ,OX1,OX2,OX3,OY1,OY2,Oy3,OZ1,OZ2,OZ3,OPX,OPY,OPZ,OPX1
COMMON SP16, XDATA1A,YDATA1A,ZDATA1A,XXD,YYD,ZZD,XXD1,YYD1,ZZD1,XXD2,YYD2,
COMMON SP17, XXD3,YYD3,ZZD3,XXD4,YYD4,ZZD4,XXD5,YYD5,ZZD5,XXD6,YYD6,ZZD6,X
COMMON SP18, OX1A,OY1A,OZ1A,OPx1a,opy1a,opz1a
COMMON NOX9, PATNAME,NUMBER,IDATA,J,JK,filen,s55,pxx,ECG,s5
COMMON NOY4, CCA,TABLES,DDSET,TABNAM,tablab1,ref
cca=fltarr(10,7,50)
ddset=intarr(30)
tables=fltarr(50,120)
tabnam=strarr(5,30)
tablab1=strarr(30)
tablab2=strarr(5)
tablab3=strarr(20)
tablab4=strarr(20)
k3=FLTARR(600)
k4=FLTARR(600)
X3=FLTARR(600)
x4=FLTARR(600)
xr=fltarr(500)
rR=INTARR(256)
gG=INTARR(256)
bB=INTARR(256)
XINDEX=INTARR(600)
XINDEX2=INTARR(150)
XINDEX3=INTARR(256)
XINDEX4=INTARR(100)
IDATA=INTARR(2096)
XDATA=FLTARR(600)
YDATA=FLTARR(600)
ZDATA=FLTARR(600)
XXDATA=FLTARR(600)
YYDATA=FLTARR(600)
ZZDATA=FLTARR(600)
OXDATA=FLTARR(600)
OYDATA=FLTARR(600)
OZDATA=FLTARR(600)
OXDATAN=FLTARR(600)
OYDATAN=FLTARR(600)
OZDATAN=FLTARR(600)
```

| Dec 20 1994 19:31:35 | ecgzx.pro | Page 2 |
|---|---|---|

```
OXXDATA=FLTARR(600)
OYYDATA=FLTARR(600)
OZZDATA=FLTARR(600)
XDATA1=FLTARR(600)
XDATA2=FLTARR(600)
XDATA3=FLTARR(600)
YDATA1=FLTARR(600)
YDATA2=FLTARR(600)
YDATA3=FLTARR(600)
ZDATA1=FLTARR(600)
ZDATA2=FLTARR(600)
ZDATA3=FLTARR(600)
XXD=fltarr(5,600)
YYD=fltarr(5,600)
ZZD=fltarr(5,600)
XXD1=fltarr(5,600)
YYD1=fltarr(5,600)
ZZD1=fltarr(5,600)
XXD2=fltarr(5,600)
YYD2=fltarr(5,600)
ZZD2=fltarr(5,600)
XXD3=fltarr(5,600)
YYD3=fltarr(5,600)
ZZD3=fltarr(5,600)
XXD4=fltarr(5,600)
YYD4=fltarr(5,600)
ZZD4=fltarr(5,600)
XXD5=fltarr(5,600)
YYD5=fltarr(5,600)
ZZD5=fltarr(5,600)
XXD6=fltarr(5,600)
YYD6=fltarr(5,600)
ZZD6=fltarr(5,600)
xume=fltarr(45,5,600)
PPXDATA=FLTARR(600)
PPYDATA=FLTARR(600)
PPZDATA=FLTARR(600)
PPXDATA1=FLTARR(600)
PPXDATA2=FLTARR(600)
PPXDATA3=FLTARR(600)
PPYDATA1=FLTARR(600)
PPYDATA2=FLTARR(600)
PPYDATA3=FLTARR(600)
PPZDATA1=FLTARR(600)
PPZDATA2=FLTARR(600)
PPZDATA3=FLTARR(600)
OPXDATA=FLTARR(600)
OPYDATA=FLTARR(600)
OPZDATA=FLTARR(600)
OPXDATA1=FLTARR(600)
OPXDATA2=FLTARR(600)
OPXDATA3=FLTARR(600)
OPYDATA1=FLTARR(600)
OPYDATA2=FLTARR(600)
OPYDATA3=FLTARR(600)
OPZDATA1=FLTARR(600)
OPZDATA2=FLTARR(600)
OPZDATA3=FLTARR(600)
```

| Dec 20 1994 19:31:35 | ecgzx.pro | Page 3 |

```
VMDATA=FLTARR(600)
VMDATA2=FLTARR(600)
BDATA=BYTARR(100)
NUMBER=INTARR(100)
pid=strarr(60)
pidd=strarr(1)
pidd1=strarr(250)
pidd2=strarr(1)
pidd3=strarr(1)
pidd4=strarr(1)
pidd5=strarr(1)
pidd6=strarr(1)
pidd7=strarr(1)
pidd8=strarr(15)
pidd9=strarr(1)
pidd0=strarr(1)
pidda=strarr(1)
piddb=strarr(1)
piddc=strarr(1)
piddd=strarr(1)
pidd='R&S Inc.: AIR Labs HFECG Analysis'
pidd0='Patient ID: '
piddd='--------------------------------------------------------
xxxx=STRARR(1)
xxx1=STRARR(1)
nnn='X'
S1=STRARR(31)
PATNAME=STRARR(100)
PAT=STRARR(1)
FILEX=STRARR(1)
FILEY=STRARR(1)
FILEZ=STRARR(1)
ssex=STRARR(1)
SRACE=STRARR(6)
SRACE(0)='Caucasian'
SRACE(1)='Black'
SRACE(2)='Oriental'
SRACE(3)='Hispanic'
SRACE(5)='Indian'
SRACE(4)='Unknown'
S3='.'
S4='1'
SX='x'
SY='y'
SZ='z'
S1(0)='0'
S1(1)='1'
S1(2)='2'
S1(3)='3'
S1(4)='4'
S1(5)='5'
S1(6)='6'
S1(7)='7'
S1(8)='8'
S1(9)='9'
S1(10)='10'
filen=2
for i=10,30 do begin
```

```
Dec 20 1994 19:31:35                    ecgzx.pro                         Page 4
sl(i)=strtrim(i,2)
endfor
tablab2(0)='   ABS VAL    % TOT      %L00      %DAYREF'
tablab3(0)='X 0-10 Hz      '
tablab3(1)='Y 0-10 Hz      '
tablab3(2)='Z 0-10 Hz      '
tablab3(3)='X 10-60 Hz     '
tablab3(4)='Y 10-60 Hz     '
tablab3(5)='Z 10-60 Hz     '
tablab3(6)='V  10-60 Hz    '
tablab3(7)='X 60-150 Hz    '
tablab3(8)='Y 60-150 Hz    '
tablab3(9)='Z 60-150 Hz    '
tablab3(10)='V  60-150 Hz'
tablab3(11)='X 150-250 Hz'
tablab3(12)='Y 150-250 Hz'
tablab3(13)='Z 150-250 Hz'
tablab3(14)='V 150-250 Hz'
tablab3(15)='X TOTAL        '
tablab3(16)='Y TOTAL        '
tablab3(17)='Z TOTAL        '
tablab4(0)='X 0-10 Hz      '
tablab4(1)='Y 0-10 Hz      '
tablab4(2)='Z 0-10 Hz      '
tablab4(3)='X 10-60 Hz     '
tablab4(4)='Y 10-60 Hz     '
tablab4(5)='Z 10-60 Hz     '
tablab4(6)='X 60-150 Hz    '
tablab4(7)='Y 60-150 Hz    '
tablab4(8)='Z 60-150 Hz    '
tablab4(9)='X 150-250 Hz'
tablab4(10)='Y 150-250 Hz'
tablab4(11)='Z 150-250 Hz'
tablab4(12)='X TOTAL        '
tablab4(13)='Y TOTAL        '
tablab4(14)='Z TOTAL        '
tables(*,2)=100.0
tables(*,3)=100.0
for ii=0,20 do begin
ij=ii*4
tables(27:32,ij+1)=100.0
endfor
ref=strarr(15)
again=0
;*************************************************************
;         INITIALIZE PLOTTING DEVICE
;*************************************************************
for iii=0,255 do begin
rr(iii)=0
gg(iii)=0
bb(iii)=0
endfor
rr(160)=239
gg(160)=24
bb(160)=108
gg(96)=228
bb(206)=255
gg(206)=220
```

53

| Dec 20 1994 19:31:35 | ecgzx.pro | Page 5 |

```
rr(254)=255
gg(254)=255
bb(28)=205
gg(28)=195
rr(28)=255
bb(10)=255
gg(10)=255
rr(10)=255
modifyct,4,4,rr,gg,bb
;*******************************************************
;   READ IN PATIENTS ID AND NUMBER
;*******************************************************
jumpagain:
PRINT, 'ENTER NUMBER OF PATIENTS TO BE PROCESSED'
READ, PATNUMBER
IF PATNUMBER EQ 0  THEN GOTO, JUMPOUT
FOR K=1,PATNUMBER DO BEGIN
PAT(*)=''
PRINT, 'FOR PATIENT ',strtrim(string(K),2),' ENTER NAME'
READ, PAT
PATNAME(K-1)=PAT
PRINT, PATNAME(K-1)
PRINT, 'FOR ', PATNAME(K-1), ' ENTER NUMBER OF DATASETS TO BE PROCESSED (N
READ, N
NUMBER(k-1)=N
ENDFOR ; /***End reading patient names and numbers ***/
;*******************************************************
;   LOOP FOR EACH PATIENT
;*******************************************************
FOR K=1,PATNUMBER DO BEGIN
nraz=intarr(30,3)
osd=strarr(10,7)
osdk=0
oxs=strarr(number(k-1))
oxx=fltarr(number(k-1),600)
oxy=fltarr(number(k-1),600)
oxz=fltarr(number(k-1),600)
LASTECG=1
numdays=0
for iiq=0,9 do begin
cca(iiq,5,1)=0.0
endfor
corref=0
jk=0
jk2=0
flag00= 0
IF NUMBER(K-1) EQ 0 THEN GOTO, JUMPOUT
if number(k-1) eq 1 then begin
flag00=1; flag for case of one dataset only
flag002=0;
number(k-1)=2
endif
jdiff=0
jumnum=0
flagjump=0
il=1
FOR J=1,NUMBER(K-1) DO BEGIN
if j eq 1 then begin
```

54

| Dec 20 1994 19:31:35 | ecgzx.pro | Page 6 |

```
if NUMBER(K-1) ge 3 then begin
    print,' you have input PATIENT ',PATNAME(K-1),' with ',NUMBER(K-1),'
    print,'ENTER a DATASET NUMBER TO BEGIN ANALYSIS OR 0 for default(0)'
    read,cn
    jumnum=fix(strtrim(cn,2))
    if jumnum eq number(k-1) then jumnum=jumnum-1
endif
endif
if j eq 2 then begin
if jumnum ne 0 then begin
j=jumnum
flagjump=1
jdiff=jumnum-j
endif
if flag00 eq 1 then begin
j=j-1
flag002=1
endif
endif
flexx=enter3(k)
if flexx gt 1 then goto, jumpat
print,filen
XXDATA=-1.0*XDATA
YYDATA=-1.0*YDATA
ZZDATA=-1.0*ZDATA
if j gt 1 then begin
if ecg ne lastecg or (j-jk) ge 4 then begin
jkk=jk
jn=j-jk-1
jk2=jk
jk=j-1
if flagjump eq 0 then begin
if jkk ne 0 then begin
device,pseudo=8
WINDOW, 0, colors=128, YPOS=80, XSIZE=1150, ySIZE=820, title=pidd
WINDOW, 5, colors=128, XSIZE=750, ypos=20,ySIZE=50, title=pidd
mmatdly0,jn;
PRINT,'ENTER X TO EXIT OR ANY OTHER CHAR TO CONTINUE'
READ,xxxx
if (xxxx(0) eq nnn) then goto, jump1
mmadly0,jn;
endif $
else begin
mmatdly,jn;
PRINT,'ENTER X TO EXIT OR ANY OTHER CHAR TO CONTINUE'
READ,xxxx
if (xxxx(0) eq nnn) then goto, jump1
mmadly2,jn;
endelse
pidd8(12)=''
PRINT,'ENTER X TO EXIT OR ANY OTHER CHAR TO CONTINUE'
READ,xxxx
if (xxxx(0) eq nnn) then goto, jump1
wdelete,1
;****************************************************************
;CALCULATE THE SCORES OF THE PATIENT COMPARED TO THE NORMAL POPULATION
;****************************************************************
scorez,tables,nraz,jkk,jn,csd,osdk
```

55

| Dec 20 1994 19:31:35 | ecgzx.pro | Page 7 |

```
PRINT,'ENTER X TO EXIT OR ANY OTHER CHAR TO CONTINUE'
READ,xxxx
if (xxxx(0) eq nnn) then goto, jump1
scorefs2,oxs,jkk,jk-1,oxx,oxy,oxz
PRINT,'ENTER X TO EXIT OR ANY OTHER CHAR TO CONTINUE'
READ,xxxx
if (xxxx(0) eq nnn) then goto, jump1
wdelete,0
wdelete,5
endif
endif
endif
flagjump=0
pidd8(12)=pidd8(12)+s55+' '
;*********************************************************
;     BEGIN PROCESSING AND PLOTTING
;*********************************************************
piddc=pidd+'   '+pidd0
tablabl(j-1)=s55
if (again eq 0) then begin
numdays=0
corref=0
loadct,4
status='WELCOME TO'
status='Press any character to continue'
wdelete,0
!P.BACKGROUND=1
endif
status='DISPLAY STATUS:  Time Domain Plots for X, Y, Z ECG leads'
!Y.MARGIN=[3,4]
!X.STYLE=1
!X.CRANGE=[0,599]
!P.BACKGROUND=1
!P.MULTI=[0,4,4,0,0]
!Y.TITLE='amplitude (microvolts)'
!Y.TITLE='sample number'
!P.CHARSIZE=1.35
!X.CHARSIZE=1.35
!Y.CHARSIZE=1.35
;*********************************************************
; FILTERING THE PATIENT DATA INTO 4 BANDS
;*********************************************************
mmfilter6
scorefs,xdata,ydata,zdata,xr,oxsd
Oxs(j-1)=oxsd
oxx(j-1,0:599)=xdata(0:599)
oxy(j-1,0:599)=ydata(0:599)
oxz(j-1,0:599)=zdata(0:599)
wdelete,1
status='DISPLAY STATUS:  Power Spectral Density Plots for X, Y, Z ECG lead
;*********************************************************
;POWER SPECTRUM CALCULATION AND DISPLAY
;*********************************************************
mmpower6
wdelete,1
tabnam(1,j-1)=pxx
tabnam(2,j-1)=pidd2
for ind=0,14 do begin
```

| Dec 20 1994 19:31:35 | ecgzx.pro | Page 8 |

```
jj=(j-1)*4
tables(ind,jj)=xr(ind)
tables(ind+15,jj)=xr(ind+50)
endfor
for ind=0,2 do begin
jj=(j-1)*4
ij=16+(ind*6)
ind3=ind*4
ind1=ind*4+3
ind2=ind*3+3
tables(ind1,jj+1)=xr(ij)
tables(ind1+1,jj+1)=xr(ij+2)
tables(ind1+2,jj+1)=xr(ij+4)
tables(ind2+15,jj+1)=xr(ij+47)
tables(ind2+16,jj+1)=xr(ij+49)
tables(ind2+17,jj+1)=xr(ij+51)
tables(ind1+3,jj+1)=xr(ij-ind3-1)
endfor
for ind=0,2 do begin
jj=(j-1)*4
tables(27+ind,jj)=xr(40+ind)
tables(30+ind,jj)=xr(90+ind)
tables(ind,jj+1)=xr(43+ind)
tables(ind+15,jj+1)=xr(93+ind)
endfor
if (ecg ne lastecg or (j-jk2) ge 4) then begin
if (j gt 1) then begin
jk2=jk
pidd8(0)=s55
pidd1(7)=' first datasets of successive days: '
numdays=numdays+1
;*************************************************************
; DAY - DAY COMPARISON
;*************************************************************
il=j
mmtimexs,il,j,nraz
wdelete,1
;******************************
; correlations
;******************************
cca(numdays, 6, 0)=correlate(oxdata,xdata)
cca(numdays, 6, 1)=correlate(oydata,ydata)
cca(numdays, 6, 2)=correlate(ozdata,zdata)
cca(numdays, 6, 3)=correlate(oxdata1,xdata1)
cca(numdays, 6, 4)=correlate(oydata1,ydata1)
cca(numdays, 6, 5)=correlate(ozdata1,zdata1)
cca(numdays, 6, 6)=correlate(oxdata2,xdata2)
cca(numdays, 6, 7)=correlate(oydata2,ydata2)
cca(numdays, 6, 8)=correlate(ozdata2,zdata2)
cca(numdays, 6, 9)=correlate(oxdata3,xdata3)
cca(numdays, 6, 10)=correlate(oydata3,ydata3)
cca(numdays, 6, 11)=correlate(ozdata3,zdata3)
cca(numdays, 6, 12)=correlate(opxdata,pxdata)
cca(numdays, 6, 13)=correlate(opydata,pydata)
cca(numdays, 6, 14)=correlate(opzdata,pzdata)
cca(numdays, 6, 15)=correlate(opxdata1,pxdata1)
cca(numdays, 6, 16)=correlate(opydata1,pydata1)
cca(numdays, 6, 17)=correlate(opzdata1,pzdata1)
```

```
Dec 20 1994 19:31:35                    ecgzx.pro                    Page 9
cca(numdays, 6, 18)=correlate(opxdata2,pxdata2)
cca(numdays, 6, 19)=correlate(opydata2,pydata2)
cca(numdays, 6, 20)=correlate(opzdata2,pzdata2)
cca(numdays, 6, 21)=correlate(opxdata3,pxdata3)
cca(numdays, 6, 22)=correlate(opydata3,pydata3)
cca(numdays, 6, 23)=correlate(opzdata3,pzdata3)
;*********************************************************
; day - day Differential Power Spectrum Plots
;*********************************************************
mmadiff6
for jj=0,14 do begin
ind=(j-1)*4
tables(jj,ind+3)=xr(234+jj)
tables(jj,ind+2)=xr(334+jj)
endfor
for jj=0,11 do begin
tables(jj+15,ind+3)=xr(162+jj)
tables(jj+15,ind+2)=xr(462+jj)
endfor
for jj=0,2 do begin
tables(27+jj,ind+3)=xr(429+jj)
tables(27+jj,ind+2)=xr(441+jj)
tables(30+jj,ind+3)=xr(478+jj)
tables(30+jj,ind+2)=xr(491+jj)
endfor
endif
jumpx:
;*********************************************************/
;        start intra day plots
;*********************************************************/
ref(corref)=s55
corref=corref+1
pidd9(0)=s55
xr(102)=xr(100)
xr(103)=xr(101)
if (j eq 1) then begin
OX=XDATA
OY=YDATA
OZ=ZDATA
OX1=XDATA1
OY1=YDATA1
OZ1=ZDATA1
OX1A=XDATA1A
OY1A=YDATA1A
OZ1A=ZDATA1A
OX2=XDATA2
OY2=YDATA2
OZ2=ZDATA2
OX3=XDATA3
OY3=YDATA3
OZ3=ZDATA3
OXN=XXDATA
OYN=YYDATA
OZN=ZZDATA
OVM2=VMDATA2
OVM=VMDATA
ok30=k3&ok40=k4&ox30=x3&ox40=x4
for i=0,14 do begin
```

| Dec 20 1994 19:31:35 | ecgzx.pro | Page 10 |
|---|---|---|

```
xr(300+i)=xr(i)
xr(350+i)=xr(i+50)
endfor
for i=0,5 do begin
xr(438+i)=xr(40+i)
xr(488+i)=xr(90+i)
endfor
OPX=PXDATA
OPY=PYDATA
OPZ=PZDATA
OPX1A=XDATA1A
OPY1A=YDATA1A
OPZ1A=ZDATA1A
OPX1=PXDATA1
OPX2=PXDATA2
OPX3=PXDATA3
OPY1=PYDATA1
OPY2=PYDATA2
OPY3=PYDATA3
OPZ1=PZDATA1
OPZ2=PZDATA2
OPZ3=PZDATA3
endif
;*********************************************************
;j eq 1: store 100
;*********************************************************
jj=(j-1)*4+3
tables(*,jj)=100.0
OXDATA=XDATA
OYDATA=YDATA
OZDATA=ZDATA
Xume(10,0,0:599)=xdata1a(0:599)
Xume(11,0,0:599)=ydata1a(0:599)
Xume(12,0,0:599)=zdata1a(0:599)
OXDATA1=XDATA1
OYDATA1=YDATA1
OZDATA1=ZDATA1
OXDATA2=XDATA2
OYDATA2=YDATA2
OZDATA2=ZDATA2
OXDATA3=XDATA3
OYDATA3=YDATA3
OZDATA3=ZDATA3
OXDATAN=XXDATA
OYDATAN=YYDATA
OZDATAN=ZZDATA
OVMDATA2=VMDATA2
OVMDATA=VMDATA
for i=0,14 do begin
xr(200+i)=xr(i)
xr(250+i)=xr(i+50)
endfor
for i=0,5 do begin
xr(425+i)=xr(40+i)
xr(475+i)=xr(90+i)
endfor
OPXDATA=PXDATA
OPYDATA=PYDATA
```

```
Dec 20 1994 19:31:35                    ecgzx.pro                         Page 11
OPZDATA=PZDATA
OPXDATA1=PXDATA1
OPXDATA2=PXDATA2
OPXDATA3=PXDATA3
OPYDATA1=PYDATA1
OPYDATA2=PYDATA2
OPYDATA3=PYDATA3
OPZDATA1=PZDATA1
OPZDATA2=PZDATA2
OPZDATA3=PZDATA3
endif
if (j gt 1) then begin
if (ecg eq lastecg) then begin
cca(numdays, 5,1)=cca(numdays,5,1)+1.0
pidd8(0)=s55
pidd1(7)=' Pre and Post CP '
;
;******************************************************
;            Time plots
;******************************************************
mmtimexs,il,j,nraz
wdelete,1
mmadiff6
for jj=0,14 do begin
ind=(j-1)*4
tables(jj,ind+3)=xr(234+jj)
tables(jj,ind+2)=xr(334+jj)
endfor
for jj=0,11 do begin
tables(jj+15,ind+3)=xr(162+jj)
tables(jj+15,ind+2)=xr(462+jj)
endfor
for jj=0,2 do begin
tables(27+jj,ind+3)=xr(428+jj)
tables(27+jj,ind+2)=xr(441+jj)
tables(30+jj,ind+3)=xr(478+jj)
tables(30+jj,ind+2)=xr(491+jj)
endfor
;***************************
; correlations
;***************************
dayset=fix(cca(numdays,5,1))
cca(numdays, dayset,  0)=correlate(oxdata,xdata)
cca(numdays, dayset,  1)=correlate(oydata,ydata)
cca(numdays, dayset,  2)=correlate(ozdata,zdata)
cca(numdays, dayset,  3)=correlate(oxdata1,xdata1)
cca(numdays, dayset,  4)=correlate(oydata1,ydata1)
cca(numdays, dayset,  5)=correlate(ozdata1,zdata1)
cca(numdays, dayset,  6)=correlate(oxdata2,xdata2)
cca(numdays, dayset,  7)=correlate(oydata2,ydata2)
cca(numdays, dayset,  8)=correlate(ozdata2,zdata2)
cca(numdays, dayset,  9)=correlate(oxdata3,xdata3)
cca(numdays, dayset, 10)=correlate(oydata3,ydata3)
cca(numdays, dayset, 11)=correlate(ozdata3,zdata3)
cca(numdays, dayset, 12)=correlate(opxdata,pxdata)
cca(numdays, dayset, 13)=correlate(opydata,pydata)
cca(numdays, dayset, 14)=correlate(opzdata,pzdata)
cca(numdays, dayset, 15)=correlate(opxdata1,pxdata1)
```

```
cca(numdays, dayset, 16)=correlate(opydata1,pydata1)
cca(numdays, dayset, 17)=correlate(opzdata1,pzdata1)
cca(numdays, dayset, 18)=correlate(opxdata2,pxdata2)
cca(numdays, dayset, 19)=correlate(opydata2,pydata2)
cca(numdays, dayset, 20)=correlate(opzdata2,pzdata2)
cca(numdays, dayset, 21)=correlate(opxdata3,pxdata3)
cca(numdays, dayset, 22)=correlate(opydata3,pydata3)
cca(numdays, dayset, 23)=correlate(opzdata3,pzdata3)
js=j-jk-1
XXD(js,0:599)=PXDATA(0:599)
YYD(js,0:599)=PYDATA(0:599)
ZZD(js,0:599)=PZDATA(0:599)
XXD1(js,0:599)=PXDATA1(0:599)
YYD1(js,0:599)=PYDATA1(0:599)
ZZD1(js,0:599)=PZDATA1(0:599)
XXD2(js,0:599)=PXDATA2(0:599)
YYD2(js,0:599)=PYDATA2(0:599)
ZZD2(js,0:599)=PZDATA2(0:599)
XXD3(js,0:599)=PXDATA3(0:599)
YYD3(js,0:599)=PYDATA3(0:599)
ZZD3(js,0:599)=PZDATA3(0:599)
Xume(0,js,0:599)=XDATA1A(0:599)
xume(1,js,0:599)=YDATA1A(0:599)
xume(2,js,0:599)=ZDATA1A(0:599)
XXD4(js,0:599)=XDATA1(0:599)
YYD4(js,0:599)=YDATA1(0:599)
ZZD4(js,0:599)=ZDATA1(0:599)
XXD5(js,0:599)=XDATA2(0:599)
YYD5(js,0:599)=YDATA2(0:599)
ZZD5(js,0:599)=ZDATA2(0:599)
XXD6(js,0:599)=XDATA3(0:599)
YYD6(js,0:599)=YDATA3(0:599)
ZZD6(js,0:599)=ZDATA3(0:599)
xume(20,js,0:599)=xume(20,0,0:599)
xume(21,js,0:599)=xume(21,0,0:599)
xume(22,js,0:599)=xume(22,0,0:599)
xume(23,js,0:599)=xume(23,0,0:599)
xume(24,js,0:599)=xume(24,0,0:599)
xume(25,js,0:599)=xume(25,0,0:599)
xume(26,js,0:599)=xume(26,0,0:599)
xume(27,js,0:599)=xume(27,0,0:599)
xume(28,js,0:599)=xume(28,0,0:599)
xume(29,js,0:599)=xume(29,0,0:599)
xume(30,js,0:599)=xume(30,0,0:599)
xume(31,js,0:599)=xume(31,0,0:599)
xume(32,js,0:599)=xume(32,0,0:599)
xume(33,js,0:599)=xume(33,0,0:599)
xume(34,js,0:599)=xume(34,0,0:599)
xume(35,js,0:599)=xume(35,0,0:599)
xume(36,js,0:599)=xume(36,0,0:599)
xume(37,js,0:599)=xume(37,0,0:599)
xume(38,js,0:599)=xume(38,0,0:599)
xume(39,js,0:599)=xume(39,0,0:599)
xume(40,js,0:599)=xume(40,0,0:599)
xume(41,js,0:599)=xume(41,0,0:599)
xume(42,js,0:599)=xume(42,0,0:599)
xume(43,js,0:599)=xume(43,0,0:599)
endif
```

61

| Dec 20 1994 19:31:35 | ecgzx.pro | Page 13 |

```
endif
;************************************************************
;END OF PROCESSING AND PLOTTING
;************************************************************
CLOSE, 1
wdelete,1
LASTECG=ECG
again=1
print,'fllllllllllllllaaaaaaaaggggg',number(k-1),j,flag00
ENDFOR
jn=j-jk-1;
pidd8(11)=pidd2
if jk ne 0 then begin
WINDOW, 0, colors=128, YPOS=80, XSIZE=1150, ySIZE=820, title=pidd
WINDOW, 5, colors=128, XSIZE=750, ypos=20,ySIZE=50, title=pidd
mmatdly0,jn;
PRINT, 'ENTER X TO EXIT OR ANY OTHER CHAR TO CONTINUE'
READ, xxxx
if( xxxx(0) eq nnn) then goto, jump1
mmadly0,jn;
endif $
else begin
mmatdly,jn;
PRINT, 'ENTER X TO EXIT OR ANY OTHER CHAR TO CONTINUE'
READ, xxxx
if( xxxx(0) eq nnn) then goto, jump1
mmadly2,jn;
endelse
pidd8(12)=''
PRINT, 'ENTER X TO EXIT OR ANY OTHER CHAR TO CONTINUE'
READ, xxxx
if( xxxx(0) eq nnn) then goto, jump1
if jk eq 0 then begin jkk=0&jk=j-1&endif else begin jkk=jk&jk=j-1&endelse
scorez,tables,nraz,jkk,jn,osd,osdk
PRINT, 'ENTER X TO EXIT OR ANY OTHER CHAR TO CONTINUE'
READ, xxxx
if( xxxx(0) eq nnn) then goto, jump1
scorefs2,oxs,jkk,jk-1,oxx,oxy,oxz
PRINT,'ENTER X TO EXIT OR ANY OTHER CHAR TO CONTINUE'
READ,xxxx
if (xxxx(0) eq nnn) then goto, jump1
wdelete,5
wdelete,0
if(j eq 2) then goto, jump2
for eeq=0,numdays do begin
ddset(eeq)=fix(cca(eeq,5,1))
endfor
numn=number(k-1)-jdiff
mmnorma, tables, numn,ddset,numdays
mmnorm, tables, numn,ddset,numdays
sdat='L'
eed=0
for eeq=0,numdays do begin
dayset=fix(cca(eeq,5,1))
if ( eeq gt 0) then begin
yyy=0.90
xx=-0.07
yyy=yyy-0.05
```

```
Dec 20 1994 19:31:35                    ecgzx.pro                         Page 14
yyy=yyy-0.05
yyy=yyy-0.05
for d11=0,23 do begin
if( d11 eq 12) then begin
yyy=yyy-0.05
yyy=yyy-0.05
xx=-0.07
endif
xx=xx+0.08
endfor
endif
if ( dayset gt 0) then begin
yyy=0.90
xx=-0.07
yyy=yyy-0.05
endif
if(eeq gt 0) then begin
eed=eed+cca(eeq-1,5,1)+1
endif
for dq=0,dayset-1 do begin
xx=-0.07
eeqqd=dq+1+eed
if eeqqd gt 10 then sd=sdat+s1(dq+1+eed) else sd=sdat+s1(0)+s1(eeqqd)
yyy=yyy-0.05
yyy=yyy-0.05
for d11=0,23 do begin
if( d11 eq 12) then begin
yyy=yyy-0.05
XYOUTS, 0.0, yyy, SIZE=0.9, 'Between Power Plots:', /Normal, /noclip,color
yyy=yyy-0.05
xx=-0.07
endif
xx=xx+0.08
XYOUTS, xx, yyy, SIZE=0.7, cca(eeq,dq+1,d11), /Normal, /noclip,color=127
endfor
yyy=yyy-0.20
endfor
again=1
endfor
jump2:
wdelete,0
;********************************************************
; STORE THE PARIENTS DATA IN TABLES
;********************************************************
mmtablesz,k,sdat,numdays,osd
close,1
close,2
wdelete,5
PRINT, 'END OF PROCESSING FOR: '+PAT
jumpat:
ENDFOR
;********************************************************
;End loop for patient
;********************************************************
jumpout:
again=1
jump1:
close,1
```

```
close,2
wdelete,5
wdelete,0
wdelete,1
SPAWN, 'rm *.lis'
END
```

--- scorez.pro — Dec 20 1994 19:29:09 — Page 1

```
;*****************************************************************
; THIS SUBROUTINE CALCULATES THE TEST SCORES FOR THE PATIENT
; COMPARED TO THE NORMAL POPULATION
;*****************************************************************
pro scorez,tables,nraz,jk,jn,osd,osdk
;*****************************************************************
; initialize arrays
;*****************************************************************
nst=28
rj=4*jk
rjj=rj+1
ss=fltarr(nst)
osd(osdk,0)=''
osd(osdk,1)=''
osd(osdk,2)=''
osd(osdk,3)=''
osd(osdk,4)=''
osd(osdk,5)=''
osd(osdk,6)=''
;*****************************************************************
;read the normal population mean and standard deviation
; for each test
;*****************************************************************
av=fltarr(nst)
av2=fltarr(nst)
get_lun,vb
openr,vb,'avg1'
non=0
readu,vb,non
readu,vb,av
readu,vb,av2
cc=fltarr(nst,non)
readu,vb,cc
cc2=intarr(nst)
close,vb
;*****************************************************************
;calculate the patient's scores in 28 tests by comparing with
; the mean and the standard deviation of the normals for
; each test
;*****************************************************************
ss(0)=(tables(0,rjj)-av(0))/av2(0)
if ss(0) ge 1 then begin $
xc=cc(0,*) ge tables(0,rjj)
xct=fix(total(xc)/non*100)
cc2(0)=xct
endif ss(1)=(av(1)-tables(3,rjj))/av2(1)
if ss(1) ge 1 then begin $
xc=cc(1,*) le tables(3,rjj)
xct=fix(total(xc)/non*100)
cc2(1)=xct
endif ss(2)=(tables(7,rjj)-av(2))/av2(2)
if ss(2) ge 1 then begin $
xc=cc(2,*) ge tables(7,rjj)
xct=fix(total(xc)/non*100)
```

64

| Dec 20 1994 19:29:09 | scorez.pro | Page 2 |

```
cc2(2)=xct
endif ss(3)=(tables(11,rjj)-av(3))/av2(3)
if ss(3) ge 1 then begin $
xc=cc(3,*) ge tables(11,rjj)
xct=fix(total(xc)/non*100)
cc2(3)=xct
endif ss(4)=(tables(1,rjj)-av(4))/av2(4)
gg=ss(4)&ss(4)=abs(ss(4))
if gg ge 1 then begin $
xc=cc(4,*) ge tables(1,rjj)
xct=fix(total(xc)/non*100)
cc2(4)=xct
endif else if gg le -1 then begin $
xc=cc(4,*) le tables(1,rjj)
xct=fix(total(xc)/non*100)
cc2(4)=xct
endif ss(5)=(tables(4,rjj)-av(5))/av2(5)
gg=ss(5)&ss(5)=abs(ss(5))
if gg ge 1 then begin $
xc=cc(5,*) ge tables(4,rjj)
xct=fix(total(xc)/non*100)
cc2(5)=xct
endif else if gg le -1 then begin $
xc=cc(5,*) le tables(4,rjj)
xct=fix(total(xc)/non*100)
cc2(5)=xct
endif ss(6)=(tables(8,rjj)-av(6))/av2(6)
if ss(6) ge 1 then begin $
xc=cc(6,*) ge tables(8,rjj)
xct=fix(total(xc)/non*100)
cc2(6)=xct
endif ss(7)=(tables(12,rjj)-av(7))/av2(7)
if ss(7) ge 1 then begin $
xc=cc(7,*) ge tables(12,rjj)
xct=fix(total(xc)/non*100)
cc2(7)=xct
endif ss(8)=(tables(2,rjj)-av(8))/av2(8)
if ss(8) ge 1 then begin $
xc=cc(8,*) ge tables(2,rjj)
xct=fix(total(xc)/non*100)
cc2(8)=xct
endif ss(9)=(av(9)-tables(5,rjj))/av2(9)
if ss(9) ge 1 then begin $
xc=cc(9,*) le tables(5,rjj)
```

```
Dec 20 1994 19:29:09                scorez.pro                        Page 3 xct=fix(total(xc)/non*100)
cc2(9)=xct
endif ss(10)=(av(10)-tables(9,rjj))/av2(10)
if ss(10) ge 1 then begin $
xc=cc(10,*) le tables(9,rjj)
xct=fix(total(xc)/non*100)
cc2(10)=xct
endif ss(11)=(av(11)-tables(13,rjj))/av2(11)
if ss(11) ge 1 then begin $
xc=cc(11,*) le tables(13,rjj)
xct=fix(total(xc)/non*100)
cc2(11)=xct
endif ss(12)=(av(12)-tables(0,rj))/av2(12)
if ss(12) ge 1 then begin $
xc=cc(12,*) le tables(0,rj)
xct=fix(total(xc)/non*100)
cc2(12)=xct
endif ss(13)=(av(13)-tables(3,rj))/av2(13)
if ss(13) ge 1 then begin $
xc=cc(13,*) le tables(3,rj)
xct=fix(total(xc)/non*100)
cc2(13)=xct
endif ss(14)=(av(14)-tables(7,rj))/av2(14)
if ss(14) ge 1 then begin $
xc=cc(14,*) le tables(7,rj)
xct=fix(total(xc)/non*100)
cc2(14)=xct
endif ss(15)=(av(15)-tables(27,rj))/av2(15)
if ss(15) ge 1 then begin $
xc=cc(15,*) le tables(27,rj)
xct=fix(total(xc)/non*100)
cc2(15)=xct
endif xg=tables(27,rj)/tables(28,rj)
ss(16)=(xg-av(16))/av2(16)
if ss(16) ge 1 then begin $
xc=cc(16,*) ge xg
xct=fix(total(xc)/non*100)
cc2(16)=xct
endif ss(17)=(av(17)-tables(1,rj))/av2(17)
if ss(17) ge 1 then begin $
xc=cc(17,*) le tables(1,rj)
xct=fix(total(xc)/non*100)
```

```
cc2(17)=xct
endif ss(18)=(av(18)-tables(4,rj))/av2(18)
if ss(18) ge 1 then begin $
xc=cc(18,*) le tables(4,rj)
xct=fix(total(xc)/non*100)
cc2(18)=xct
endif ss(19)=(av(19)-tables(8,rj))/av2(19)
if ss(19) ge 1 then begin $
xc=cc(19,*) le tables(8,rj)
xct=fix(total(xc)/non*100)
cc2(19)=xct
endif ss(20)=(av(20)-tables(12,rj))/av2(20)
if ss(20) ge 1 then begin $
xc=cc(20,*) le tables(12,rj)
xct=fix(total(xc)/non*100)
cc2(20)=xct
endif ss(21)=(av(21)-tables(28,rj))/av2(21)
if ss(21) ge 1 then begin $
xc=cc(21,*) le tables(28,rj)
xct=fix(total(xc)/non*100)
cc2(21)=xct
endif xg=tables(28,rj)/tables(29,rj)
ss(22)=(av(22)-xg)/av2(22)
if ss(22) ge 1 then begin $
xc=cc(22,*) le xg
xct=fix(total(xc)/non*100)
cc2(22)=xct
endif ss(23)=(tables(2,rj)-av(23))/av2(23)
if ss(23) ge 1 then begin $
xc=cc(23,*) ge tables(2,rj)
xct=fix(total(xc)/non*100)
cc2(23)=xct
endif ss(24)=(av(24)-tables(9,rj))/av2(24)
if ss(24) ge 1 then begin $
xc=cc(24,*) le tables(9,rj)
xct=fix(total(xc)/non*100)
cc2(24)=xct
endif ss(25)=(av(25)-tables(13,rj))/av2(25)
if ss(25) ge 1 then begin $
xc=cc(25,*) le tables(13,rj)
xct=fix(total(xc)/non*100)
```

```
cc2(25)=xct
endif ss(26)=(tables(29,rj)-av(26))/av2(26)
if ss(26) ge 1 then begin $
xc=cc(26,*) ge tables(29,rj)
xct=fix(total(xc)/non*100)
cc2(26)=xct
endif xg=tables(27,rj)/tables(29,rj)
ss(27)=(av(27)-xg)/av2(27)
if ss(27) ge 1 then begin $
xc=cc(27,*) le xg
xct=fix(total(xc)/non*100)
cc2(27)=xct
endif
;****************************************************************
;store the test scores for the patient
;****************************************************************
xc2=strarr(nst)
p=strarr(nst)
ss1=ss gt 1
ss9=fix(ss*ss1)
trt=0
for j=0,27 do begin
if ss9(j) lt 1 then begin $
xc2(j)='     '
endif else  begin $
xc2(j)=strtrim(string(cc2(j)),1)+'   '
if cc2(j) lt 5 then trt=trt+ss9(j)
endelse
endfor ms=intarr(4)&md=intarr(2)
vs=strarr(nst)
for i=0,27 do vs(i)=strtrim(string(ss9(i)),2)
osd(osdk,0)=vs(12)+' '+vs(13)+' '+vs(14)+'     '+vs(15)+'   '+vs(16)+$
'       '+vs(17)+' '+vs(18)+' '+vs(19)+'   '+vs(20)+' '+vs(21)+'   '+vs(22) 
'       '+vs(23)+'   '+vs(24)+' '+vs(25)+'   '+vs(26)+'   '+vs(27)+$
'       '+string(trt)

osd(osdk,5)=vs(0)+'   '+vs(1)+'   '+vs(2)+' '+vs(3)+'              '+$
vs(4)+' '+vs(5)+'   '+vs(6)+'   '+vs(7)+'              '+$
vs(8)+'   '+vs(9)+'   '+vs(10)+'   '+vs(11)

for i=0,27 do p(i)=strmid(xc2(i),0,3)
osd(osdk,4)=p(12)+p(13)+p(14)+'   '+p(15)+p(16)+$
'    '+p(17)+p(18)+p(19)+p(20)+p(21)+p(22)+$
'    '+p(23)+'   '+p(24)+p(25)+p(26)+p(27)
osd(osdk,6)=p(0)+p(1)+p(2)+p(3)+$
'          '+p(4)+p(5)+p(6)+p(7)+$
'          '+p(8)+p(9)+p(10)+p(11)
return
end
```

| Dec 20 1994 19:34:31 | mmfilter62.pro | Page 1 |

```
;*********************************************************
;THIS SUBROUTINE FILTERS THE X,Y;Z SIGNALS INTO 4 BANDS : 0-10 Hz,
; 10-60 Hz, 60-150 Hz, and 150-250 Hz
;*********************************************************
PRO MMFILTER6
;*********************************************************
; INITIALIZE ARRAYS
;*********************************************************
COMMON SP1,  K3, K4, X3, X4, K3D, K4D
COMMON SP2,  PXDATA, PYDATA, PZDATA, PXDATA1, PXDATA2, PXDATA3, PYDATA1
COMMON SP3,  PYDATA2, PZDATA2, PZDATA1, PYDATA3, PZDATA3, XQATA, YDATA, ZDA
COMMON SP4,  pidd0
COMMON SP5,  XDATA1, YDATA1, ZDATA1, XDATA2, YDATA2, ZDATA2, XDATA3,YDATA3,
COMMON SP6,  VMDATA2, pid,piddl,pidd2,pidd3,pidd4,pidd5,pidd6,pidd7,pidd8,p
COMMON SP7,  VMDATA
COMMON SP8,  XR
COMMON SP9,  OXDATA, OYDATA, OZDATA, OXDATA1, OXDATA2,OXDATA3, OXDATAN,OVMD
COMMON SP10, OVMDATA, OYDATA1,OYDATA2,OYDATA3,OZDATA1,OZDATA2,OZDATA3,OYDA
COMMON SP11, OZDATAN, OPXDATA1,OPXDATA2,OPXDATA3,OPXDATA, OPYDATA,OPYDATA1
COMMON SP12, OPYDATA2,OPYDATA3, OPZDATA,OPZDATA1,OPZDATA2,OPZDATA3
COMMON SP13, PIDDA
COMMON SP16, XDATA1A,YDATA1A,ZDATA1A,XXD,YYD,ZZD,XXD1,YYD1,ZZD1,XXD2,YYD2,
OUARR=FLTARR(4,600)
k3=FLTARR(600)
k4=FLTARR(600)
X3=FLTARR(600)
x4=FLTARR(600)
XINDEX=INTARR(600)
XINDEX2=INTARR(150)
XINDEX3=INTARR(256)
XINDEX4=INTARR(100)
IDATA=INTARR(2096)
xxxx=STRARR(1)
piddc=pidd+'   '+pidd0
id1=fix(xr(100))
id2=fix(xr(101))
scale1=25.0
scale2=2.0
scale3=0.5
for i=0,599 do begin
xindex(i)=i
endfor
smooth,xdata
smooth,ydata
smooth,zdata
xr(40)=rms(xdata,id1,id2)
xr(41)=rms(ydata,id1,id2)
xr(42)=rms(zdata,id1,id2)
xr(85)=rms(xdata,1,id1)
xr(86)=rms(ydata,1,id1)
xr(87)=rms(zdata,1,id1)
;*********************************************************
;FILTER INTO THE 0-10 Hz and 10-60 Hz bands
;*********************************************************
nn=70
vnbc=digital_filter(0.02,0.12,70,nn)
xdata1=padcon(xdata,vnbc,nn)
xr(3)=rms(xdata1,id1,id2)
```

| Dec 20 1994 19:34:31 | mmfilter62.pro | Page 2 |

```
vnbc1=digital_filter(0.0,0.02,70,nn)
xdata1a=padcon(xdata,vnbc1,nn)
xr(0)=rms(xdata1a,id1,id2)
ydata1=padcon(ydata,vnbc,nn)
xr(4)=rms(ydata1,id1,id2)
ydata1a=padcon(ydata,vnbc1,nn)
xr(1)=rms(ydata1a,id1,id2)
zdata1=padcon(zdata,vnbc,nn)
xr(5)=rms(zdata1,id1,id2)
zdata1a=padcon(zdata,vnbc1,nn)
xr(2)=rms(zdata1a,id1,id2)
xr(88)=rms(xdata1,1,id1)
xr(89)=rms(ydata1,1,id1)
xr(90)=rms(zdata1,1,id1)
xr(91)=rms(xdata1a,1,id1)
xr(92)=rms(ydata1a,1,id1)
xr(93)=rms(zdata1a,1,id1)
VMDATA=VECT(XDATA1, YDATA1, ZDATA1)
xr(6)=rms(vmdata,id1,id2)
;******************************************************
;FILTER INTO THE 60-150 Hz band
;******************************************************
vnbc=digital_filter(0.12,0.3,70,nn)
xdata2=padcon(xdata,vnbc,nn)
xr(7)=rms(xdata2,id1,id2)
ydata2=padcon(ydata,vnbc,nn)
xr(8)=rms(ydata2,id1,id2)
zdata2=padcon(zdata,vnbc,nn)
xr(9)=rms(zdata2,id1,id2)
xr(94)=rms(xdata2,1,id1)
xr(95)=rms(ydata2,1,id1)
xr(96)=rms(zdata2,1,id1)
VMDATA=VECT(XDATA2, YDATA2, ZDATA2)
VMDATA2=VMDATA
xr(10)=rms(vmdata,id1,id2)
;******************************************************
;FILTER INTO THE 150-250 Hz band
;******************************************************
vnbc=digital_filter(0.3,0.5,70,nn)
xdata3=padcon(xdata,vnbc,nn)
xr(11)=rms(xdata3,id1,id2)
ydata3=padcon(ydata,vnbc,nn)
xr(12)=rms(ydata3,id1,id2)
zdata3=padcon(zdata,vnbc,nn)
xr(13)=rms(zdata3,id1,id2)
xr(97)=rms(xdata3,1,id1)
xr(98)=rms(ydata3,1,id1)
xr(99)=rms(zdata3,1,id1)
VMDATA=VECT(XDATA3, YDATA3, ZDATA3)
;******************************************************
;STORE THE FILTERED SIGNALS
;******************************************************
xr(14)=rms(vmdata,id1,id2)
xtot=xr(3)+xr(7)+xr(11)+xr(0)
ytot=xr(4)+xr(8)+xr(12)+xr(1)
ztot=xr(5)+xr(9)+xr(13)+xr(2)
xr(15)=xr(3)/xr(40)*100.0
xr(16)=xr(3)/xtot*100.0
```

| Dec 20 1994 19:34:31 | mmfilter62.pro | Page 3 |
|---|---|---|

```
xr(17)=xr(4)/xr(41)*100.0
xr(18)=xr(4)/ytot*100.0
xr(19)=xr(5)/xr(42)*100.0
xr(20)=xr(5)/ztot*100.0
xr(43)=xr(0)/xtot*100.0
xr(44)=xr(1)/ytot*100.0
xr(45)=xr(2)/ztot*100.0
vtot=xr(6)+xr(10)+xr(14)
xr(15)=xr(6)/vtot*100.0
xr(17)=xr(10)/vtot*100.0
xr(19)=xr(14)/vtot*100.0
xr(21)=xr(7)/xr(40)*100.0
xr(22)=xr(7)/xtot*100.0
xr(23)=xr(8)/xr(41)*100.0
xr(24)=xr(8)/ytot*100.0
xr(25)=xr(9)/xr(42)*100.0
xr(26)=xr(9)/ztot*100.0
xr(27)=xr(11)/xr(40)*100.0
xr(28)=xr(11)/xtot*100.0
xr(29)=xr(12)/xr(41)*100.0
xr(30)=xr(12)/ytot*100.0
xr(31)=xr(13)/xr(42)*100.0
xr(32)=xr(13)/ztot*100.0
xr(40)=xtot
xr(41)=ytot
xr(42)=ztot
RETURN
END
```

Dec 20 1994 20:31:15　　　　　　　　　avgasc

NORMAL POPULATION MEANS AND STANDARD DEVIATIONS

| | MEAN | STANDARD DEVIATION |
|---|---|---|
| P1  | 571.083  | 144.154 |
| P2  | 246.654  | 74.5161 |
| P3  | 305.662  | 75.3298 |
| P4  | 15.7657  | 7.11228 |
| P5  | 2.98628  | 1.36906 |
| P6  | 624.600  | 183.909 |
| P7  | 280.751  | 99.2970 |
| P8  | 316.841  | 90.4057 |
| P9  | 22.3901  | 9.04580 |
| P10 | 4.67559  | 1.66451 |
| P11 | 369.992  | 132.695 |
| P12 | 150.003  | 68.3454 |
| P13 | 202.886  | 71.2716 |
| P14 | 14.2006  | 5.63649 |
| P15 | 2.91297  | 1.66451 |
| P16 | 42.8821  | 4.66601 |
| P17 | 53.7869  | 4.29935 |
| P18 | 2.79821  | 1.09847 |
| P19 | 0.528566 | 0.198347 |
| P20 | 44.3372  | 5.17700 |
| P21 | 51.0766  | 4.81893 |
| P22 | 3.78138  | 1.53050 |
| P23 | 0.797841 | 0.337331 |
| P24 | 39.5841  | 7.12802 |
| P25 | 55.3434  | 6.17960 |
| P26 | 4.19738  | 1.94699 |
| P27 | 0.870097 | 0.414340 |
| P28 | 0.982148 | 0.347569 |
| P29 | 1.89206  | 0.821214 |
| P30 | 1.74804  | 0.753290 |

(NOTE: THE P1 - P30 DESIGNATIONS CORRESPOND TO
THE IDENTIFICATIONS IN THE TEXT OF THE DISCLOSURE)

| NORM | BEMO | BEST | BNOB | BTEST | BGENSIA | BVAS | BTNR | BMAQ | BEXE | STEP |
|---|---|---|---|---|---|---|---|---|---|---|
| 100 | 100 | 100 | 100 | 100 | 100 | 100 | 100 | 100 | 100 | 0 |
| 53.7931 | 97.222 | 95.96 | 94.059 | 97.674 | 95.455 | 92 | 58.333 | 80.263 | 92.857 | 1 |
| 41.3793 | 95.37 | 91.919 | 93.069 | 94.186 | 90.909 | 84 | 36.111 | 67.105 | 71.429 | 2 |
| 28.2759 | 92.593 | 84.849 | 90.099 | 93.023 | 89.394 | 84 | 25 | 50 | 64.286 | 3 |
| 19.3103 | 91.667 | 83.838 | 84.158 | 90.698 | 89.394 | 84 | 25 | 43.421 | 64.286 | 4 |
| 11.7241 | 87.963 | 81.818 | 78.218 | 87.209 | 87.879 | 84 | 25 | 34.211 | 60.714 | 5 |
| 10.3448 | 84.259 | 76.768 | 71.287 | 84.884 | 86.364 | 80 | 22.222 | 28.947 | 60.714 | 6 |
| 8.27586 | 82.407 | 72.727 | 68.317 | 81.395 | 80.303 | 76 | 22.222 | 23.684 | 53.571 | 7 |
| 6.89655 | 78.704 | 69.697 | 59.406 | 79.07 | 78.788 | 72 | 8.333 | 19.737 | 46.429 | 8 |
| 6.2069 | 75.926 | 66.667 | 56.436 | 74.419 | 75.758 | 72 | 8.333 | 14.474 | 42.857 | 9 |
| 4.82759 | 72.222 | 64.647 | 50.495 | 69.767 | 71.212 | 64 | 2.778 | 11.842 | 42.857 | 10 |
| 3.44828 | 67.593 | 62.626 | 46.535 | 66.279 | 62.121 | 60 | 2.778 | 11.842 | 42.857 | 11 |
| 2.75862 | 64.815 | 58.586 | 45.545 | 62.791 | 59.091 | 52 | 2.778 | 10.526 | 42.857 | 12 |
| 2.06897 | 61.111 | 56.566 | 45.545 | 58.14 | 51.515 | 48 | 2.778 | 7.895 | 32.143 | 13 |
| 2.06897 | 59.259 | 51.515 | 42.574 | 56.977 | 46.97 | 36 | 2.778 | 7.895 | 28.571 | 14 |
| 1.37931 | 57.407 | 49.495 | 38.614 | 54.651 | 46.97 | 32 | 0 | 7.895 | 21.429 | 15 |
| 0.689655 | 51.852 | 45.455 | 35.644 | 50 | 40.909 | 32 | 0 | 7.895 | 17.857 | 16 |
| 0.689655 | 48.148 | 41.414 | 31.683 | 41.861 | 36.364 | 32 | 0 | 6.579 | 17.857 | 17 |
| 0 | 46.296 | 39.394 | 25.743 | 37.209 | 30.303 | 32 | 0 | 5.263 | 14.286 | 18 |
| 0 | 44.444 | 36.364 | 20.792 | 36.047 | 28.788 | 32 | 0 | 5.263 | 14.286 | 19 |
| 0 | 43.519 | 32.323 | 15.842 | 33.721 | 27.273 | 28 | 0 | 5.263 | 14.286 | 20 |
| 0 | 38.889 | 29.293 | 14.852 | 27.907 | 22.727 | 24 | 0 | 3.947 | 14.286 | 21 |
| 0 | 37.037 | 27.273 | 12.871 | 26.744 | 19.697 | 24 | 0 | 2.632 | 14.286 | 22 |
| 0 | 34.259 | 25.253 | 10.891 | 25.581 | 19.697 | 24 | 0 | 2.632 | 10.714 | 23 |
| 0 | 32.407 | 23.232 | 9.901 | 22.093 | 16.667 | 20 | 0 | 1.316 | 10.714 | 24 |
| 0 | 25 | 21.212 | 9.901 | 16.279 | 13.636 | 20 | 0 | 1.316 | 10.714 | 25 |
| 0 | 23.148 | 21.212 | 8.911 | 16.279 | 13.636 | 20 | 0 | 1.316 | 10.714 | 26 |
| 0 | 22.222 | 20.202 | 7.921 | 16.279 | 10.606 | 12 | 0 | 1.316 | 10.714 | 27 |
| 0 | 22.222 | 19.192 | 7.921 | 12.791 | 10.606 | 12 | 0 | 1.316 | 7.143 | 28 |
| 0 | 17.593 | 17.172 | 6.931 | 12.791 | 7.576 | 8 | 0 | 1.316 | 7.143 | 29 |
| 0 | 14.815 | 14.141 | 6.931 | 11.628 | 7.576 | 8 | 0 | 1.316 | 7.143 | 30 |
| 0 | 13.889 | 12.121 | 6.931 | 11.628 | 4.545 | 8 | 0 | 1.316 | 7.143 | 31 |
| 0 | 12.963 | 10.101 | 2.97 | 11.628 | 3.03 | 8 | 0 | 1.316 | 7.143 | 32 |
| 0 | 10.185 | 9.091 | 1.98 | 10.465 | 1.515 | 8 | 0 | 1.316 | 7.143 | 33 |
| 0 | 10.185 | 8.081 | 1.98 | 8.14 | 1.515 | 8 | 0 | 1.316 | 3.571 | 34 |
| 0 | 7.407 | 8.081 | 1.98 | 8.14 | 1.515 | 8 | 0 | 1.316 | 3.571 | 35 |
| 0 | 5.556 | 6.061 | 1.98 | 8.14 | 1.515 | 4 | 0 | 1.316 | 3.571 | 36 |
| 0 | 5.556 | 5.051 | 0.99 | 8.14 | 1.515 | 4 | 0 | 1.316 | 3.571 | 37 |
| 0 | 4.63 | 5.051 | 0.99 | 8.14 | 1.515 | 4 | 0 | 0 | 3.571 | 38 |
| 0 | 3.704 | 4.04 | 0 | 6.977 | 1.515 | 0 | 0 | 0 | 3.571 | 39 |
| 0 | 3.704 | 4.04 | 0 | 6.977 | 1.515 | 0 | 0 | 0 | 3.571 | 40 |

It is also disclosed that Tracking of a subject can be continuous, and can utilize data obtained before and after, for instance: a suitable stress test; intervention (angioplasty etc.); and/or medical therapy. Of interest is the fact that signal magnitude in Frequency Domain Plots, (eg. 7aX1–7aZ5), particulary in 60–150 and 150–250 HZ ranges has routinely been noted to drop by thirty (30%) percent or more upon subjecting patients who are prone to ischemia, to a cold-pressor test.

It is also to be understood that the terminology "Coronary Artery Disease" is used throughout this Disclosure, the present invention serves to identify Coronary Disfunction generally, which can include myocaridal poblems separate from Coronary Artery disease per se.

Finally, it is generally described herein that, for instance, as differences between Normal Subject Population, and Subject Representative Parameters increase, the "Score" of the present invention increases. It would be a simple matter indeed to place a negative sign on the "Score" and declare that it "decreases" when differences between Normal Subject Population and Subject Representative Parameters increase. It would further be a simple matter to utilize slightly different but substantially the same Normal Subject Population, and Subject Data Frequency Bands, or select slightly different but substantially the same Normal Subject Population, and Subject Data (ECG) cycle portions. As to attempt to draft definite claim language to overcome all such possibilities would be an impossible task in view of the complexity of the present invention subject matter, it is therefore to be understood that the Doctrine of Equivalent applies to, and the claims are to be interpreted to include all such contrived and substantially indifferent functional equivalents in the practice of the recited method of the present invention, emphasis added.

Having hereby disclosed the subject matter of the present invention, it should be obvious that many modifications, substitutions and variations of the present invention are possible in light of the teachings. It is therefore to be understood that the invention may be practiced other than as specifically described, and should be limited in breadth and scope only by the claims.

I claim:

1. An ECG system for practicing a noninvasive method of investigating cardiac status of a subject and enabling classification of said subject into normal and abnormal cardiac categories utilizing electrocardiography ECG data obtained therefrom, said method comprising, in a functional sequence, performance of the steps of:

a. obtaining data from ECG cycle(s) from each of a multiplicity of members of a population of subjects who have been documented as normal subjects, in that they do not show risk factors for, or demonstrate detectable cardiac abnormality, by providing, selecting and monitoring at least one lead(s) of said ECG system;

b. establishing criteria for, and in line therewith selecting some ECG cycle portion and defining cycle portion data points therewithin, and calculating an average selected ECG cycle portion data set for said at least one monitored ECG system lead(s) by, for a monitored ECG system lead, a procedure comprising combining corresponding ECG cycle portion data points for said selected ECG cycle portion for ECG cycle(s) obtained from each of a number of members of said multiplicity of members of a population of subjects who have been documented as normal subjects, each said calculated average selected ECG cycle portion data set being a composite data set of said selected ECG cycle portion for said population of normal subjects, for a monitored ECG system lead;

c. obtaining data from ECG cycle(s) from a subject, by monitoring at least one lead(s) of said ECG system, said ECG system lead(s) monitored being the same as the monitored ECG system lead(s) utilized in step a. to obtain data utilized in step b.;

d. selecting some ECG cycle portion, which is essentially that selected in step b., and calculating an average selected ECG cycle portion data set for said at least one monitored ECG system lead(s) by, for a monitored ECG system lead, a procedure comprising combining corresponding ECG cycle portion data points for said selected ECG cycle portion for ECG cycle(s) obtained from said subject, each said calculated average selected ECG cycle portion data set being a composite data set of said selected ECG cycle portion for said subject, for a monitored ECG system lead;

e. calculating corresponding representative parameter(s) from resulting composite data sets calculated in steps b. and d., for monitored ECG system lead(s), for, respectively, said normal subject population and said subject;

f. comparing subject to corresponding normal subject population representative parameter(s), and combining results thereof to arrive at a "score", the magnitude of which "score" results from difference(s) between magnitude(s) of corresponding normal subject population, and subject representative parameter(s), which "score" magnitude increases when said difference(s) in magnitude(s) between corresponding normal subject population, and subject, representative parameter(s) increase, the magnitude of which "score" provides an indication of the cardiac status of said subject, with a "score" near zero being indicative of a subject properly categorized as a cardiac normal in that the magnitude(s) of subject representative parameter(s) are generally more closely matched to the magnitude(s) of corresponding normal subject population representative parameter(s), and with a progressively higher "score" being indicative of a subject progressively more properly categorized as a cardiac abnormal in that the magnitude(s) of subject representative parameter(s) are generally progressively less closely matched to the magnitude(s) of corresponding normal subject population representative parameter(s);

g. providing an output means for presenting said score; said ECG system comprising ECG lead(s) which monitor electrodes affixed to a subject or member of a normal subject population, and which provide monitored signal(s) to an ECG monitor, said ECG monitor being functionally interconnected to a computational means which is programmed to accept ECG data from said ECG monitor and practice the method of steps a.–f., said computational means being functionally interconnected to an output means to enable practice of step g.

2. A system for practicing a noninvasive method of investigating cardiac status of a subject and enabling classification of a subject into normal and abnormal cardiac categories utilizing electrocardiography ECG data obtained therefrom as in claim 1, which method further comprises performance of the additional steps of calculating, and comparing ratio(s) of subject, to corresponding ratio(s) of normal subject population, representative parameters, and combining results thereof with those from comparing subject to corresponding normal subject population, representative parameter(s), in arriving at said "score", the magnitude of which "score" then further results from difference(s) between magnitude(s) of corresponding normal subject population and subject ratio(s) of representative parameters, which "score" magnitude increases when difference(s) in magnitude(s) between corresponding normal subject population, and subject, ratio(s) of representative parameters increase;

said ECG system computational means being programmed to perform said additional steps.

3. An ECG system for practicing a noninvasive method of investigating cardiac status of a subject and enabling classification of said subject into normal and abnormal cardiac categories utilizing electrocardiography ECG data obtained therefrom as in claim 1, which method further comprises performance of the additional steps of:

a. providing at least one coordinate system selected from the group consisting of magnitude vs. time, and magnitude vs. frequency;

b. for an ECG cycle portion, performing calculations necessary to plot and display and plotting and displaying normal subject population and subject ECG data as a function of at least one parameter selected from the group consisting of time and frequency, to respectively provide as desired, visually interpretable plots of ECG magnitude and power spectral density data, observation of which provides an indication of the cardiac status of said subject; and c. observing and interpreting the displayed plot(s);

said ECG system computational means being programmed to perform said additional step and cause display thereof via output display means.

4. An ECG system for practicing a noninvasive method of investigating cardiac status of a subject and enabling classification of said subject into normal and abnormal cardiac categories utilizing electrocardiography ECG data obtained therefrom, said method comprising, in a functional sequence, performance of the steps of:

a. obtaining data from ECG cycle(s) from each of a multiplicity of members of a population of subjects who have been documented as normal subjects, in that they do not show risk factors for, or demonstrate detectable cardiac abnormality, by providing, selecting and monitoring at least one lead(s) of said ECG system;

b. establishing criteria for, and in line therewith selecting some ECG cycle portion, and defining cycle portion data points therewithin, and calculating an average selected ECG cycle portion data set for at least one monitored ECG system lead(s) by, for a monitored ECG system lead, a procedure comprising combining corresponding ECG cycle portion data points for said selected ECG cycle portion for ECG cycle(s) obtained from each of a number of members of said multiplicity of members of a population of subjects who have been documented as normal subjects, each said calculated average selected ECG cycle portion data set being a composite data set of said selected ECG cycle portion for said population of normal subjects, for a monitored ECG system lead;

c. obtaining data from ECG cycle(s) from a subject, by monitoring at least one lead(s) of ECG said system, said ECG system lead(s) monitored being the same as the monitored ECG system lead(s) utilized in step a. to obtain data utilized in step b.;

d. selecting some ECG cycle portion, which is essentially that selected in step b., and calculating an average selected ECG cycle portion data set for said at least one monitored ECG system lead(s) by, for a monitored ECG system lead, a procedure comprising combining corresponding ECG cycle portion data points for said selected cycle portion for ECG cycle(s) obtained from said subject, each said calculated average selected ECG cycle portion data set being a composite data set of said selected ECG cycle portion for said subject, for a monitored ECG system lead;

e. calculating corresponding representative parameter(s) and corresponding ratio(s) involving representative parameters from resulting composite data sets calculated in steps b. and d., for monitored ECG system lead(s), for, respectively, said normal subject population and said subject;

f. comparing specific ratio(s) of subject to corresponding specific ratio(s) of normal subject population representative parameters, and combining results thereof to arrive at a "score", the magnitude of which "score" results from difference(s) between magnitude(s) of specific corresponding ratio(s) of normal subject population, and ratio(s) of subject representative parameters, which "score" magnitude increases when said difference(s) in magnitude(s) between specific ratio(s) of corresponding normal subject population, and specific ratio(s) of subject representative parameters increase, the magnitude of which "score" provides an indication of the cardiac status of said subject, with a "score" near zero being indicative of a subject properly categorized as a cardiac normal in that the magnitude(s) of ratio(s) of subject representative parameters are generally more closely matched to the magnitude(s) of corresponding ratio(s) of normal subject population representative parameters, and with a progressively higher "score" being indicative of a subject progressively more properly categorized as a cardiac abnormal in that the magnitude(s) of ratio(s) of subject representative parameters are generally progressively less closely matched to the magnitude(s) of ratio(s) of corresponding normal subject population representative parameters;

g. providing an output means for presenting said score;

said ECG system comprising ECG lead(s) which monitor electrodes affixed to a subject or member of a normal subject population, and which provide monitored signal(s) to an ECG monitor, said ECG monitor being functionally interconnected to a computational means which is programmed to accent ECG data from said ECG monitor and practice the method of steps a.–f. said computational means being functionally interconnected to an output means to enable practice of step g.

5. An ECG system for practicing a noninvasive method of investigating cardiac status of a subject and enabling classification of said subject into normal and abnormal cardiac categories utilizing electrocardiography ECG data obtained therefrom as in claim 7, which method further comprises performance of the additional steps of:

a. providing at least one coordinate system selected from the group consisting of magnitude vs. time, and magnitude vs. frequency;

b. for an ECG cycle portion, performing calculations necessary to plot and display and plotting and displaying normal subject population and subject ECG data, as a function of at least one parameter selected from the group consisting of time and frequency, to respectively provide as desired, visually interpretable plots of ECG magnitude and power spectral density data, observation of which provides an indication of the cardiac status of said subject; and c. observing and interpreting displayed plot(s);

said ECG system computational means being programmed to perform said additional step and cause display thereof via output display means.

6. An ECG system for practicing a noninvasive method of investigating cardiac status of a subject and enabling classification of said subject into normal and abnormal cardiac categories utilizing electrocardiography ECG data obtained therefrom, said method comprising, in a functional sequence, performance of the steps of:

a. obtaining data from ECG cycle(s) from each of a multiplicity of members of a population of subjects who have been documented as normal subjects, in that they do not show risk factors for, or demonstrate detectable cardiac abnormality, by providing, selecting and monitoring at least one lead(s) of an ECG system;

b. establishing criteria for, and in line therewith selecting some ECG cycle portion and defining cycle portion data points therewithin, and calculating an average selected ECG cycle portion data set for said at least one monitored ECG system lead(s), by, for a monitored ECG system lead, a procedure comprising combining corresponding ECG cycle portion data points for said selected ECG cycle portion for ECG cycle(s) obtained from each of a number of said multiplicity of members of a population of subjects who have been documented as normal subjects, and selecting a plurality of frequency bands and applying filtering techniques, to provide a plurality of data sets for each said at least one ECG system lead(s) monitored, each said data set being a composite data set of said selected ECG cycle portion for said population of normal subjects in a monitored lead and selected frequency band range;

c. obtaining data from ECG cycle(s) from a subject, by monitoring at least one lead(s) of said ECG system, said ECG system lead(s) monitored being the same as the monitored ECG system lead(s) utilized in step a. to obtain data utilized in step b.;

d. selecting some ECG cycle portion, said ECG cycle portion being essentially that selected in step b. for said normal subject population, and calculating an average selected ECG cycle portion data set for said at least one monitored ECG system lead(s), by, for a monitored ECG system lead, a procedure comprising combining corresponding ECG cycle portion data points for said selected ECG cycle portion for subject ECG cycle(s), and selecting a plurality of frequency bands, said selected frequency bands being essentially those selected in step b. for said normal subject population, and applying filtering techniques which are essentially those applied in step b. for said normal subject population, to provide a plurality of data sets for each said at least one monitored ECG system lead(s), each said data set being a composite data set of said selected ECG cycle portion for said subject in a monitored lead and selected frequency band range; p1 e. calculating corresponding representative parameter(s) from resulting composite data sets calculated in steps b. and d., in said selected frequency band ranges for monitored ECG system lead(s), for respectively, said normal subject population and said subject;

f. comparing specific subject to specific normal subject population corresponding representative parameter(s), and combining results thereof to arrive at a "score", the magnitude of which "score" results from difference(s) between magnitude(s) of corresponding normal subject population and subject representative parameter(s), which "score" magnitude increases when said difference(s) in magnitude(s) between corresponding normal subject population and subject representative parameter(s) increase, the magnitude of which "score" provides an indication of the cardiac status of said subject, with a "score" near zero being indicative of a subject properly categorized as a cardiac normal in that the magnitude(s) of subject representative parameter(s) are generally more closely matched to the magnitude(s) of corresponding normal subject population representative parameter(s), and with a progressively higher "score" being indicative of a subject progressively more properly categorized as a cardiac abnormal in that the magnitude(s) of subject representative parameter(s) are generally progressively less closely matched to the magnitude(s) of corresponding normal subject population representative parameter(s);

g. providing an output means for presenting said score;

said ECG system comprising ECG lead(s) which monitor electrodes affixed to a subject or member of a normal subject population, and which provide monitored signal(s) to an ECG monitor, said ECG monitor being functionally interconnected to a computational means which is programmed to accept ECG data from said ECG monitor and practice the method of steps a.–f., said computational means being functionally interconnected to an output means to enable practice of step g.

7. An ECG system for practicing a noninvasive method of investigating cardiac status of a subject and enabling classification of said subject into normal and abnormal cardiac categories utilizing electrocardiography ECG data obtained therefrom as in claim 6, which method further comprises performance of the steps of:

a. providing at least one coordinate system selected from the group consisting of magnitude vs. time, and magnitude vs. frequency;

b. for an ECG cycle portion, performing calculations necessary to plot and display and plotting and displaying normal subject population and subject ECG data in at least one frequency band range, as a function of at least one parameter selected from the group consisting of time and frequency, to respectively provide as desired, visually interpretable plots of ECG magnitude and power spectral density data, observation of which provides an indication of the cardiac status of said subject; and c. observing and interpreting displayed plot(s);

said ECG system computational means being programmed to perform said additional step and cause display thereof via output display means.

8. An ECG system for practicing a noninvasive method of investigating cardiac status of a subject and enabling classification of said subject into normal and abnormal cardiac categories utilizing electrocardiography ECG data obtained therefrom, said method comprising, in a functional sequence, performance of the steps of:

a. obtaining data from ECG cycle(s) from each of a multiplicity of members of a population of subjects who have been documented as normal subjects, in that they do not show risk factors for, or demonstrate detectable cardiac abnormality, by providing, selecting and monitoring at least one lead(s) of an ECG system;

b. establishing criteria for, and in line therewith selecting some ECG cycle portion and defining cycle portion data points therewithin, and calculating an average selected ECG cycle portion data set for at least one monitored ECG system lead(s), by, for a monitored ECG system lead, a procedure comprising combining corresponding ECG cycle portion data points for said selected ECG cycle portion for ECG cycle(s) obtained from each of a number of said multiplicity of members of a population of subjects who have been documented as normal subjects, and selecting a plurality of frequency bands and applying filtering techniques, to provide a plurality of data sets for said at least one ECG system lead(s) monitored, each said data set being a composite data set of said selected ECG cycle portion for said population of normal subjects in a monitored lead and selected frequency band range;

c. obtaining data from ECG cycle(s) from a subject, by monitoring at least one lead(s) of said ECG system, said ECG system lead(s) monitored being the same as the monitored ECG system lead(s) utilized in step a. to obtain data utilized in step b.;

d. selecting some ECG cycle portion, said ECG cycle portion being essentially that selected in step b. for said normal subject population, and calculating an average selected ECG cycle portion data set for said at least one monitored ECG system lead(s), by, for a monitored ECG system lead, a procedure comprising combining corresponding ECG cycle portion data points for said selected ECG cycle portion for subject ECG cycle(s), are selecting a plurality of frequency bands, said selected frequency bands being essentially those selected in step b. for said normal subject population, and applying filtering techniques which are essentially those applied in step b. for said normal subject population, to provide a plurality of data sets for said at least one monitored ECG system lead(s), each said data set being a composite data set of said selected ECG cycle portion for said subject in a monitored lead and selected frequency band range;

e. calculating corresponding representative parameter(s) and corresponding ratio(s) involving representative parameters from resulting composite data sets calculated in steps b. and d., in said selected frequency band ranges for monitored ECG system lead(s), for respectively, said normal subject population and said subject;

f. comparing specific ratio(s) of subject to corresponding specific ratio(s) of normal subject population representative parameters, and combining results thereof to arrive at a "score", the magnitude of which "score" results from difference(s) between magnitude(s) of corresponding specific ratio(s) of normal subject population and specific ratio(s) of subject representative parameters, which "score" magnitude increases when said difference(s) in magnitude(s) between specific ratio(s) of corresponding normal subject population and subject representative parameters increase, the magnitude of which "score" provides an indication of the cardiac status of said subject, with a "score" near zero being indicative of a subject properly categorized as a cardiac normal in that the magnitude(s) of ratio(s) of subject representative parameters are generally more closely matched to the magnitude(s) of corresponding ratio(s) of normal subject population representative parameters, and with a progressively higher "score" being indicative of a subject progressively more properly categorized as a cardiac abnormal in that the magnitude(s) of ratio(s) of subject representative parameters are generally progressively less closely matched to the magnitude(s) of ratio(s) of corresponding normal subject population representative parameters;

g. providing an output means for presenting said score; said ECG system comprising ECG lead(s) which monitor electrodes affixed to a subject or member of a normal subject population, and which provide monitored signal(s) to an ECG monitor, said ECG monitor being functionally interconnected to a computational means which is programmed to accept ECG data from said ECG monitor and practice the method of steps a.–f., said computational means being functionally interconnected to an output means to enable practice of step g.

9. An ECG system for practicing a noninvasive method of investigating cardiac status of a subject and enabling classification of said subject into normal and abnormal cardiac categories utilizing electrocardiography ECG data obtained therefrom as in claim 8, which method further comprises performance of the steps of:

a. providing at least one coordinate system selected from the group consisting of magnitude vs. time, and magnitude vs. frequency;

b. for an ECG cycle portion, performing calculations necessary to plot and display and plotting and displaying normal subject population and subject ECG data for at least one frequency band range, as a function of at least one parameter selected from the group consisting of time and frequency, to respectively provide as desired, visually interpretable plots of ECG magnitude and power spectral density data, observation of which provides an indication of the cardiac status of said subject; and c. observing and interpreting displayed plot(s);
said ECG system computational means being programmed to perform said additional step and cause display thereof via output display means.

10. An ECG system for practicing a noninvasive method of investigating cardiac status of a subject and enabling classification of said subject into normal and abnormal cardiac categories utilizing electrocardiography ECG data obtained therefrom, said method comprising, in a functional sequence, performance of the steps of:

a. obtaining data from ECG cycle(s) from each of a multiplicity of members of a population of subjects who have been documented as normal subjects, in that they do not show risk factors for, or demonstrate detectable cardiac abnormality, by providing, selecting and monitoring at least one lead(s) of an ECG system;

b. establishing criteria for, and in line therewith selecting some ECG cycle portion and defining cycle portion data points therewithin, and calculating an average selected ECG cycle portion data set for said at least one monitored ECG system lead(s), by, for a monitored ECG system lead, a procedure comprising combining corresponding ECG cycle portion data points for said selected ECG cycle portion for ECG cycle(s) obtained from each of a number of said multiplicity of members of a population of subjects who have been documented as normal subjects, and selecting a plurality of frequency bands and applying filtering techniques, to provide a plurality of data sets for said at least one ECG system lead(s) monitored, each said data set being a composite data set of said selected ECG cycle portion for said population of normal subjects in a monitored lead and selected frequency band range;

c. obtaining data from ECG cycle(s) from a subject, by monitoring at least one lead(s) of said ECG system, said ECG system lead(s) monitored being the same as the monitored ECG system lead(s) utilized in step a. to obtain data utilized in step b.;

d. selecting some ECG cycle portion, said ECG cycle portion being essentially that selected in step b. for said normal subject population, and calculating an average selected ECG cycle portion data set for said at least one monitored ECG system lead(s), by, for a monitored ECG system lead, a procedure comprising combining corresponding ECG cycle portion data points for said selected ECG cycle portion for subject ECG cycle(s), and selecting a plurality of frequency bands, said selected frequency bands being essentially those selected in step b. for said normal subject population, and applying filtering techniques which are essentially those applied in step b. for said normal subject population, to provide a plurality of data sets for said at least one monitored ECG system lead(s), each said data set being a composite data set of said selected ECG cycle portion for said subject in a monitored lead and selected frequency band range;

e. calculating corresponding representative parameter(s) and corresponding ratio(s) involving representative parameters from resulting composite data sets calculated in steps b. and d., in said selected frequency band ranges for monitored ECG system lead(s), for respectively, said normal subject population and said subject;

f. comparing specific subject and corresponding specific normal subject population representative parameter(s), and combining results thereof with the results of comparing specific ratio(s) of subject to corresponding specific ratio(s) of normal subject population representative parameters, to arrive at a "score", the magnitude of which "score" results from difference(s) in magnitude(s) between corresponding subject and normal subject population representative parameter(s) and difference(s) between magnitude(s) of corresponding ratio(s) of normal subject population, and ratio(s) of subject representative parameters, which "score" magnitude increases when difference(s) in magnitude(s) between corresponding subject and normal subject population representative parameter(s) increase and difference(s) in magnitude(s) between ratio(s) of corresponding normal subject population, and ratio(s) of subject representative parameters increase, the magnitude of which "score" provides an indication of the cardiac status of said subject, with a "score" near zero being indicative of a subject properly categorized as a cardiac normal in that magnitude(s) of subject representative parameter(s) are generally more closely matched to the magnitude(s) of corresponding normal subject population representative parameter(s) and magnitude(s) of ratio(s) of subject representative parameters are generally more closely matched to the magnitude(s) of corresponding ratio(s) of normal subject population representative parameters, and with a progressively higher "score" being indicative of a subject progressively more properly categorized as a cardiac abnormal in that magnitude(s) of subject representative parameter(s) are generally progressively less closely matched to the magnitude(s) of corresponding normal subject population representative parameter(s) and magnitude(s) of ratio(s) of subject representative parameter(s) are generally progressively less closely matched to the magnitude(s) of ratio(s) of corresponding normal subject population representative parameters;

g. providing an output means for presenting said score;

said ECG system comprising ECG lead(s) which monitor electrodes affixed to a subject or member of a normal subject population, and which provide monitored signal(s) to an ECG monitor, said ECG monitor being functionally interconnected to a computational means which is programmed to accept ECG data from said ECG monitor and practice the method of steps a.–f., said computational means being functionally interconnected to an output means to enable practice of step g.

11. An ECG system for practicing a noninvasive method of investigating cardiac status of a subject and enabling classification of said subject into normal and abnormal cardiac categories utilizing electrocardiography ECG data obtained therefrom as in claim 10, which method further comprises performance of the steps of:

a. providing at least one coordinate system selected from the group consisting of magnitude vs. time, and magnitude vs. frequency;

b. for an ECG cycle portion, performing calculations necessary to plot and display and plotting and displaying normal subject population and subject ECG data for at least one frequency band range, as a function of at least one parameter selected from the group consisting of time and frequency, to respectively provide as desired, visually interpretable plots of ECG magnitude and power spectral density data, observation of which provides an indication of the cardiac status of said subject; and c. observing and interpreting displayed plot(s);

said ECG system computational means being programmed to perform said additional step and cause display thereof via output display means.

12. A noninvasive method of tracking cardiac status of a subject utilizing electrocardiography ECG data obtained therefrom, said method comprising, in a functional sequence, performance of the steps of:

a. obtaining initial data from ECG cycles from a subject, by providing, selecting and monitoring at least one lead(s) of an ECG system;

b. establishing criteria for, and in line therewith selecting some ECG cycle portion and defining cycle portion data points therewithin, and calculating an average selected ECG cycle portion data set for said at least one monitored ECG system lead(s), by, for a monitored ECG system lead, a procedure comprising combining corresponding ECG cycle portion data points for said selected ECG cycle portion for ECG cycle(s) obtained from said subject, and selecting a plurality of frequency bands and applying filtering techniques, to provide a plurality of data sets for said at least one ECG system lead(s) monitored, each said data set being an initial composite data set of said selected ECG cycle portion for said subjects in a monitored lead and selected frequency band range;

c. obtaining follow-on data from ECG cycle(s) from a subject at a later time, by monitoring said at least one lead(s) of an ECG system, said ECG system lead(s) monitored being the same as the monitored ECG system lead(s) utilized in step a. to obtain data utilized in step b.;

d. selecting some ECG cycle portion, said ECG cycle portion being essentially that selected in step b. for said initial subject data, and calculating an average selected ECG cycle portion data set for at least one monitored ECG system lead(s), by, for a monitored ECG system lead, a procedure comprising combining corresponding ECG cycle portion data points for said selected ECG cycle portion for subject ECG cycle(s), and selecting a plurality of frequency bands, said selected frequency bands being essentially those selected in step b. for said initial subject data, and applying filtering techniques which are essentially those applied in step b. for said initial subject data, to provide a plurality of data sets for said at least one monitored ECG system lead(s), each said data set being a follow-on composite data set of said selected ECG cycle portion for said subject in a monitored lead and selected frequency band range;

e. calculating corresponding representative parameter(s) from resulting composite data sets calculated in steps b. and d., in said selected frequency band ranges for monitored ECG system lead(s), for respectively, said initial subject data and said follow-on subject data;

f. comparing values for at least one member of the group consisting of:
   initial subject to corresponding follow-on subject representative parameter(s), and
   specific ratio(s) of initial subject to corresponding specific ratio(s) of follow-on subject representative parameters,
and combining results thereof to arrive at a "score"; the magnitude of which "score" results from difference(s) between magnitude(s) of corresponding initial subject, and follow-on subject representative parameter(s) and/or ratio(s) of initial subject representative parameters, and follow-on subject representative parameters; which "score" magnitude increases when said difference(s) in magnitude(s) between corresponding initial subject, and follow-on subject, representative parameter(s) and/or ratio(s) of initial subject representative parameters, and follow-on subject representative parameters increase, the magnitude of which "score" provides an indication of a change in cardiac status of said subject, with a "score" near zero being indicative of a subject properly categorized as having undergone no cardiac change, and with a progressively higher "score" being indicative of a subject progressively more properly categorized as a subject who has undergone cardiac change; and g. providing an output means and presenting said score therewith;

said method optionally further comprising as additional step(s) groupings of steps selected from the group consisting of:
   h., i, and j;
   k., l, and m; and
   n and o.;

said steps h., i., and j., being:

h. determining the subject's cardiac ejection fraction, (in percent);

i. dividing said "score" determined in step f. by said cardiac ejection fraction, (in percent);

j. providing an output means and presenting the result provided in step i. therewith, and if said result is determined to be greater than one (1.0), considering said subject as at high risk for sudden death;

and said steps k., l. and m. being:

k. providing at least a coordinate system consisting of magnitude vs. time, and optionally a coordinate system consisting of magnitude vs. frequency, and in step b. selecting a portion of the ECG cycle including the region beyond the QRS complex and before the T wave;

l. for said ECG cycle portion, performing calculations necessary to plot and display initial subject and follow-on subject ECG data as a function of at least time and optionally frequency, to respectively provide as desired, visually interpretable plots of ECG magnitude and power spectral density data, observation of which provides an indication of the cardiac status of said subject; and m. providing an output display means and visually plotting and displaying therewith at least a magnitude vs. time plot for said ECG cycle portion beyond the QRS complex and before the T wave, then noting if Rhomboids are therewithin, and if present, considering said subject as at high risk for sudden death; and said steps n. and o. being:

n. determining realtive magnitude pattern(s) amongst at least one selection from the group consisting of:
   subject represenatative parameter values; and
   ratios of subject representative parameter values; and o. providing an output means, and via said output means obtaining and utilizing said relative magnitude pattern (s) as additional basis for tracking said subject cardiac status.

13. A noninvasive method of tracking the cardiac status of a subject utilizing electrocardiography ECG data obtained therefrom as in claim 12, which further comprises performance of the step of applying a confidence level acceptance test to results of comparing corresponding specific initial subject to specific follow-on subject representative parameters, and/or corresponding specific ratios of said representative parameters of follow-on subject, to specific ratios of initial normal subject, representative parameters prior to combining results thereof to arrive at a "score", said confidence level test comprising:

a. the step of determining mean and standard deviation acceptance parameters for specific initial subject representative parameter(s) and/or specific ratio(s) of initial subject representative parameter(s) based upon the ECG data from which said composite data set of said selected ECG cycle portion for said initial subject data was calculated;

b. the step of determining an acceptance parameter for each specific corresponding follow-on subject representative parameter and/or each corresponding specific ratio of follow-on subject representative parameters based upon the ECG data from which said composite data set of said selected ECG cycle portion for said follow-on subject data was calculated; and c. the step of accepting the results of comparing a specific follow-on subject representative parameter to a corresponding specific initial subject representative parameter in arriving at said "score", only if the acceptance parameter for said specific follow-on subject representative parameter is set off by at least one associated initial subject acceptance standard deviation from the acceptance mean of the corresponding specific initial subject representative parameter; and/or accepting the results of comparing a specific ratio of follow-on subject representative parameters to a corresponding specific ratio of representative parameters for said initial subject population, in arriving at said "score", only if the acceptance parameter of said specific ratio of said follow-on subject representative parameters is set off by at least one associated initial subject acceptance standard deviation from the acceptance mean of said corresponding specific ratio of initial subject representative parameters.

14. A noninvasive method of tracking cardiac status change in a subject utilizing electrocardiography ECG data obtained therefrom as in claim 12, in which said follow-on data is obtained at a time after acquisition of said initial data selected from the group consisting of:

immediately thereafter as in a continuous monitoring scenario; and after application of a suitable stress test; and after intervention; and after medical therapy;

the benefit being identification of a subject who has undergone cardiac change.

15. A noninvasive method of tracking cardiac status of a subject utilizing electrocardiography ECG data obtained therefrom as in claim 12, which further comprises determining if said subject is at high risk for sudden death by the additional steps of:

a. determining the subject's cardiac ejection fraction, (in percent);

b. dividing said "score" by said cardiac ejection fraction, (in percent); and c. utilizing said output means, providing the result determined in step b. by use thereof, and if said result is greater observed than one (1.0), considering said subject as at high risk for sudden death.

16. A method of analyzing stored electrocardiography ECG data of a specific subject, comprising the steps of:

a. obtaining data from ECG cycle(s) of said subject, and from subject(s) identified as normal, then selecting frequency band(s), and separately applying necessary filtering techniques to said data obtained from said subject and from said subject(s) identified as normal to separate the data obtained from said subject into at least one frequency band(s), and said data obtained from said subject(s) identified as normal into essentially equivalent frequency band(s);

b. establishing criteria for, and in line therewith selecting some ECG cycle portion and arriving at representative parameter(s) for each selected frequency band for data obtained from each of the subject and the subject(s) identified as normal;

c. comparing said subject representative parameter(s) with corresponding subject(s) identified as normal representative parameter(s); and d. combining selected differences between corresponding subject and subject(s) identified as normal representative parameter(s) to arrive at a score, said score being the result of differences in magnitudes of corresponding subject and normal representative parameter(s); and e. providing an output means and presenting said score by use thereof.

17. A method of analyzing stored electrocardiography ECG data of a specific subject as in claim 16, which further comprises determining if said subject is at high risk for sudden death by the additional steps of:

a. determining the subject's cardiac ejection fraction, (in percent); and b. dividing said "score" by said cardiac ejection fraction, (in percent); and c. utilizing said output means, providing the result determined in step b. by use thereof, and if said result is greater observed than one (1.0), considering said subject as at high risk for sudden death.

18. A noninvasive method of investigating cardiac status of a subject utilizing electrocardiography ECG data obtained therefrom, said method enabling classification of said subject into normal and abnormal cardiac categories and determining if said subject is at high risk for sudden death, said method comprising, in a functional sequence, performance of the steps of:

a. obtaining data from ECG cycle(s) from each of a multiplicity of members of a population of subjects who have been documented as normal subjects, in that they do not show risk factors for, or demonstrate detectable cardiac abnormality, by providing, selecting and monitoring at least one lead(s) of said ECG system;

b. establishing criteria for, and in line therewith selecting some ECG cycle portion and defining cycle portion data points therewithin, and calculating an average selected ECG cycle portion data set for said at least one monitored ECG system lead(s) by, for a monitored ECG system lead, a procedure comprising combining corresponding ECG cycle portion data points for said selected ECG cycle portion for ECG cycle(s) obtained from each of a number of members of said multiplicity of members of a population of subjects who have been documented as normal subjects, each said calculated average selected ECG cycle portion data set being a composite data set of said selected ECG cycle portion for said population of normal subjects, for a monitored ECG system lead;

c. obtaining data from ECG cycle(s) from a subject, by monitoring at least one lead(s) of said ECG system, said ECG system lead(s) monitored being the same as the monitored ECG system lead(s) utilized in step a. to obtain data utilized in step b.;

d. selecting some ECG cycle portion, which is essentially that selected in step b., and calculating an average selected ECG cycle portion data set for said at least one monitored ECG system lead(s) by, for a monitored ECG system lead, a procedure comprising combining corresponding ECG cycle portion data points for said selected ECG cycle portion for ECG cycle(s) obtained from said subject, each said calculated average selected ECG cycle portion data set being a composite data set of said selected ECG cycle portion for said subject, for a monitored ECG system lead;

e. calculating corresponding representative parameter(s) from resulting composite data sets calculated in steps b. and d., for monitored ECG system lead(s), for, respectively, said normal subject population and said subject;

f. comparing subject to corresponding normal subject population representative parameter(s), and combining results thereof to arrive at a "score", the magnitude of which "score" results from difference(s) between magnitude(s) of corresponding normal subject population, and subject representative parameter(s), which "score" magnitude increases when said difference(s) in magnitude(s) between corresponding normal subject population, and subject, representative parameter(s) increase, the magnitude of which "score" provides an indication of the cardiac status of said subject, with a "score" near zero being indicative of a subject properly categorized as a cardiac normal in that the magnitude(s) of subject representative parameter(s) are generally more closely matched to the magnitude(s)

of corresponding normal subject population representative parameter(s), and with a progressively higher "score" being indicative of a subject progressively more properly categorized as a cardiac abnormal in that the magnitude(s) of subject representative parameter(s) are generally progressively less closely matched to the magnitude(s) of corresponding normal subject population representative parameter(s);

said method further comprising as additional steps at least one grouping of steps selected from the group consisting of:

g., h. and i;

j., k, and l; and m. and n.;

said steps g., h., and i., being:

g. determining the subject's cardiac ejection fraction, (in percent);

h. dividing said "score" by said cardiac ejection fraction, (in percent);

i. providing an output means and presenting the result provided in step h. therewith, and if said result is determined to be greater than one (1.0), considering said subject as at high risk for sudden death;

and said steps j., k., and l. being:

j. providing at least a coordinate system consisting of magnitude vs. time, and optionally a coordinate system consisting of magnitude vs. frequency, and in step b. selecting portion of the ECG cycle including the region beyond the QRS complex and before the T wave;

k. for said ECG cycle portion, performing calculations necessary to plot and display normal subject population and subject ECG data as a function of at least time and optionally frequency, to respectively provide as desired, visually interpretable plots of ECG magnitude and power spectral density data, observation of which provides an indication of the cardiac status of said subject; and l. providing an output display means and visually plotting and displaying therewith at least a magnitude vs. time plot for said ECG cycle portion beyond the QRS complex and before the T wave, then noting if Rhomboids are therewithin, and if present, considering said subject as at high risk for sudden death; and said steps m. and n. being:

m. determining realtive magnitude pattern(s) amongst at least two subject representative parameter values, and utilizing said pattern(s) as additional basis for insight to cardiac abnormality; and n. providing an output means, and via said output means obtaining and utilizing said relative magnitude pattern(s) as additional basis for investigating the cardiac status of said subject.

19. A system for practicing a noninvasive method of investigating cardiac status of a subject and enabling classification of a subject into normal and abnormal cardiac categories utilizing electrocardiography (ECG) data obtained therefrom as in claim 18, which method further comprises performance of the step of applying a confidence level acceptance test to results of comparing specific subject, to corresponding specific normal subject population, representative parameter(s) prior to combining results thereof to arrive at a "score", said confidence level test comprising:

a. the step of determining mean and standard deviation acceptance parameters for specific normal subject population representative parameter(s) based upon the (ECG) data from which said composite data set of said selected (ECG) cycle portion for said population of normal subjects was calculated;

b. the step of determining an acceptance parameter for each corresponding specific subject representative parameter based upon the (ECG) data from which said composite data set of said selected (ECG) cycle portion for said subject was calculated; and c. the step of accepting the results of comparing a specific subject representative parameter, to a corresponding specific normal subject population representative parameter, in arriving at said "score", only if the acceptance parameter for said specific subject representative parameter is set off by at least one associated normal subject population acceptance standard deviation from the acceptance mean of said corresponding specific normal subject population representative parameter.

20. A noninvasive method of investigating cardiac status of a subject utilizing electrocardiography ECG data obtained therefrom, said method enabling classification of said subject into normal and abnormal cardiac categories and determining if said subject is at high risk for sudden death, said method comprising, in a functional sequence, performance of the steps of:

a. obtaining data from ECG cycle(s) from each of a multiplicity of members of a population of subjects who have been documented as normal subjects, in that they do not show risk factors for, or demonstrate detectable cardiac abnormality, by providing, selecting and monitoring at least one lead(s) of said ECG system;

b. establishing criteria for, and in line therewith selecting some ECG cycle portion, and defining cycle portion data points therewithin, and calculating an average selected ECG cycle portion data set for at least one monitored ECG system lead(s) by, for a monitored ECG system lead, a procedure comprising combining corresponding ECG cycle portion data points for said selected ECG cycle portion for ECG cycle(s) obtained from each of a number of members of said multiplicity of members of a population of subjects who have been documented as normal subjects, each said calculated average selected ECG cycle portion data set being a composite data set of said selected ECG cycle portion for said population of normal subjects, for a monitored ECG system lead;

c. obtaining data from ECG cycle(s) from a subject, by monitoring at least one lead(s) of ECG said system, said ECG system lead(s) monitored being the same as the monitored ECG system lead(s) utilized in step a. to obtain data utilized in step b.;

d. selecting some ECG cycle portion, which is essentially that selected in step b., and calculating an average selected ECG cycle portion data set for said at least one monitored ECG system lead(s) by, for a monitored ECG system lead, a procedure comprising combining corresponding ECG cycle portion data points for said selected ECG cycle portion for ECG cycle(s) obtained from said subject, each said calculated average selected ECG cycle portion data set being a composite data set of said selected ECG cycle portion for said subject, for a monitored ECG system lead;

e. calculating corresponding representative parameter(s) and corresponding ratio(s) involving representative parameters from resulting composite data sets calculated in steps b. and d., for monitored ECG system lead(s), for, respectively, said normal subject population and said subject;

f. comparing specific ratio(s) of subject to corresponding specific ratio(s) of normal subject population representative parameters, and combining results thereof to arrive at a "score", the magnitude of which "score" results from difference(s) between magnitude(s) of specific corresponding ratio(s) of normal subject population, and ratio(s) of subject representative parameters, which "score" magnitude increases when said difference(s) in magnitude(s) between specific ratio(s) of corresponding normal subject population, and specific ratio(s) of subject representative parameters increase, the magnitude of which "score" provides an indication of the cardiac status of said subject, with a "score" near zero being indicative of a subject properly categorized as a cardiac normal in that the magnitude(s) of ratio(s) of subject representative parameters are generally more closely matched to the magnitude(s) of corresponding ratio(s) of normal subject population representative parameters, and with a progressively higher "score" being indicative of a subject progressively more properly categorized as a cardiac abnormal in that the magnitude(s) of ratio(s) of subject representative parameters are generally progressively less closely matched to the magnitude(s) of ratio(s) of corresponding normal subject population representative parameters;

said method further comprising as additional steps at least one grouping of steps selected from the group consisting of:
  g., h. and i;
  j., k, and l; and
  m. and n.;
said steps g., h., and i., being:
  g. determining the subject's cardiac ejection fraction, (in percent);
  h. dividing said "score" by said cardiac ejection fraction, (in percent);
  i. providing an output means and presenting the result provided in step h. therewith, and if said result is determined to be greater than one (1.0), considering said subject as at high risk for sudden death;
and said steps j., k., and l. being:
  j. providing at least a coordinate system consisting of magnitude vs. time, and optionally a coordinate system consisting of magnitude vs. frequency, and in step b. selecting a portion of the ECG cycle including the region beyond the QRS complex and before the T wave;
  k. for said ECG cycle portion, performing calculations necessary to plot and display normal subject population and subject ECG data as a function of at least time and optionally frequency, to respectively provide as desired, visually interpretable plots of ECG magnitude and power spectral density data, observation of which provides an indication of the cardiac status of said subject; and
  l. providing an output display means and visually plotting and displaying therewith at least a magnitude vs. time plot for said ECG cycle portion beyond the QRS complex and before the T wave, then noting if Rhomboids are therewithin, and if present, considering said subject as at high risk for sudden death; and
said steps m. and n. being:
  m. determining realtive magnitude pattern(s) amongst at least two ratios of subject representative parameter values, and utilizing said pattern(s) as additional basis for insight to cardiac abnormality; and
  n. providing an output means, and via said output means obtaining and utilizing said relative magnitude pattern(s) as additional basis for investigating the cardiac status of said subject.

21. A system for practicing a noninvasive method of investigating cardiac status of a subject and enabling classification of a subject into normal and abnormal cardiac categories utilizing electrocardiography (ECG) data obtained therefrom as in claim 20, which method further comprises performance of the step of applying a confidence level acceptance test to results of comparing specific ratio(s) of subject, to corresponding specific ratio(s) of normal subject population representative parameters prior to combining results thereof to arrive at a "score", said confidence level test comprising:
  a. the step of determining mean and standard deviation acceptance parameters for specific ratio(s) of normal subject population representative parameters based upon the (ECG) data from which said composite data set of said selected (ECG) cycle portion for said population of normal subjects was calculated;
  b. the step of determining an acceptance parameter for each corresponding specific ratio of subject representative parameters based upon the (ECG) data from which said composite data set of said selected (ECG) cycle portion for said subject was calculated; and
  c. the step of accepting the results of comparing a specific ratio of subject representative parameters, to a corresponding specific ratio of representative parameters for said normal subject population, in arriving at said "score", only if said acceptance parameter for said specific ratio of said subject representative parameters is set off by at least one associated normal subject population acceptance standard deviation from the acceptance mean of said corresponding specific ratio of normal subject population representative parameters.

22. A noninvasive method of investigating cardiac status of a subject utilizing electrocardiography ECG data obtained therefrom, said method enabling classification of said subject into normal and abnormal cardiac categories and determining if said subject is at high risk for sudden death, said method comprising, in a functional sequence, performance of the steps of:
  a. obtaining data from ECG cycle(s) from each of a multiplicity of members of a population of subjects who have been documented as normal subjects, in that they do not show risk factors for, or demonstrate detectable cardiac abnormality, by providing, selecting and monitoring at least one lead(s) of an ECG system;
  b. establishing criteria for, and in line therewith selecting some ECG cycle portion and defining cycle portion data points therewithin, and calculating an average selected ECG cycle portion data set for said at least one monitored ECG system lead(s), by, for a monitored ECG system lead, a procedure comprising combining corresponding ECG cycle portion data points for said selected ECG cycle portion for ECG cycle(s) obtained from each of a number of said multiplicity of members of a population of subjects who have been documented as normal subjects, and selecting a plurality of frequency bands and applying filtering techniques, to provide a plurality of data sets for said at least one ECG system lead(s) monitored, each said data set being a composite data set of said selected ECG cycle portion for said population of normal subjects in a monitored lead and selected frequency band range;

c. obtaining data from ECG cycle(s) from a subject, by monitoring at least one lead(s) of said ECG system, said ECG system lead(s) monitored being the same as the monitored ECG system lead(s) utilized in step a. to obtain data utilized in step b.;

d. selecting some ECG cycle portion, said ECG cycle portion being essentially that selected in step b. for said normal subject population, and calculating an average selected ECG cycle portion data set for said at least one monitored ECG system lead(s), by, for a monitored ECG system lead, a procedure comprising combining corresponding ECG cycle portion data points for said selected ECG cycle portion for subject ECG cycle(s), and selecting a plurality of frequency bands, said selected frequency bands being essentially those selected in step b. for said normal subject population, and applying filtering techniques which are essentially those applied in step b. for said normal subject population, to provide a plurality of data sets for said at least one monitored ECG system lead(s), each said data set being a composite data set of said selected ECG cycle portion for said subject in a monitored lead and selected frequency band range;

e. calculating corresponding representative parameter(s) and corresponding ratio(s) involving representative parameters from resulting composite data sets calculated in steps b. and d., in said selected frequency band ranges for monitored ECG system lead(s), for respectively, said normal subject population and said subject;

f. comparing specific subject and corresponding specific normal subject population representative parameter(s), and combining results thereof with the results of comparing specific ratio(s) of subject to corresponding specific ratio(s) of normal subject population representative parameters, to arrive at a "score", the magnitude of which "score" results from difference(s) in magnitude(s) between corresponding subject and normal subject population representative parameter(s) and difference(s) between magnitude(s) of corresponding ratio(s) of normal subject population, and ratio(s) of subject representative parameters, which "score" magnitude increases when difference(s) in magnitude(s) between corresponding subject and normal subject population representative parameter(s) increase and difference(s) in magnitude(s) between ratio(s) of corresponding normal subject population, and ratio(s) of subject representative parameters increase, the magnitude of which "scores" provides an indication of the cardiac status of said subject, with a "score" near zero being indicative of a subject properly categorized as a cardiac normal in that magnitude(s) of subject representative parameter(s) are generally more closely matched to the magnitude(s) of corresponding normal subject population representative parameter(s) and magnitude(s) of ratio(s) of subject representative parameters are generally more closely matched to the magnitude(s) of corresponding ratio(s) of normal subject population representative parameters, and with a progressively higher "score" being indicative of a subject progressively more properly categorized as a cardiac abnormal in that magnitude(s) of subject representative parameter(s) are generally progressively less closely matched to the magnitude(s) of corresponding normal subject population representative parameter(s) and magnitude(s) of ratio(s) of subject representative parameter(s) are generally progressively less closely matched to the magnitude(s) of ratio(s) of corresponding normal subject population representative parameters; said method further comprising as additonal steps at least one grouping of steps selected from the group consisting of:

g., h. and i;

j., k, and l; and m. and n.;

said steps g., h., and i., being:

g. determining the subject's cardiac ejection fraction, (in percent);

h. dividing said "score" by said cardiac ejection fraction, (in percent);

i. providing an output means and presenting the result provided in step h. therewith, and if said result is determined to be greater than one (1.0), considering said subject as at high risk for sudden death;

and said steps j., k., and l. being:

j. providing at least a coordinate system consisting of magnitude vs. time, and optionally a coordinate system consisting of magnitude vs. frequency, and in step b. selecting a portion of the ECG cycle including the region beyond the QRS complex and before the T wave;

k. for said ECG cycle portion, performing calculations necessary to plot and display normal subject population and subject ECG data as a function of at least time and optionally frequency, to respectively provide as desired, visually interpretable plots of ECG magnitude and power spectral density data, observation of which provides an indication of the cardiac status of said subject; and l. providing an output display means and visually plotting and displaying therewith at least a magnitude vs. time plot for said ECG cycle portion beyond the QRS complex and before the T wave, then noting if Rhomboids are therewithin, and if present, considering said subject as at high risk for sudden death; and said steps m. and n. being:

m. determining realtive magnitude pattern(s) amongst at least one selection from the group consisting of:
subject represenatative parameter values; and
ratios of subject representative parameter values; and n. providing an output means, and via said output means obtaining and utilizing said relative magnitude pattern (s) as additional basis for investigating the cardiac status of said subject.

23. A system for practicing a noninvasive method of investigating cardiac status of a subject and enabling classification of a subject into normal and abnormal cardiac categories utilizing electrocardiography (ECG) data obtained therefrom as in claim 22, which method further comprises performance of the step of applying a confidence level acceptance test to results of comparing subject, to corresponding normal subject population representative parameter(s), and the results of comparing ratios of subject representative parameters to corresponding ratios of normal subject population representative parameters, prior to combining results thereof to arrive at a "score", said confidence level test comprising:

a. the step of determining mean and standard deviation acceptance parameters for specific normal subject population representative parameter(s) and specific ratio(s) of normal subject population representative parameters based upon the (ECG) data from which said composite data set of said selected (ECG) cycle portion for said population of normal subjects was calculated;

b. the step of determining an acceptance parameter for each corresponding specific subject representative parameter and each corresponding specific ratio of subject representative parameters based upon the (ECG) data from which said composite data set of said selected (ECG) cycle portion for said subject was calculated; and c. the step of accepting the results of comparing a specific subject representative parameter to a corresponding specific normal subject population representative parameter in arriving at said "score", only if the acceptance parameter for said specific subject representative parameter is set off by at least one associated normal subject population acceptance standard deviation from the acceptance mean of the corresponding specific normal subject population representative parameter; and accepting the results of comparing a specific ratio of subject representative parameters to a corresponding specific ratio of representative parameters for said normal subject population, in arriving at said "score", only if the acceptance parameter of said specific ratio of said subject representative parameters is set off by at least one associated normal subject population acceptance standard deviation from the acceptance mean of said corresponding specific ratio of normal subject population representative parameters.

24. A system for practicing a noninvasive method of investigating cardiac status of a subject and enabling classification of a subject into normal and abnormal cardiac categories utilizing electrocardiography ECG data obtained therefrom, said method comprising, in a functional sequence, performance of the steps of:

a. obtaining data from ECG cycle(s) from each of a multiplicity of members of a population of subjects who have been documented as normal subjects, in that they do not show risk factors for, or demonstrate detectable cardiac abnormality, by providing, selecting and monitoring at least one lead(s) of an ECG system;

b. establishing criteria for, and in line therewith selecting some ECG cycle portion and calculating an average selected ECG cycle portion data set for at least one monitored ECG system lead(s), by, for a monitored ECG system lead, a procedure comprising combining corresponding ECG cycle portion data points for said selected ECG cycle portion for ECG cycle(s) obtained from each of a number of said multiplicity of members of a population of subjects who have been documented as normal subjects, and selecting a plurality of frequency bands and applying filtering techniques, to provide a plurality of data sets for said at least one ECG system lead(s) monitored, each said data set being a composite data set of said selected ECG cycle portion for said population of normal subjects in a monitored lead and selected frequency band range;

c. obtaining data from ECG cycle(s) from a subject, by monitoring at least one lead(s) of an ECG system, said ECG system lead(s) monitored being the same as the monitored ECG system lead(s) utilized in step a. to obtain data utilized in step b.;

d. selecting some ECG cycle portion, said ECG cycle portion being essentially that selected in step b. for said normal subject population, and calculating an average selected ECG cycle portion data set for at least one monitored ECG system lead(s), by, for a monitored ECG system lead, a procedure comprising combining corresponding ECG cycle portion data points for said selected ECG cycle portion for subject ECG cycle(s), and selecting a plurality of frequency bands, said selected frequency bands being essentially those selected in step b. for said normal subject population, and applying filtering techniques which are essentially those applied in step b. for said normal subject population, to provide a plurality of data sets for said at least one monitored ECG system lead(s), each said data set being a composite data set of said selected ECG cycle portion for said subject in a monitored lead and selected frequency band range;

e. providing an output display means and performing at least one of the following steps f. and g.;

f. calculating mean and standard deviation representative parameters from at least one resulting composite data set calculated in step b., said mean and standard deviation parameters being from a selected frequency band range for a monitored ECG system lead, and providing a coordinate system consisting of magnitude vs. time on ordinate and abscissa respectively and plotting and displaying on said coordinate system loci consisting of:

1. normal subject population standard deviation bounds located above and below said normal subject population mean, and
2. a corresponding subject data set, then observing differences between normal subject population and subject data plots, with a subject data set falling within the normal subject standard deviation bounds being indicative of a subject properly classified as a cardiac normal, and with a subject data set falling progressively further outside said normal subject standard deviation bounds being indicative of a subject progressively more properly classified as a cardiac abnormal;

g. calculating power spectral density data for at least one resulting composite data set calculated in step b. and for a corresponding resulting composite data set calculated in step d. for a selected frequency band range for a monitored ECG system lead, and providing a coordinate system consisting of magnitude vs. frequency on ordinate and abscissa respectively and plotting and displaying on said coordinate system power spectral density data loci, then observing differences between normal subject population and subject data loci, with closely matched corresponding subject and normal subject population data set power spectral density loci being indicative of a subject properly classified as a cardiac normal and with progressively more mismatched subject and normal subject population data set power spectral density loci being indicative of a subject progressively more properly classified as a cardiac abnormal;

said ECG system comprising ECG lead(s) which monitor electrodes affixed to a subject or member of a normal subject population, and which provide monitored signal(s) to an ECG monitor, said ECG monitor being functionally interconnected to a computational means which is programmed to accept ECG data from said ECG monitor and practice the method of steps a.–e., said computational means being functionally interconnected to an output means to enable practice of steps f. or g.

25. A noninvasive method of tracking cardiac status change in a subject utilizing electrocardiography ECG data obtained therefrom, said method comprising, in a functional sequence, performance of the steps of:

a. obtaining initial data from ECG cycles from a subject by providing, selecting and monitoring at least one lead(s) of said ECG system;

b. establishing criteria for, and in line therewith selecting some ECG cycle portion and calculating an average selected ECG cycle portion data set for at least one monitored ECG system lead(s), by, for a monitored ECG system lead, a procedure comprising combining corresponding ECG cycle portion data points for said selected ECG cycle portion for ECG cycle(s) obtained from said subject, and selecting a plurality of frequency bands and applying filtering techniques, to provide a plurality of data sets for said at least one ECG system lead(s) monitored, each said data set being an initial composite data set of said selected ECG cycle portion for said subjects in a monitored lead and selected frequency band range;

c. obtaining follow-on data from ECG cycle(s) from a subject at a later time, by monitoring at least one lead(s) of an ECG system, said ECG system lead(s) monitored being the same as the monitored ECG system lead(s) utilized in step a. to obtain data utilized in step b.;

d. selecting some ECG cycle portion, said ECG cycle portion being essentially that selected in step b. for said initial subject data, and calculating an average selected ECG cycle portion data set for at least one monitored ECG system lead(s), by, for a monitored ECG system lead, a procedure comprising combining corresponding ECG cycle portion data points for said selected ECG cycle portion for subject ECG cycle(s), and selecting a plurality of frequency bands, said selected frequency bands being essentially those selected in step b. for said initial subject data, and applying filtering techniques which are essentially those applied in step b. for said initial subject data, to provide a plurality of data sets for said at least one monitored ECG system lead(s), each said data set being a follow-on composite data set of said selected ECG cycle portion for said subject in a monitored lead and selected frequency band range;

e. providing an output display means and performing at least one of the following steps f. and g.;

f. calculating mean and standard deviation representative parameters from at least one resulting composite data set calculated in step b., said mean and standard deviation parameters being from a selected frequency band range for a monitored ECG system lead, and providing a coordinate system consisting of magnitude vs. time on ordinate and abscissa respectively and plotting and displaying on said coordinate system loci consisting of:
  1. initial subject standard deviation bounds located above and below said initial subject data set mean, and
  2. a corresponding follow-on subject data set, then observing differences between initial subject and follow-on subject data plots, with a follow-on subject data set falling within the initial subject data set standard deviation bounds being indicative of a subject properly classified as having not undergone cardiac change, and with a follow-on subject data set falling progressively further outside said initial subject data set standard deviation bounds being indicative of a subject progressively more properly classified as having undergone cardiac change;

g. calculating power spectral density data for at least one resulting composite data set calculated in step b. and for a corresponding resulting composite data set calculated in step d. for a selected frequency band range for a monitored ECG system lead, and providing a coordinate system consisting of magnitude vs. frequency on ordinate and abscissa respectively and plotting and displaying on said coordinate system power spectral density data loci, then observing differences between initial subject and follow-on subject data loci, with closely matched corresponding initial subject and follow-on subject data set power spectral density loci being indicative of a subject who has not undergone cardiac change and with progressively more mismatched initial subject and follow-on subject data set power spectral density loci being indicative of a subject progressively more properly classified having undergone cardiac change.

26. An ECG system for practicing a noninvasive method of tracking cardiac status change in a subject utilizing electrocardiography ECG data obtained therefrom, enabling classification of said subject into normal and abnormal cardiac categories utilizing electrocardiography ECG data obtained therefrom, said method comprising, in a functional sequence, performance of the steps of:

a. obtaining initial data from ECG cycles from a subject by providing, selecting and monitoring at least one lead(s) of said ECG system;

b. establishing criteria for, and in line therewith selecting some ECG cycle portion and calculating an average selected ECG cycle portion data set for said at least one monitored ECG system lead(s) by, for a monitored ECG system lead, a procedure comprising combining corresponding ECG cycle portion data points for said selected ECG cycle portion for ECG cycle(s) obtained from said subject, and selecting a plurality of frequency bands and applying filtering techniques, to provide a plurality of data sets for said at least one ECG system lead(s) monitored, each said data set being an initial composite data set of said selected ECG cycle portion for said subjects in a monitored lead and selected frequency band range;

c. obtaining follow-on data from ECG cycle(s) from a subject at a later time, by monitoring said at least one lead(s) of an ECG system, said ECG system lead(s) monitored being the same as the monitored ECG system lead(s) utilized in step a. to obtain data utilized in step b.;

d. selecting some ECG cycle portion, said ECG cycle portion being essentially that selected in step b. for said initial subject data, and calculating an average selected ECG cycle portion data set for said at least one monitored ECG system lead(s), by, for a monitored ECG system lead, a procedure comprising combining corresponding ECG cycle portion data points for said selected ECG cycle portion for subject ECG cycle(s), and selecting a plurality of frequency bands, said selected frequency bands being essentially those selected in step b. for said initial subject data, and applying filtering techniques which are essentially those applied in step b. for said initial subject data, to provide a plurality of data sets for said at least one monitored ECG system lead(s), each said data set being a follow-on composite data set of said selected ECG cycle portion for said subject in a monitored lead and selected frequency band range;

e. providing an output display means and performing at least one of the following steps f. and g.;

f. calculating mean and standard deviation representative parameters from at least one resulting composite data set calculated in step b., said mean and standard deviation parameters being from a selected frequency band range for a monitored ECG system lead, and providing a coordinate system consisting of magnitude vs. time on ordinate and abscissa respectively and plotting and displaying on said coordinate system loci consisting of:
1. initial subject standard deviation bounds located above and below said initial subject data set mean, and
2. a corresponding follow-on subject data set, then observing differences between initial subject and follow-on subject data plots, with a follow-on subject data set falling within the initial subject data set standard deviation bounds being indicative of a subject properly classified as having not undergone cardiac change, and with a follow-on subject data set falling progressively further outside said initial subject data set standard deviation bounds being indicative of a subject progressively more properly classified as having undergone cardiac change;

g. calculating power spectral density data for at least one resulting composite data set calculated in step b. and for a corresponding resulting composite data set calculated in step d. for a selected frequency band range for a monitored ECG system lead, and providing a coordinate system consisting of magnitude vs. frequency on ordinate and abscissa respectively and plotting and displaying on said coordinate system power spectral density data loci, then observing differences between initial subject and follow-on subject data loci, with closely matched corresponding initial subject and follow-on subject data set power spectral density loci being indicative of a subject who has not undergone cardiac change and with progressively more mismatched initial subject and follow-on subject data set power spectral density loci being indicative of a subject progressively more properly classified having undergone cardiac change;

said ECG system comprising ECG lead(s) which monitor electrodes affixed to a subject or member of a normal subject population, and which provide monitored signal(s) to an ECG monitor, said ECG monitor being functionally interconnected to a computational means which is programmed to accept ECG data from said ECG monitor and practice the method of steps a.–e., said computational means being functionally interconnected to an output means to enable practice of steps f. or g.

* * * * *